United States Patent [19]
Curiel et al.

[11] Patent Number: 6,074,640
[45] Date of Patent: Jun. 13, 2000

[54] ENHANCEMENT OF TUMOR CELL RADIOSENSITIVITY USING SINGLE CHAIN INTRACELLULAR ANTIBODIES

[75] Inventors: David T. Curiel, Birmingham; Murray Stackhouse, Helena; Donald J. Buchsbaum, Birmingham, all of Ala.

[73] Assignee: UAB Research Foundation, Birmingham, Ala.

[21] Appl. No.: 08/961,327

[22] Filed: Oct. 30, 1997

Related U.S. Application Data

[60] Provisional application No. 60/029,673, Oct. 30, 1996.
[51] Int. Cl.[7] .................... A61K 39/395; C07K 16/18; C07K 16/30; C07H 21/04
[52] U.S. Cl. ...................... 424/130.1; 424/135.1; 424/138.1; 435/69.1; 435/69.6; 514/2; 514/44; 530/387.1; 530/387.3; 530/387.7; 530/388.22; 536/23.53
[58] Field of Search ............... 424/130.1, 135.1, 424/138.1; 435/69.1, 69.6; 514/2, 44; 530/387.1, 387.3, 387.7, 388.22; 536/23.53

[56] References Cited

U.S. PATENT DOCUMENTS 5,700,823   12/1997   Hirth .

FOREIGN PATENT DOCUMENTS 9607321   3/1996   WIPO .

OTHER PUBLICATIONS

Barnes et al; Clinical Cancer Research 2,1089; Jul. 1996.
Pietras, Oncogene 9:1829, 1994.
Hancock Cancer Research 51:4575, 1991.
Dorland's Pocket Medical Dictionary 1977 p. 456.
Richardson, Trends Biotechnol 13(8):306 1995 (May 16).
Deshane, J. Clin. Invest 96:2980, 1995.

*Primary Examiner*—Nancy A. Johnson
*Attorney, Agent, or Firm*—Benjamin Aaron Adler

[57] ABSTRACT

The present invention provides a method of enhancing the chemosensitivity and radiosensitivity of a neoplastic cell expressing an oncoprotein that stimulates proliferation of the cell, comprising introducing into the cell a nucleic acid molecule encoding an antibody homologue, wherein the antibody homologue is expressed intracellularly and binds to the oncoprotein intracellularly in the endoplasmic reticulum of the cell. The present invention is also directed to a method for enhancing the inhibition of proliferation of a neoplastic cell expressing an oncoprotein that stimulates proliferation of the cell, comprising the steps of: introducing into the cell a nucleic acid molecule encoding an antibody homologue, wherein the antibody homologue is expressed intracellularly and binds to the protein intracellularly; and contacting said cell with an anti-neoplastic agent.

19 Claims, 44 Drawing Sheets

(3 of 44 Drawing Sheet(s) Filed in Color)

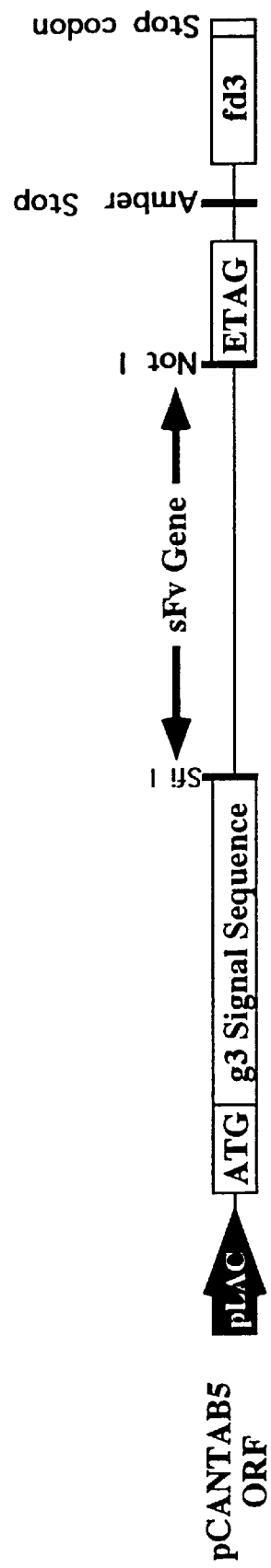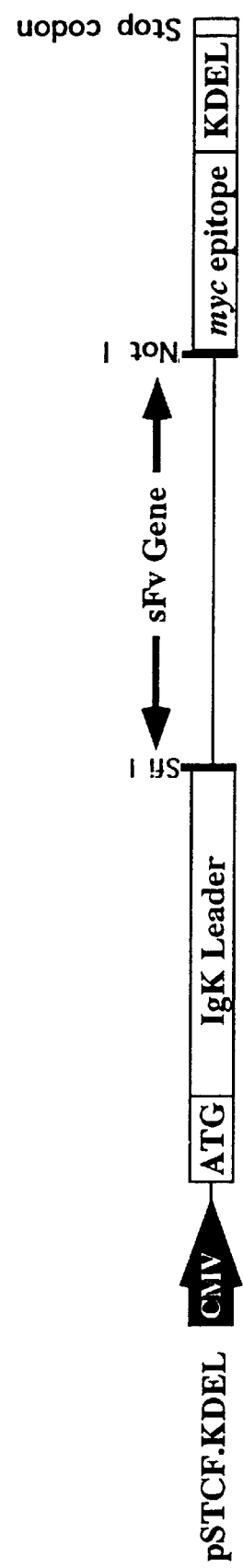
FIG. 14A
FIG. 14B

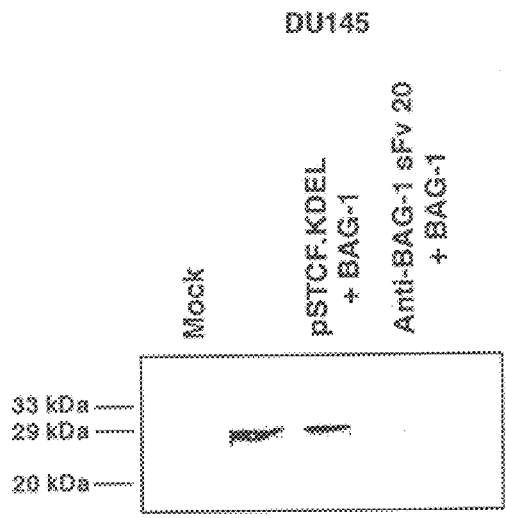
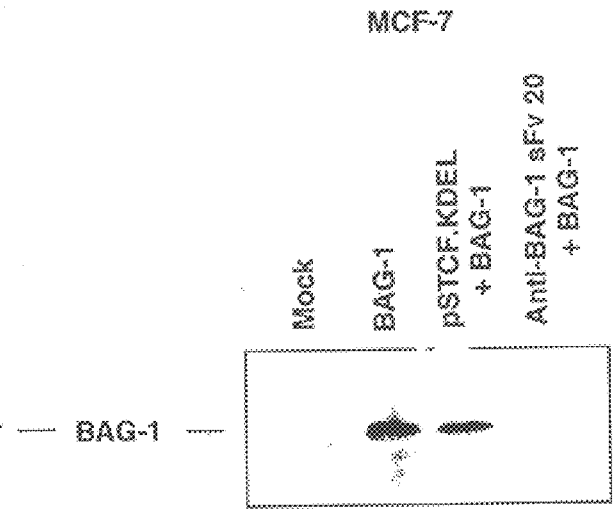
FIG. 26A  FIG. 26B
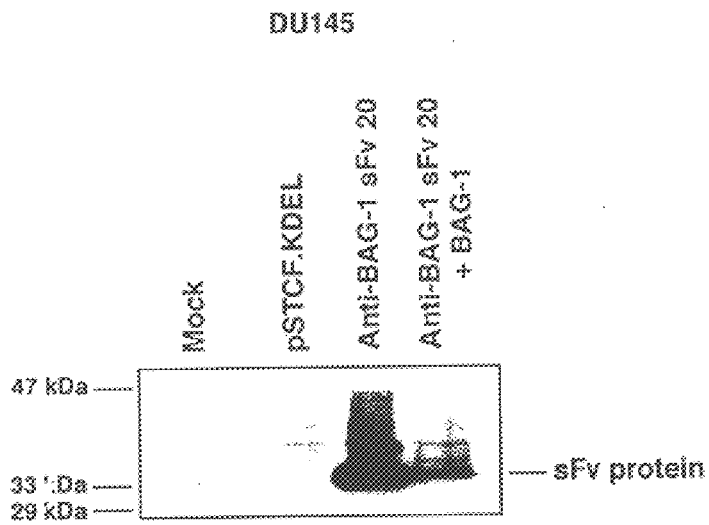
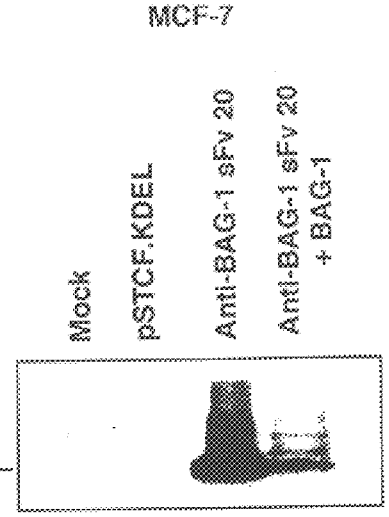
FIG. 26C  FIG. 26D

ENHANCEMENT OF TUMOR CELL RADIOSENSITIVITY USING SINGLE CHAIN INTRACELLULAR ANTIBODIES

CROSS REFERENCE TO RELATED APPLICATION

The present application claims priority to provisional application U.S. Ser. No. 60/029,673, filed Oct. 30, 1996, now abandoned.

BACKGROUND OF THE INVENTION

1. Field of the Invention

The present invention relates generally to the fields of immunology and protein chemistry. More specifically, the present invention relates to a enhancement of tumor cell chemosensitivity and radiosensitivity using single chain intracellular antibodies.

2. Description of the Related Art

Ovarian carcinoma is the leading cause of death from gynecologic cancer in the United States. Approximately 26,600 new cases were estimated to occur in 1995, resulting in 14,500 deaths from this disease. This figure exceeds the number of deaths from all other gynecologic malignancies combined. Over 70% of the patients present with late stage disease, the majority of which cannot be completely resected at the time of initial surgery. Chemotherapy has become the primary adjunct to surgery in obtaining a clinical remission or enhanced disease free survival in ovarian cancer patients. Although response to initial chemotherapy in ovarian cancer patients approaches 70%, most are transient and approximately 80% of patients (particularly those with advanced stage disease) will recur and eventually die of disease. Although a variety of salvage agents and strategies have been investigated, few have demonstrated long term effectiveness. In this regard, the five-year survival of patients with stage III disease remains, 15% to 30%.

Various approaches have been developed to accomplish gene therapy for cancer. There is increasing recognition that cancer results from a series of accumulated, acquired genetic lesions. To an ever larger extent, the genetic lesions associated with malignant transformation and progression are being identified. The recognition and definition of, the molecular basis of carcinogenesis makes it rational to consider genetic approaches to therapy. In this regard, a number of strategies have been developed to accomplish cancer gene therapy. These approaches include: 1) mutation compensation; 2) molecular chemotherapy; and 3) genetic immunopotentiation. For mutation compensation, gene therapy techniques are designed to rectify the molecular lesions in the cell having undergone malignant transformation. For molecular chemotherapy, methods have been developed to achieve selective delivery or expression of a toxin gene in cancer cells to achieve their eradication. Genetic immunopotentiation strategies attempt to achieve active immunization against tumor-associated antigens by gene transfer methodologies. Whereas the biology of each malignant disease target will likely dictate the approach taken, the majority of clinical gene therapy trials involve the genetic immunopotentiation approach. For most tumor types, however, the absence of clinical evidence of an anti-tumor effect has suggested the need for alternative approaches.

In addition to the gene therapy strategies discussed above, several reports have suggested that gene transfer approaches may be adjunctive to conventional chemotherapeutic modalities. In this regard, methods to enhance tumor cell conversion of cytotoxic prodrugs to their active forms have been developed. These include methods to enhance tumor cell metabolism of standard anti-tumor agents, such as oxazaphosphorines, by tumor cell transduction with cytochrome P-450. In another approach, transfer of viral or prokaryotic genes, such as the herpes simplex virus thymidine kinase (HSVTK), and $E.$ $coli$ cytosine deaminase are employed to sensitize tumor cells to the prodrugs ganciclovir or 5-fluorucytosine (5-FC), respectively, by conversion to toxic metabolites. In addition to these strategies, methods have been proposed based upon specifically reverting the molecular basis of the drug-resistant phenotype. This approach is based upon the concept that tumor cell drug resistance may be the result of diverse genetic alterations. These include mutational changes that lead to modifications in the structure of level of topoisomerase, to increased detoxification reactions, or to interference with the delivery of cytotoxic drug to intracellular targets. In addition, alterations affecting the regulation of the cell cycle and apoptosis are highly associated with drug resistance. These include inactivation of tumor suppressor genes, in particular p53 and Rb, and overexpression of proto-oncogenes such as those belonging to the myc family. Thus, based upon an understanding of the molecular basis of drug resistance, gene therapy strategies have been proposed to correct the genetic lesions etiologic of the drug resistant phenotype. To this end, augmentation of deficient tumor suppressor gene functions can restore tumor cell chemosensitivity. Roth et al. have shown that p53 gene replacement can enhance lung cancer chemosensitivity to cisplatin (CDDP). These studies establish the concept that gene transfer methods may be used in conjunction with conventional chemotherapeutic agents to achieve a synergistic antitumor effect. It is further suggested that specific rectification of the tumor cells genetic lesions can restore chemosensitivity.

Gene transfer approaches may be adjunctive to conventional radiation therapy. In this regard, methods to enhance tumor cell conversion of non-cytotoxic prodrugs to their active forms have been developed. The active forms of these drugs are potential or known radiosensitizers. One approach, transfer of viral or prokaryotic genes, such as herpes simplex thymidine kinase (HSVTK), and $E.$ $coli$ cytosine deaminase are employed to sensitize tumor cells to the prodrugs ganciclovir or 5-fluorocytosine (5-FC), respectively, by conversion to toxic metabolites. Both of these systems have also been employed to demonstrate enhanced radiation sensitivity. An alternative employed to enhance radiosensitivity in tumors involves the use of radiation inducible promoters to control gene expression. The tumor necrosis factor-$\alpha$ (TNF$\alpha$) gene under the control of the early growth response-1 (egr-1) promoter, was used to show radiosensitization in vitro and in vivo. In addition, to these strategies, methods have been proposed based upon specifically reverting the molecular basis of the radiation resistant phenotype. Alterations affecting the regulation of the cell cycle and apoptosis are highly associated with radiation resistance or sensitization. These alterations include inactivation of tumor suppressor genes, in particular p53 and Rb, and overexpression of proto-oncogenes such as those belonging to the ras and myc families, although this is not universal. Inactivating DNA DSB repair genes could be an effective method to dramatically increase the radiosensitivity of human tumor cell lines. Thus, based upon an understanding of the molecular basis of radiation sensitivity/resistance, gene therapy strategies may provide novel mechanisms to enhance radiation efficacy.

The erbB-2 oncogene is important to the malignant transformation of selected neoplasms including ovarian carcinomas. ErbB-2 is a 185 kDa transmembrane protein kinase receptor with homology to the family of epithelial growth factor receptors. Aberrant expression of the erbB-2 gene may play a role in neoplastic transformation and progression. Specifically, ectopic expression of erbB-2 is capable of transforming rodent fibroblasts in vitro. In addition, transgenic mice carrying either normal or mutant erbB-2 develop a variety of tumors, including neoplasms of mammary origin. Importantly, it has been shown that amplification and/or overexpression of the erbB-2 gene occurs in a variety of human epithelial carcinomas, including malignancies of the ovary, breast, gastrointestinal tract, salivary gland, and lung. In the context of ovarian carcinoma, a direct correlation has been noted between overexpression of erbB-2 and aggressive tumor growth with reduced overall patient survival. As erbB-2 overexpression may be a key event in malignant transformation and progression, strategies to ablate its expression would be therapeutic.

Overexpression of erbB-2 is associated with tumor cell chemoresistance. In addition to its direct role in neoplastic conversion, erbB-2 overexpression is associated with tumor cell resistance to chemotherapeutic agents. In this regard, heterologous overexpression of human erbB-2 accomplished by genetic transduction has been shown to increase the chemoresistance of murine fibroblasts and human lung carcinoma cells to a variety of chemotherapeutic agents. These findings are corroborated by the clinical observation that erbB-2 overexpressing tumors possess a higher intrinsic chemoresistance and thus are associated with a shorter relapse-free interval. Another line of evidence supporting the role of erbB-2 in modulating tumor cell chemoresistance is the observed therapeutic synergy between cisplatin and anti-erbB-2 monoclonal antibodies. These studies have documented that anti-erbB-2 antibodies capable of down-regulating the erbB-2 oncoprotein achieve enhanced tumor cell sensitivity to this chemotherapeutic agent. Thus, the erbB-2 oncoprotein plays a key role in determining tumor cell chemoresistance.

Therapeutic strategies for cancer have been developed which target the erbB-2 gene product. The association of overexpression of the erbB-2 gene product with neoplastic transformation and chemoresistance has led to the development of therapeutic strategies to down modulate erbB-2 levels in target tumor cells. Specifically, monoclonal antibodies (mAbs) have been developed which exhibit high affinity binding to the extracellular domains of the erbB-2 protein. A number of studies have demonstrated that a subset of these mAbs can elicit growth inhibition of erbB-2-overexpressing tumor cells, both in vitro and in vivo. In addition, a subset of these antibodies, which accomplish erbB-2 down-regulation enhance tumor cell chemosensitivity.

Gene therapy methods have been proposed to target erbB-2 overexpressing tumor cells to achieve down modulation of the oncoprotein. These approaches have included antisense strategies targeted to the transcriptional and post-transcriptional levels of gene expression. In the former instance, triplex-forming oligonucleotides binding the erbB-2 promoter region inhibit transcription of the erbB-2 gene. In addition, antisense oligonucleotides targeted to the erbB-2 transcript have accomplished phenotypic alterations in erbB-2 overexpressing tumor cells including down-regulation of cell surface expression and inhibition of proliferation.

Alternative methods to achieve targeted knockout of erbB-2 have been developed. In this regard, techniques have been developed to allow the derivation of recombinant molecules which possess antigen binding specificities expropriated from immunoglobulins. In this regard, single-chain immunoglobulin (sFv) molecules retain the antigen-binding specificity of the immunoglobulin from which they are derived, however, they lack other functional domains characterizing the parent molecule.

The Bcl-2-related protein family is an important regulator of programmed cell death or apoptosis. Members of this family with death antagonist properties include Bcl-2, Bcl-X, Bcl-w, Bfl-1, Brag-1, Mcl-1 and A1. Most of these proteins have to localize to the mitochondria to regulate apoptosis. Importantly, overexpression of death antagonist genes from the Bcl-2 family have been shown to protect a variety of cell lines from apoptosis induced by anti-cancer drugs. The Bcl-2 gene encodes a 26 kD protein that regulates apoptosis, at least in part, via its interaction with other members of the Bcl-2 family. Bcl-2 is mainly localized as an integral mitochondrial membrane protein, although Bcl-2 is also found to be associated with other membranes, including those of the endoplasmic reticulum (ER) and the nucleus. Extensive experimental evidence suggests that Bcl-2 promotes cell survival by preventing the onset of apoptosis induced by a wide variety of stimuli, including essentially all classes of anticancer drugs and x-irradiation. A role for Bcl-2 in cancer was initially identified in follicular lymphoma bearing the chromosomal translocation t(14;18) that juxtaposes the Bcl-2 gene with the immunoglobulin heavy chain locus, thereby up-regulating its expression.

Though first described in lymphoma, overexpression of Bcl-2 is also found in a number of non-hemopoietic cancers, including prostate cancer, breast cancer, and glioblastoma. In these cells, Bcl-2 may play an important role in protecting cancer cells from death induced by anti-cancer drugs. Estrogen-induced increases in Bcl-2 in the context of an estrogen-responsive human breast cancer cell line significantly enhanced their resistance to apoptosis, whereas anti-sense mediated reduction in Bcl-2 increased their sensitivity to anticancer drugs. Taxol-mediated inactivation of Bcl-2 by phosphorylation in prostate cancer cell lines renders them susceptible to apoptosis. Furthermore, Bcl-2 expression in ovarian cancer cells affects the cellular response to apoptosis and modulates their resistance to anti-cancer drugs. In addition to solid tumors, many non-Hodgkin lymphomas (NHL) and some acute myeloid leukemias (AMLs) often overexpress Bcl-2. Clinical studies of these hematological malignancies suggest an association between Bcl-2 expression, resistance to apoptosis, poor response to chemotherapy and shorter patient survival. Taken together, these results suggest a central role for Bcl-2 in the promotion of cell survival in solid and hematopoietic tumors.

Based upon these concepts, molecular therapeutic strategies to modulate Bcl-2 expression have been proposed. In this regard, antisense (AS) oligonucleotides targeted against Bcl-2 mRNA sequences and plasmid derived Bcl-2 AS transcripts have been shown to alter the growth and survival of lymphoid cells overexpressing Bcl-2 in vitro . In this context, several independent Bcl-2 AS studies have demonstrated a significant increase in apoptosis in treated cells, as well as more effective tumor cell killing following exposure to chemotherapeutic drugs. In vivo models have extended these findings, demonstrating that pre-treatment of lymphoma cells bearing the t(14;18) translocation with AS oligonucleotides to Bcl-2 mRNA inhibited the formation of tumors in a SCID mouse model. More recently, a clinical trial using Bcl-2 AS therapy in patients with NHL provided the first evidence of down-regulation of the Bcl-2 protein in humans.

BAG-1, a newly described Bcl-2 binding protein, functions in concert with Bcl-2 to prolong cell survival. In a human lymphoid cell line, gene transfer experiments have shown that coexpression of BAG-1 and Bcl-2 markedly enhanced protection from apoptosis induced by a variety of stimuli compared to cells transduced with either BAG-1 or Bcl-2 alone. In addition, overexpression of BAG-1 in liver progenitor cells increased hepatocyte growth factor (HGF)- and platelet-derived growth factor (PDGF)-induced protection from apoptosis. Thus, BAG-1 acts as a cell death inhibitor. Although the predicted amino-acid sequence of BAG-1 shares no homology with other proteins of the Bcl-2 family, it specifically interacts with Bcl-2 and can activate Raf-1 kinase. Of note, BAG-1 lacks the Bcl-2 family transmembrane domain and thereby localizes to the cytoplasm where it can interact with the cytoplasmic domain of the HGF and PDGF receptors. Despite these findings, the precise role of BAG-1 remains unclear, but the fact that it is expressed ubiquitously, and that it acts in conjunction with different growth factor receptors in preventing apoptosis, suggest that BAG-1 can function as a common adaptor protein between tyrosine kinase receptors and the anti-apoptotic machinery of the cell.

The prior art is deficient in the lack of effective means of enhancing tumor cell chemosensitivity to cancer drugs and enhancing sensitivity to radiation. The present invention fulfills this longstanding need and desire in the art.

SUMMARY OF THE INVENTION

In one embodiment of the present invention, there is provided a method of enhancing the chemosensitivity and radiosensitivity of a neoplastic cell, comprising the step of: introducing into the cell an antibody homologue, wherein the antibody homologue is expressed intracellularly and binds to a target protein intracellularly.

In another embodiment of the present invention, there is provided a method of enhancing the radiosensitivity of a neoplastic cell, comprising introducing into the cell a nucleic acid molecule encoding an antibody homologue, wherein the antibody homologue is expressed intracellularly and binds to the oncoprotein intracellularly in the endoplasmic reticulum of the cell.

In another embodiment of the present invention, there is provided a method for enhancing the inhibition of proliferation of a neoplastic cell expressing an oncoprotein that stimulates proliferation of the cell, comprising the steps of: introducing into the cell a nucleic acid molecule encoding an antibody homologue, wherein the antibody homologue is expressed intracellularly and binds to the protein intracellularly; and contacting said cell with an anti-neoplastic agent.

In yet another embodiment of the present invention, there is provided a method of enhancing the chemosensitivity and radiosensitivity of a neoplastic cell, comprising the step of: introducing into the cell an antibody homologue, wherein the antibody homologue is expressed intracellularly and binds to a target protein intracellularly; and contacting said cell with an anti-neoplastic agent, radiation or a combination thereof.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the effect of intracellular anti-erbB-2 sFv on cell surface expression of erbB-2 protein. The human ovarian carcinoma cell line SKOV3 was transfected by the AdpL method with the described plasmid constructs and analyzed for cell surface erbB-2 at 96 hours post-transfection using an anti-human erbB-2 polyclonal antibody. Original magnification 400×.

FIG. 3 shows the determination of apoptotic DNA fragmentation induced by ER anti-erbB-2 sFv. Tumor cells were transfected with the plasmids pcDNA3, pGT20 and pGT21. At indicated time points post-transfection, cells were harvested and chromosomal DNA analyzed by gel electrophoresis.

Figure 8:
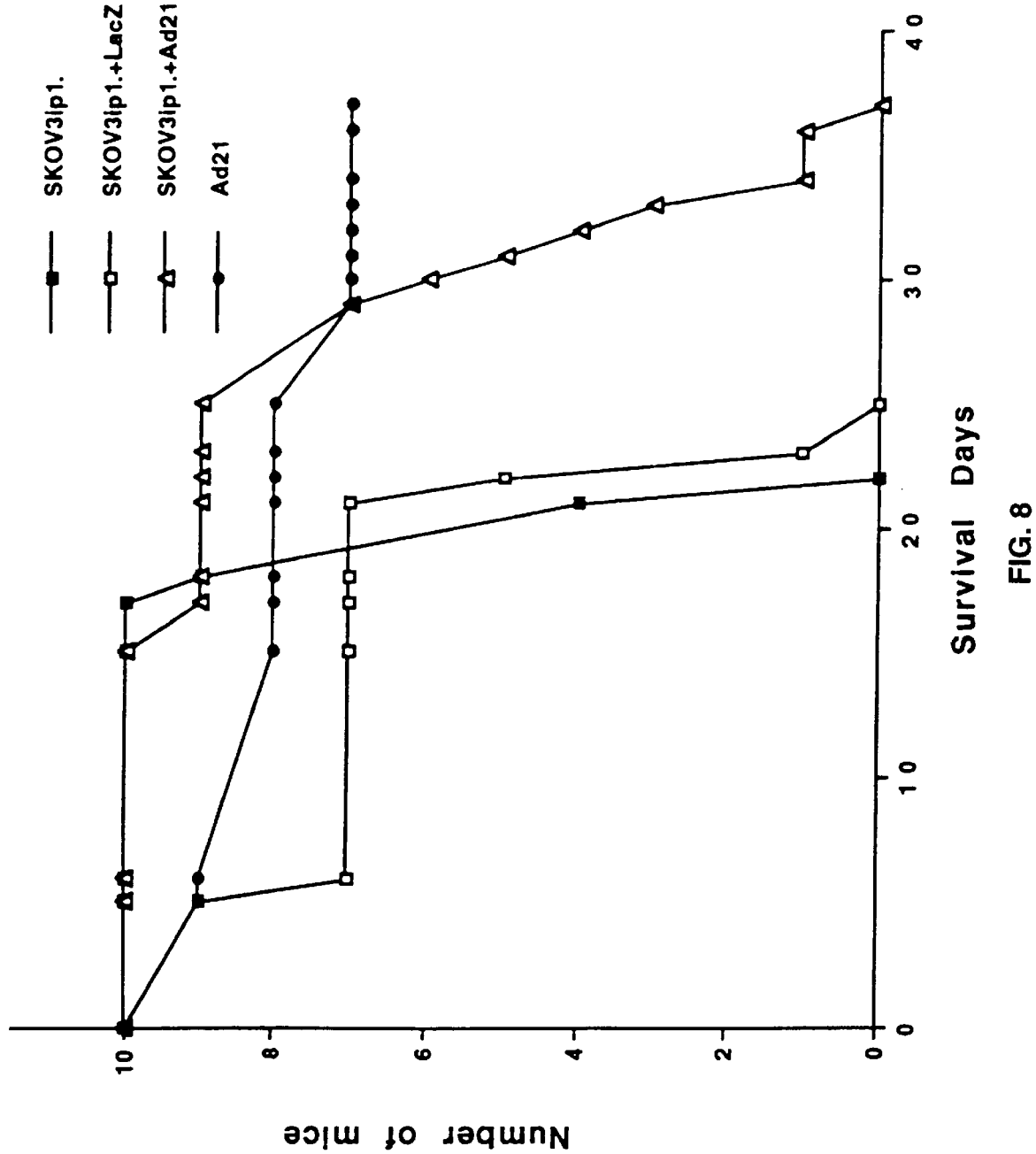

FIG. 8 shows the in vivo efficacy of the recombinant adenovirus encoding the ER form of the anti-erbB-2 sFv in prolongation of survival. ErbB-2-overexpressing human ovarian carcinoma cells SKOV3.ip1 were injected intraperitoneally into CB-17 SCID mice (n=10). 5 d later the animals were challenged with AdCMVLacZ or Ad21. Animals were monitored for survival.

Figure 9:
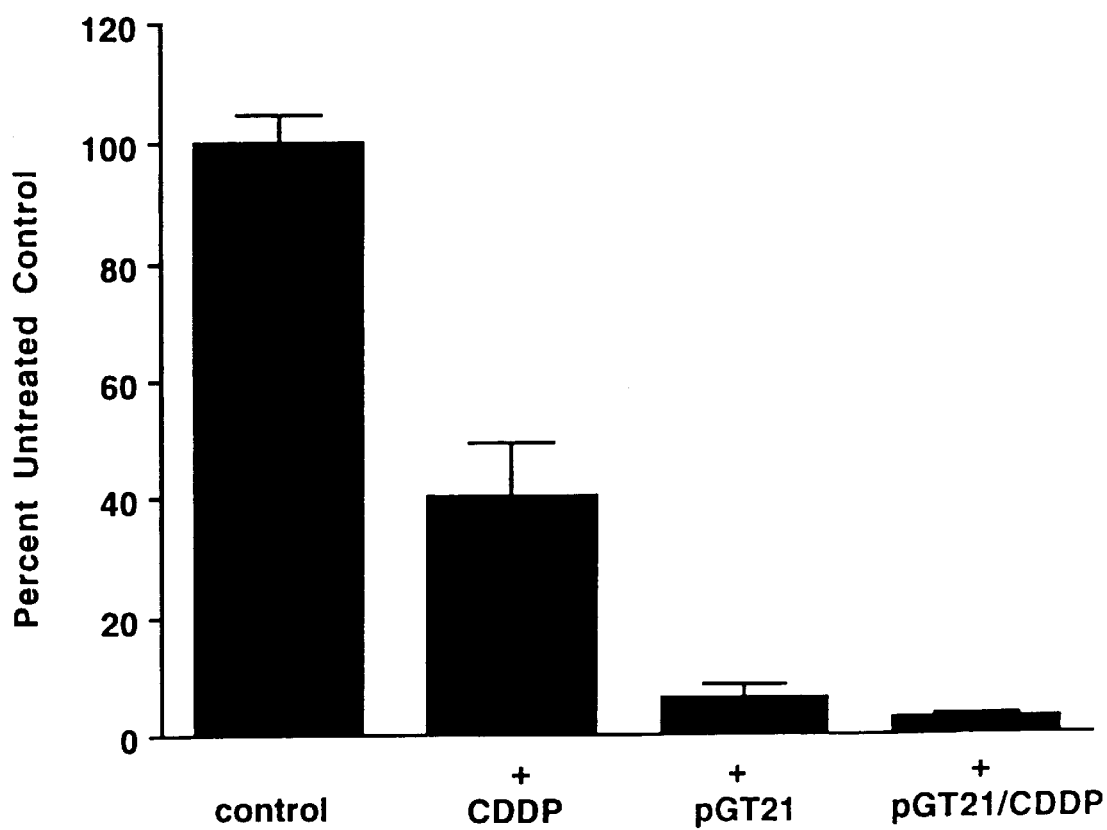

FIG. 9 shows the cytotoxic effect of an anti-erbB-2 sFv in combination with CDDP. The erbB-2 overexpressing ovarian carcinoma cell line SKOV3 was transfected with a plasmid construct encoding an ER form of an anti-erbB-2 sFv (pGT21) or a control plasmid construct (pcDNA3) and treated with CDDP (2 μg/ml). The cells were incubated for 72 hours and the number of viable cells determined by an MTS assay. Experiments were performed in triplicate and the results represent the mean±SEM.

Figure 10A:
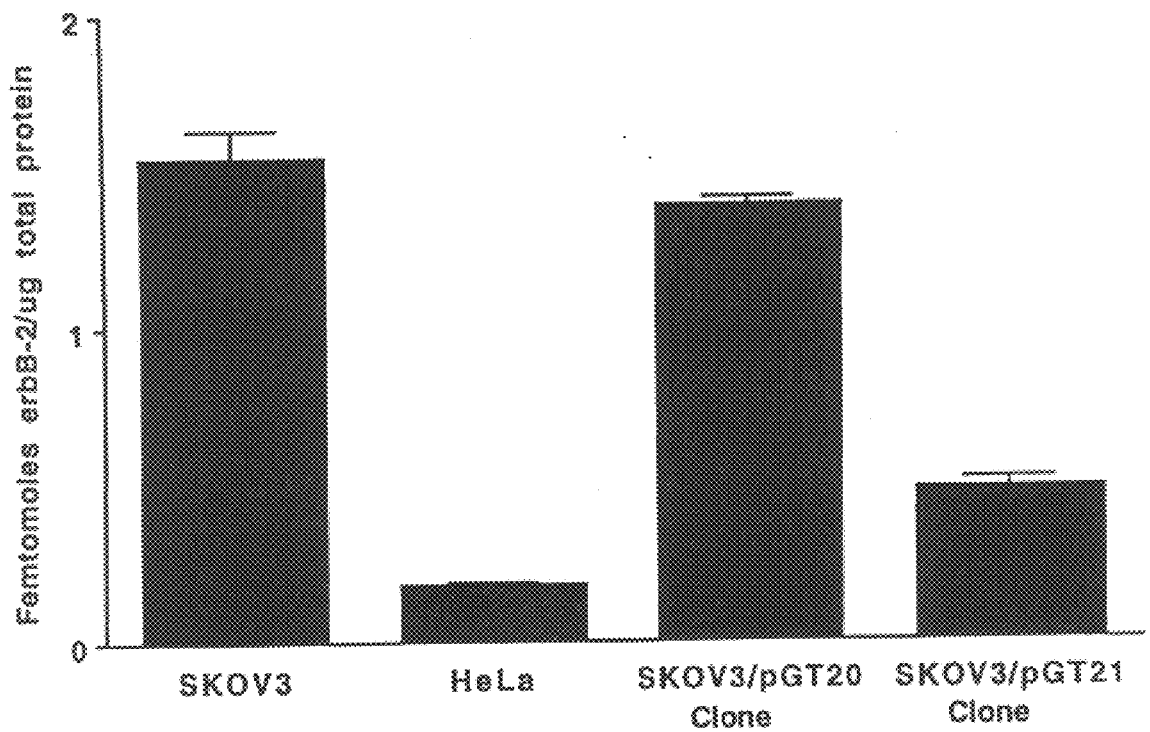
Figure 10B:
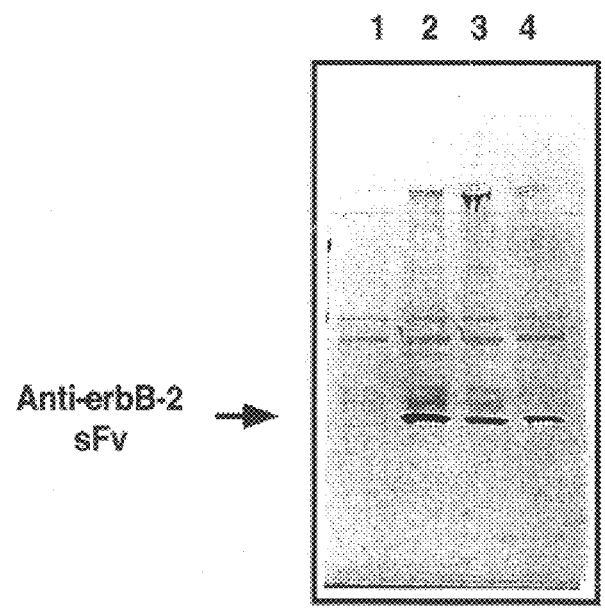

FIG. 10 shows the characterization of anti-erbB-2 sFv expressing SKOV3.ip1 clones. FIG. 10A: shows the determination of cell surface erbB-2 protein expression in stable clones as determined by an ELISA assay. Relative erbB-2 levels were calculated from a standard curve. SKOV3.ip1 cells are a positive control while HeLa, an erbB-2 negative human cervical cell line, served as a negative control. Results are expressed a mean±SEM. FIG. 10B: shows the determination of the presence of anti-erbB-2 sFv in stable clones by Western blot. Cell were solubilized and the samples electrophoresed with probe analysis using a polyclonal rabbit anti-erbB-2 sFv antibody.

Figure 11:
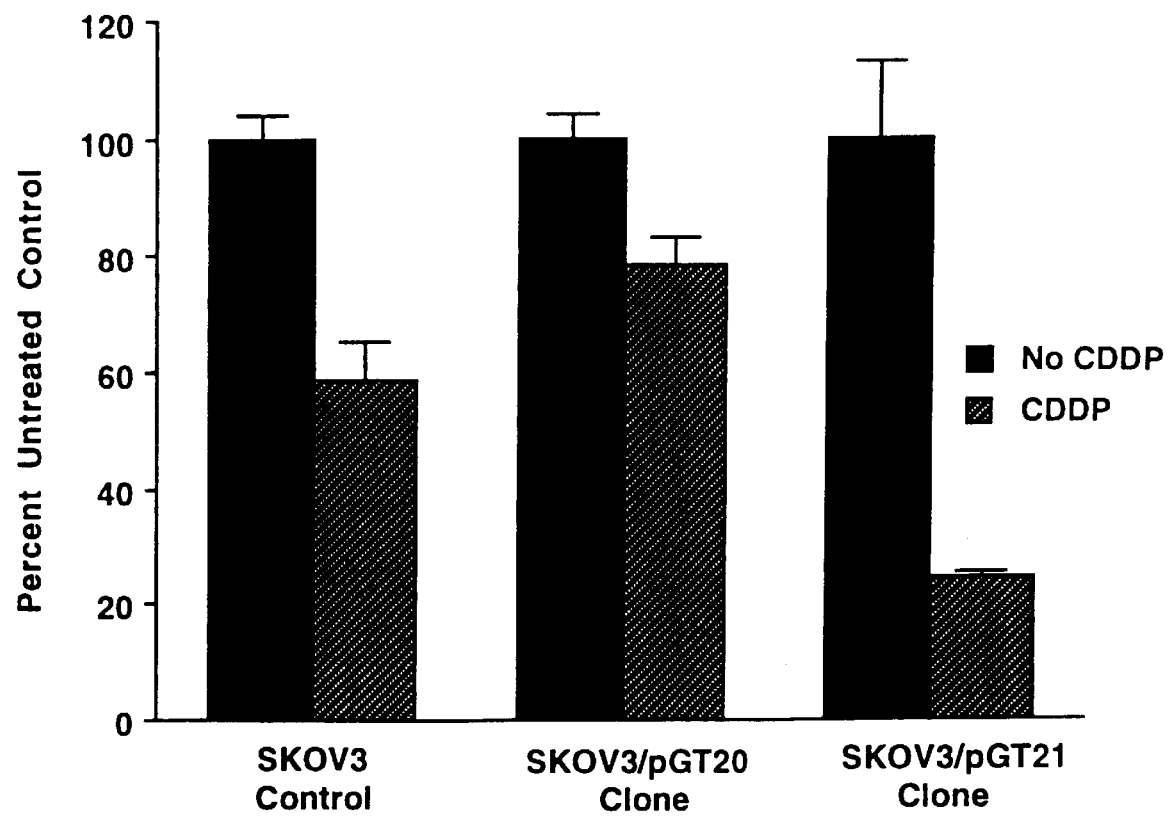

FIG. 11 shows the sensitivity of anti-erbB-2 sFv expressing SKOV3 clones to CDDP. SKOV3/pGT21 clones expressing the ER form of the anti-erbB-2 sFv demonstrate enhanced chemosensitivity to CDDP. SKOV3/pGT21 clones were treated with CDDP (2 μg/ml) and incubated for 72 hours. Cell viability was then measured using an MTS assay. SKOV3 cells and SKOV3/pGT20 clones served as controls. Experiments were performed in triplicate and the results are reported as mean±SEM.

Figure 12:
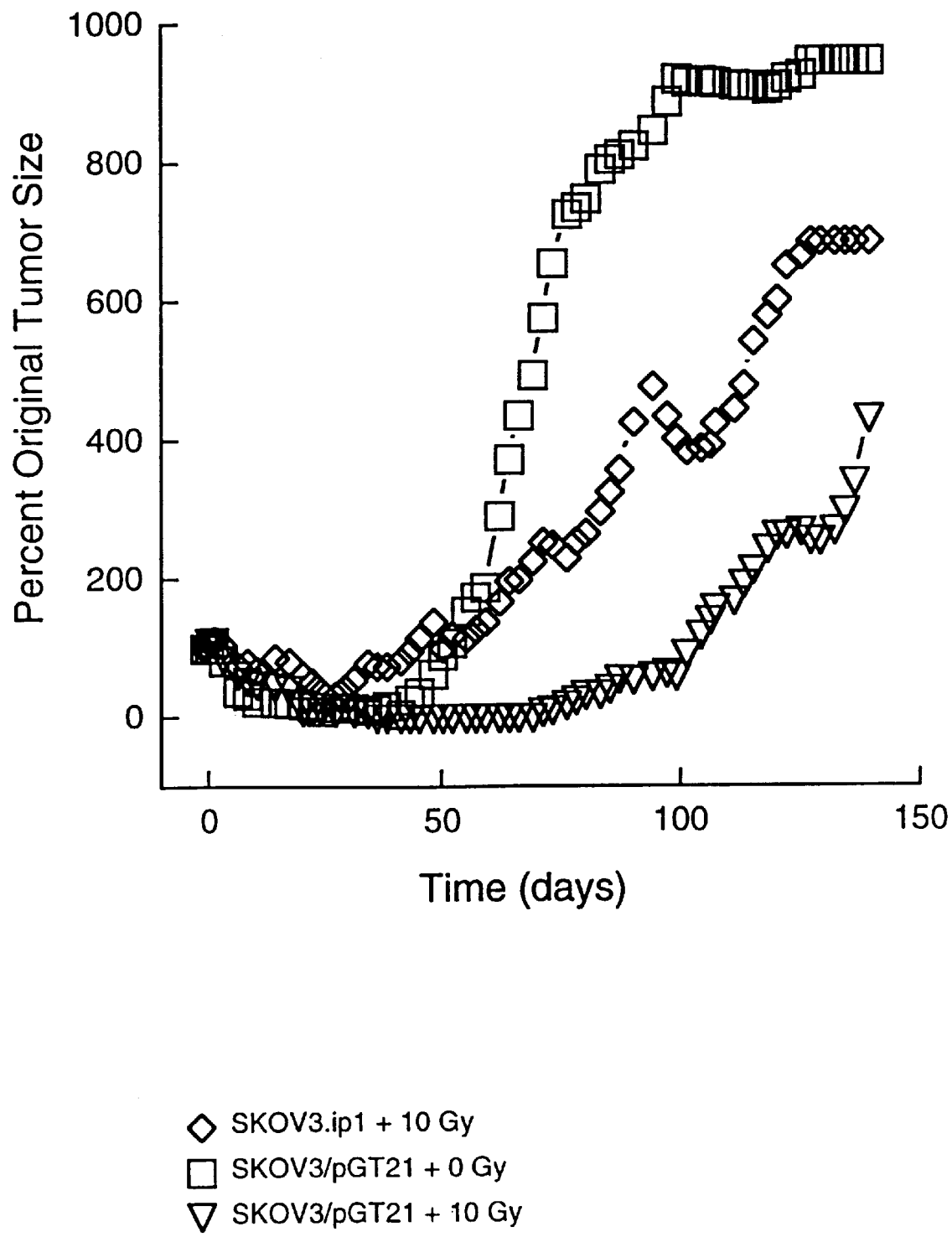

FIG. 12 shows the effect of single fraction cobalt-60 external beam irradiation on the growth of established subcutaneous human ovarian cancer xenografts of either untransfected SKOV3 or SKOV3/pGT21 cells expressing the ER form of the anti-erbB-2 sFv.

Figure 13:
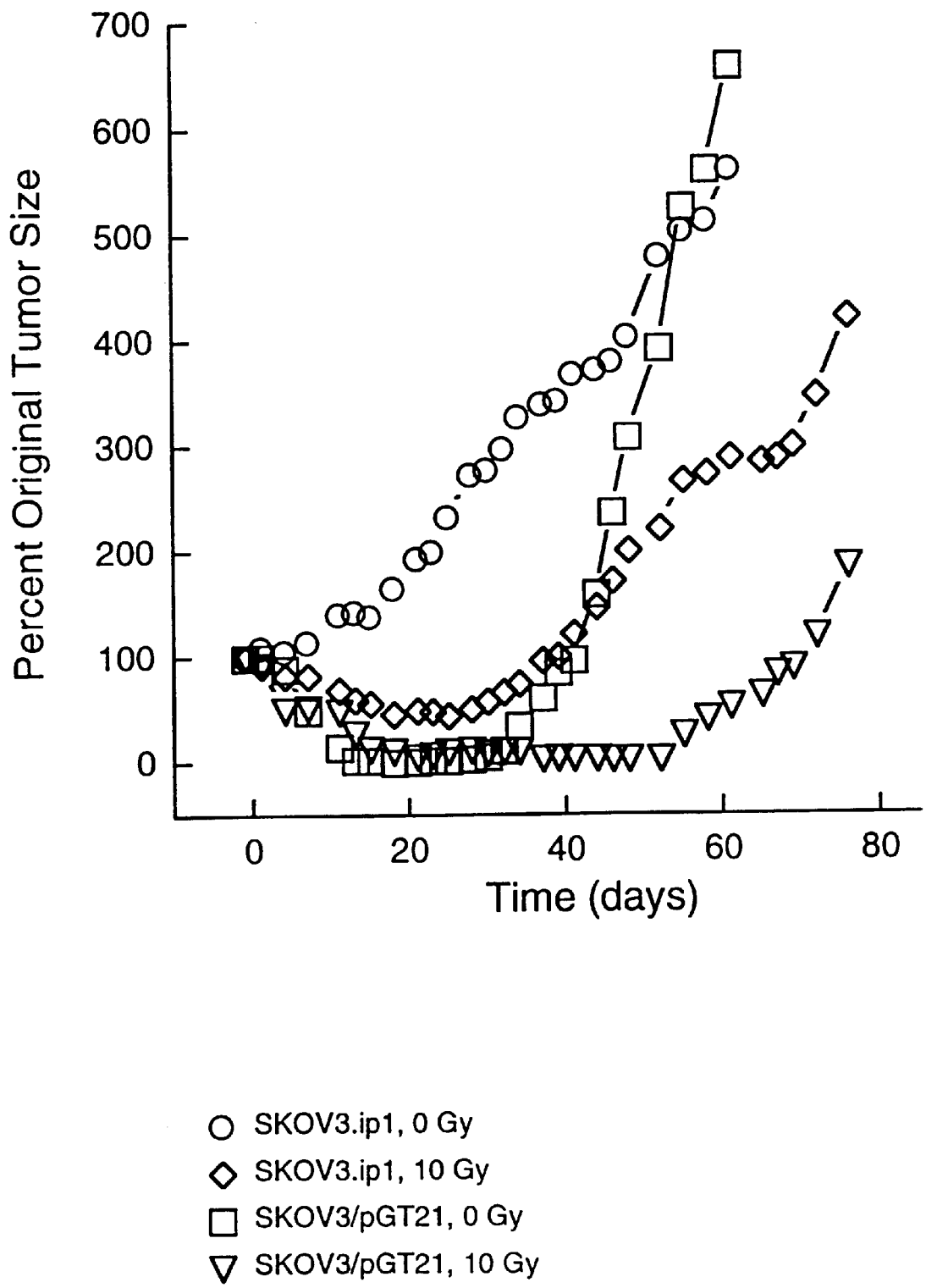

FIG. 13 shows a different experiment depicting the effect of single fraction cobalt-60 external beam irradiation on the growth of established subcutaneous human ovarian cancer xenografts of either untransfected SKOV3 or SKOV3/pGT21 cells expressing the ER form of the anti-erbB-2 sFv.

FIG. 14 shows (FIG. 14A) the schema of the pCANTAB5 vector showing control regions. The sFv cDNA (750 bp) is introduced between the SfiI and NotI sites. The g3p leader sequence directs transport of the protein to the inner membrane/periplasm of E. coli whereas the functional domain of g3p (fd3) attaches the fusion protein to the tip of the assembling phage. The sFv is expressed as a fusion protein with the E-tag peptide to allow easy detection. FIG. 14B shows the schema of the pSTCF.KDEL eukaryotic vector expressing sFv genes. Expression of the sFv protein is driven by the CMV promoter. The sFv cDNA is introduced between SfiI and NotI. The IgK leader sequence directs the sFv protein to the ER, and the KDEL signal at the c-terminus leads to retention in this cellular compartment. The sFv open reading frame is also fused with a c-myc epitope to allow easy detection by Western blot.

Figure 15A:
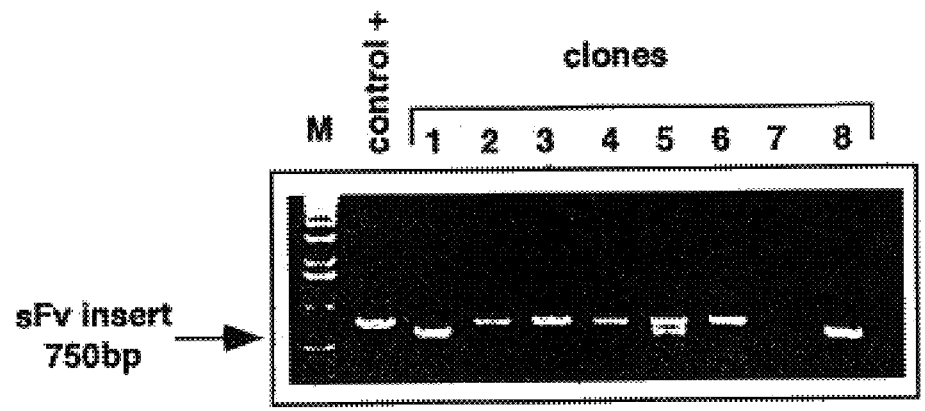

FIG. 15A shows the screening of positive clones for sFv inserts obtained after the colony lift selection. The plasmid DNA was extracted from positive clones and used in a PCR reaction. The PCR primers were complimentary to the Sfi I and Not I sites. The resulting sFv DNA products migrate as a 750 bp fragment on an agarose gel (1%); and FIG. 15B the expression of the anti-Bcl-2 sFv in the E. coli strain HB2151. IPTG-induced periplasmic extracts were run on SDS-PAGE gel (12%). After transfer, the membrane was probed with an horseradish peroxidase labeled anti-E-tag antibody. The anti-Bcl-2 sFv protein has an apparent molecular weight of approximately 34 kDa.

Figure 16:
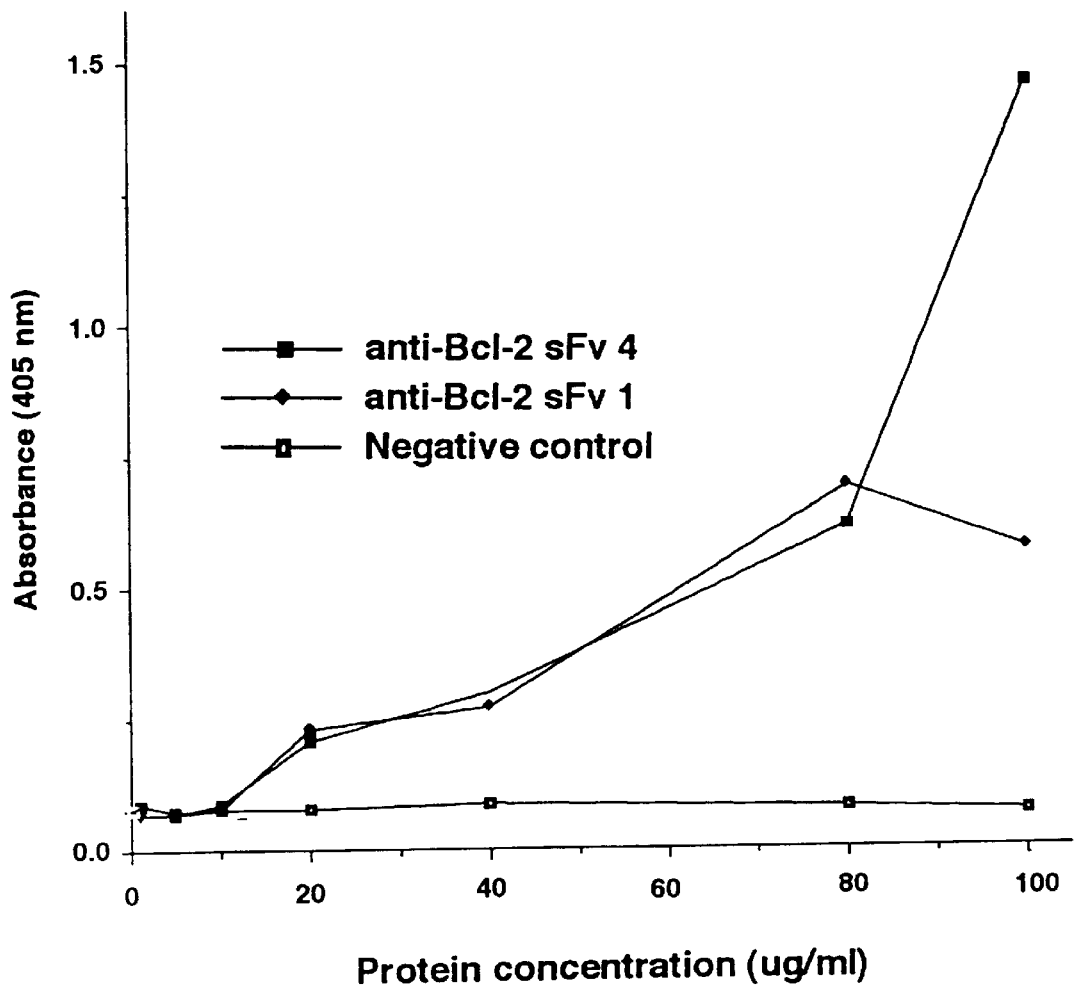

FIG. 16 shows the binding affinity of the anti-Bcl-2 sFvs to the Bcl-2 protein as measured by ELISA. Various concentrations of periplasmic extracts anti-Bcl-2 sFv 1 and 4 were added onto a 96-well plate coated with recombinant Bcl-2 protein. A periplasmic extract containing no sFv protein was used as a negative control. After addition of an HRP-conjugated mouse anti-E-tag antibody and the peroxidase substrate, the plate was read at 405 nm. Samples were done in duplicate and O.D. values are expressed as a mean.

Figure 17A:
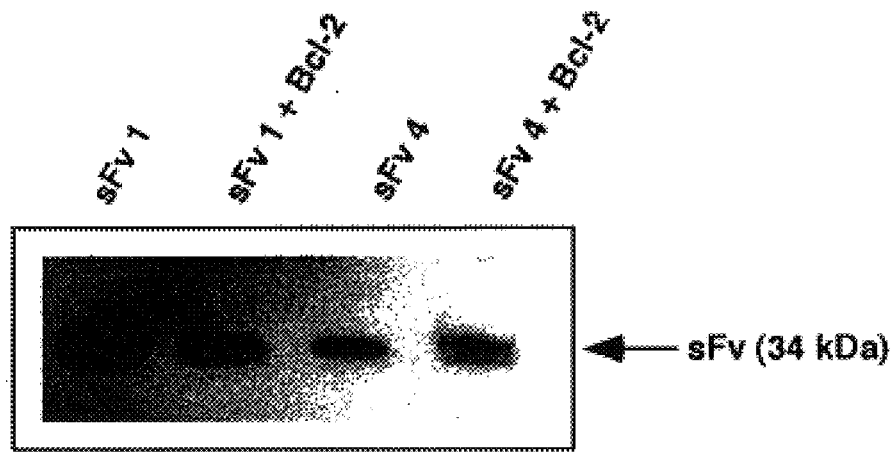
Figure 17B:
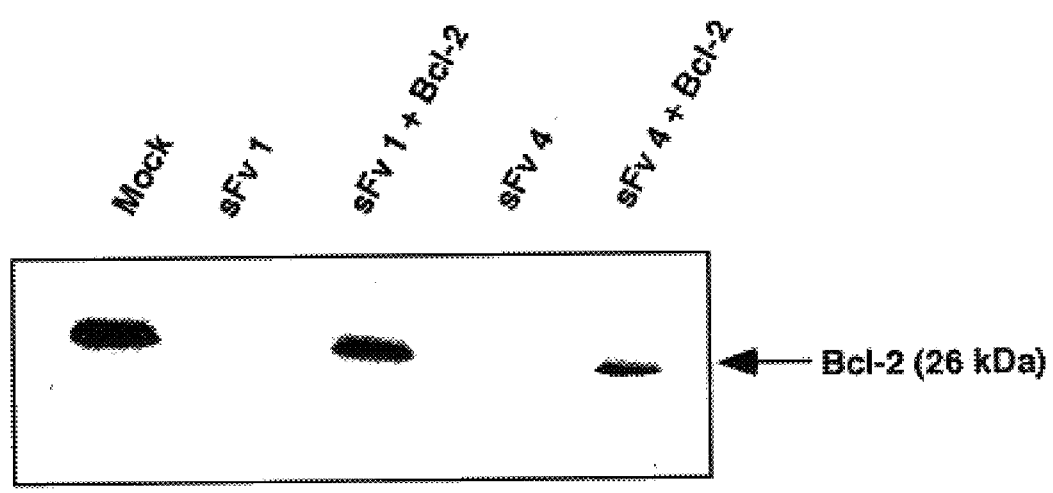

FIG. 17A shows the expression of the anti-Bcl-2 sFvs 1 and 4 in HeLa cells as determined by Western blot. Cells were transduced with either the anti-Bcl-2 sFvs 1 and 4 alone (sFv 1, sFv 4) or cotransfected with the sFv constructs and the pRC/CMV/hBcl-2 plasmid (sFv 1+Bcl-2, sFv 4+Bcl-2). In eukaryotic cells, the sFv protein migrates around 34 kDa; and FIG. 17B shows the modulation of Bcl-2 expression in HeLa cells as determined by Western blot. Mock indicates that cells were treated with AdpL only; sFv 1, sFv 1 vector only; sFvl+Bcl-2, sFv 1 vector and pRC/CMV/hBcl-2; sFv 4, sFv 4 vector only; sFv 4+Bcl-2, sFv 4 vector and pRC/CMV/hBcl-2. Equal amounts (30 μg) of total protein were loaded in each lane.

Figure 18:
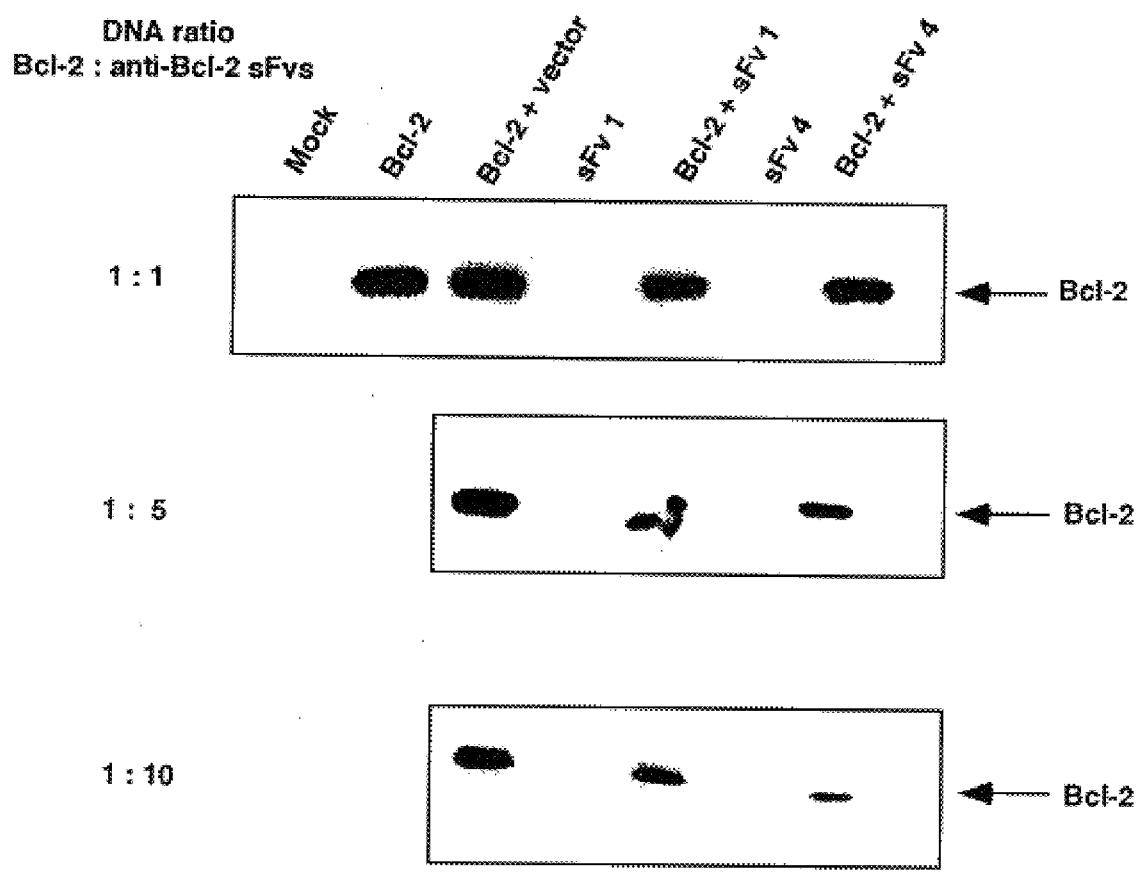

FIG. 18 shows the western blot analysis of different ratios of Bcl-2 versus anti-Bcl-2 sFv in HeLa cells. The ratios used in each experiments is indicated on the left. Equal amounts (30 μg) of total protein were loaded in each lane and separated by SDS-PAGE. The position of the Bcl-2 protein is indicated.

Figure 19A:
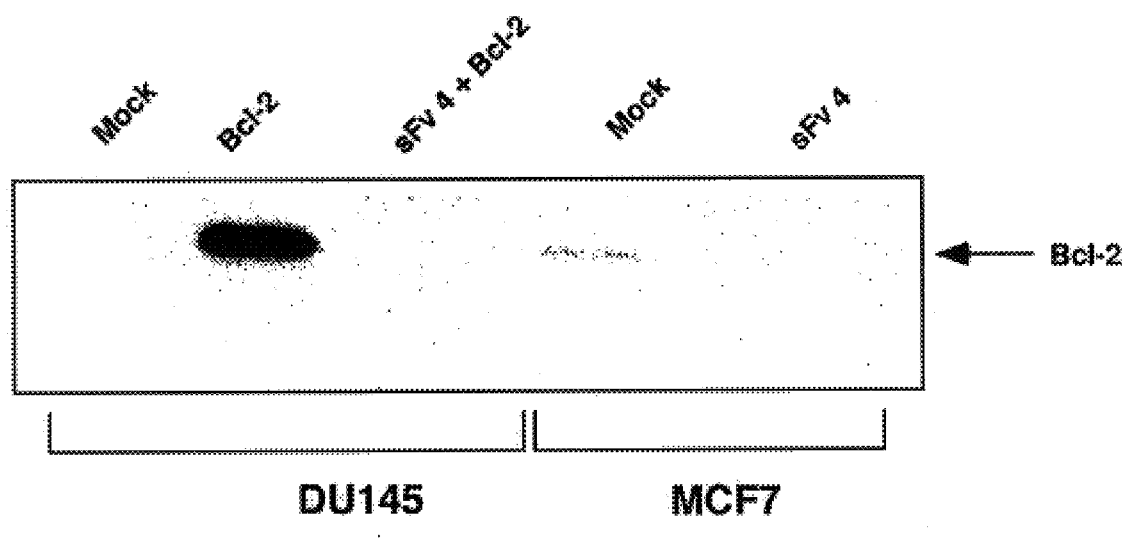
Figure 19B:
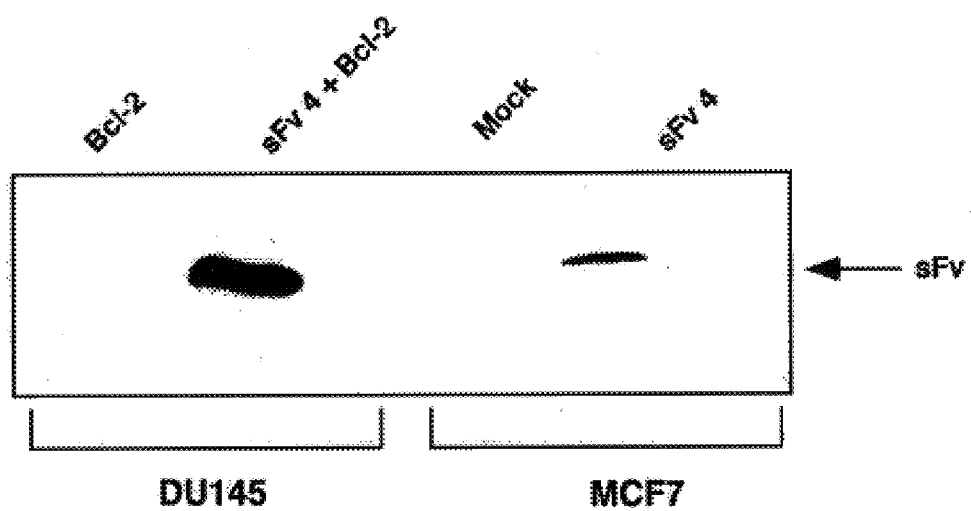

FIG. 19A shows a western blot analysis showing down-regulation of Bcl-2 expression in DU145 and MCF-7 cells. DU145 were transfected with either pRC/CMV/hBcl-2 alone (Bcl-2) or pRC/CMV/hBcl-2 plus sFv 4 vector (sFv 4+Bcl-2) at a DNA ratio of 1:10. MCF-7 cells were treated with AdpL alone (mock) or the sFv 4 vector (sFv 4). Equal amounts (25 μg) of total protein were loaded in each lane and separated by SDS-PAGE; and FIG. 19B shows the expression of the sFv 4 protein in DU145 and MCF-7 as determined by Western blot. Equal amounts (25 μg) of protein were separated by SDS-PAGE.

Figure 20A:
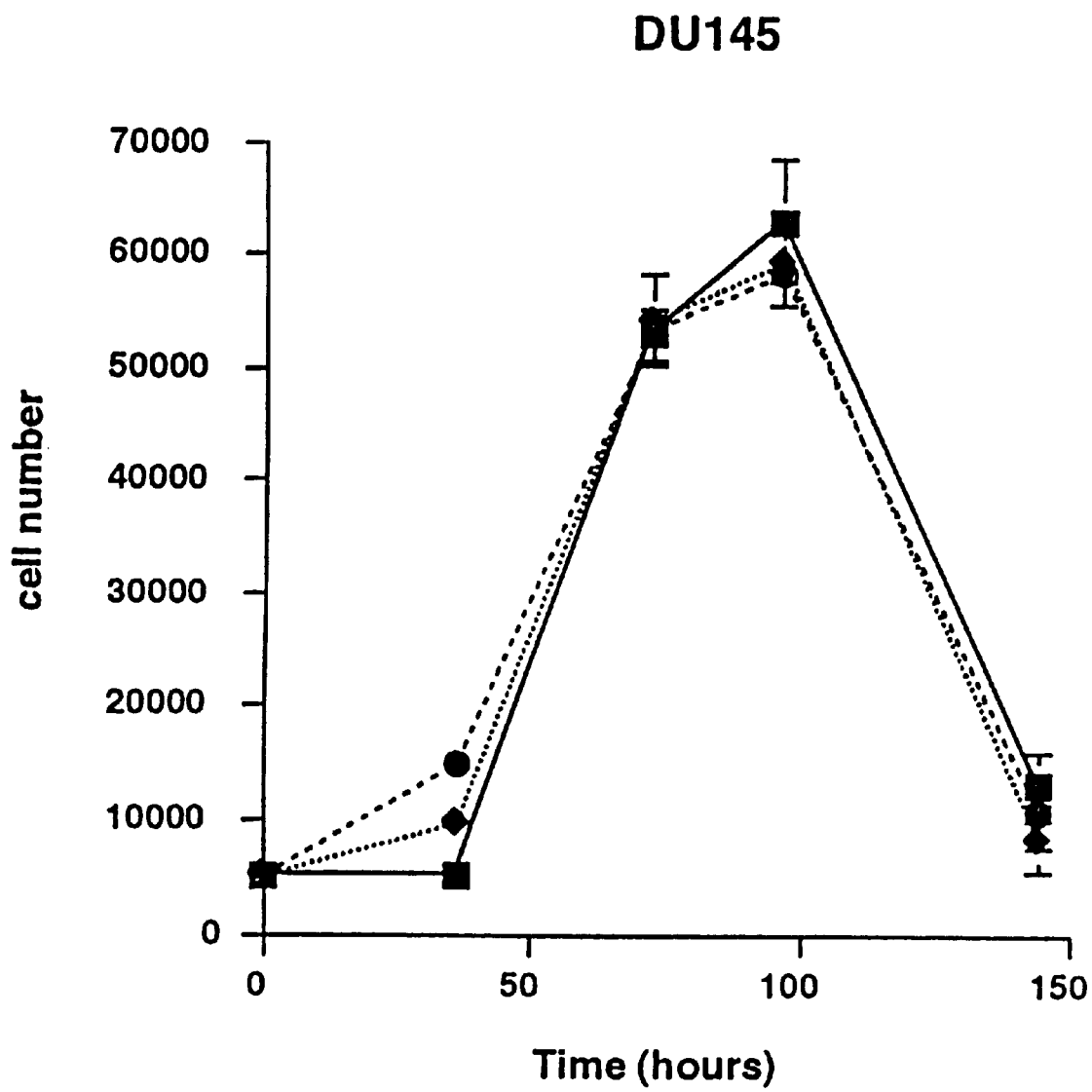
Figure 20B:
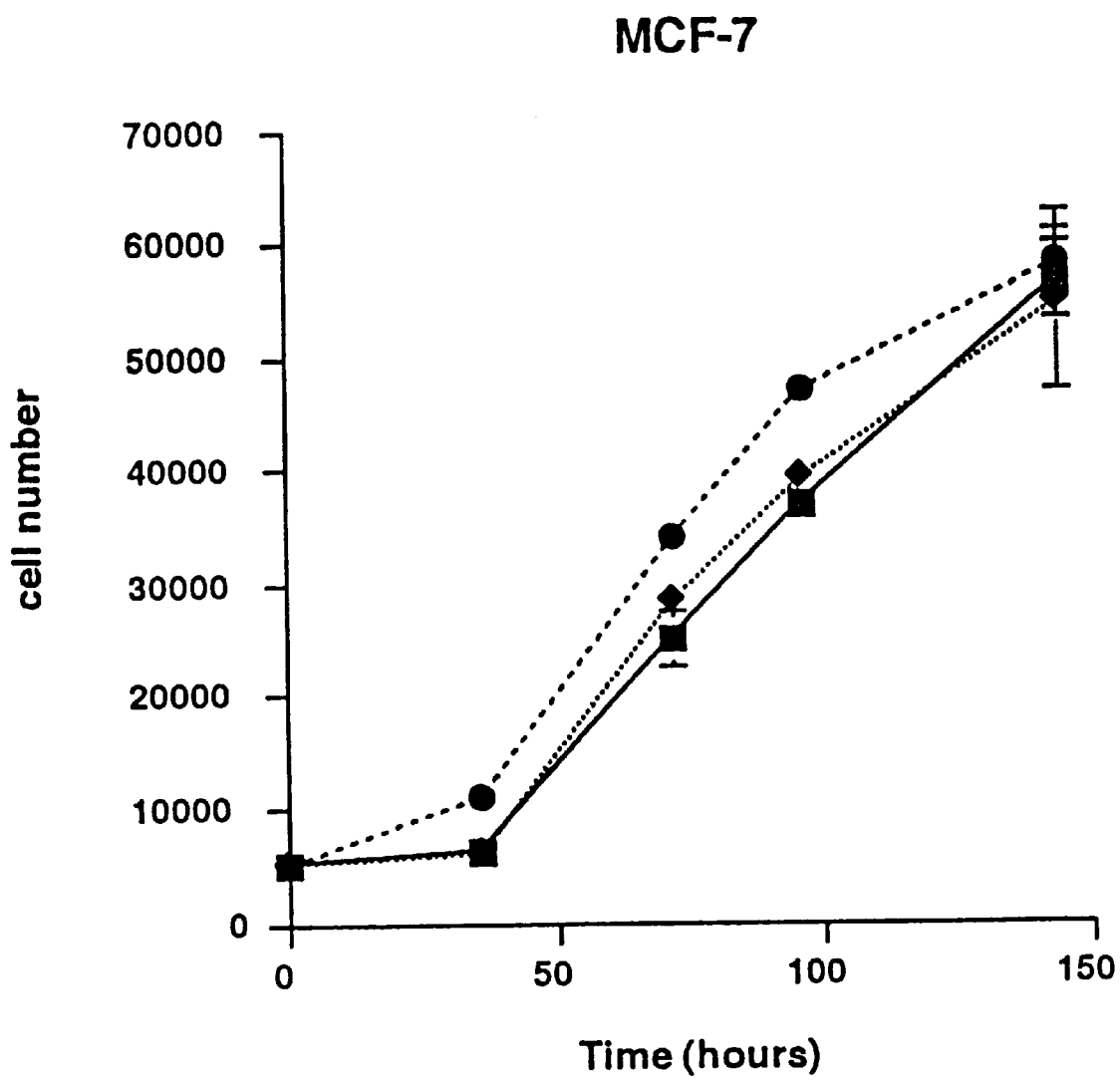

FIG. 20 shows that expression of the anti-Bcl-2 sFv 4 does not affect the growth rate of cells overexpressing or not Bcl-2. DU145 (FIG. 20A) and MCF-7 (FIG. 20B) were mock-transfected (square), transfected with the pSTCF.KDEL (diamond) or the anti-Bcl-2 sFv (circle) and followed over time. The growth rate was determined by MTT assay.

Figure 21A:
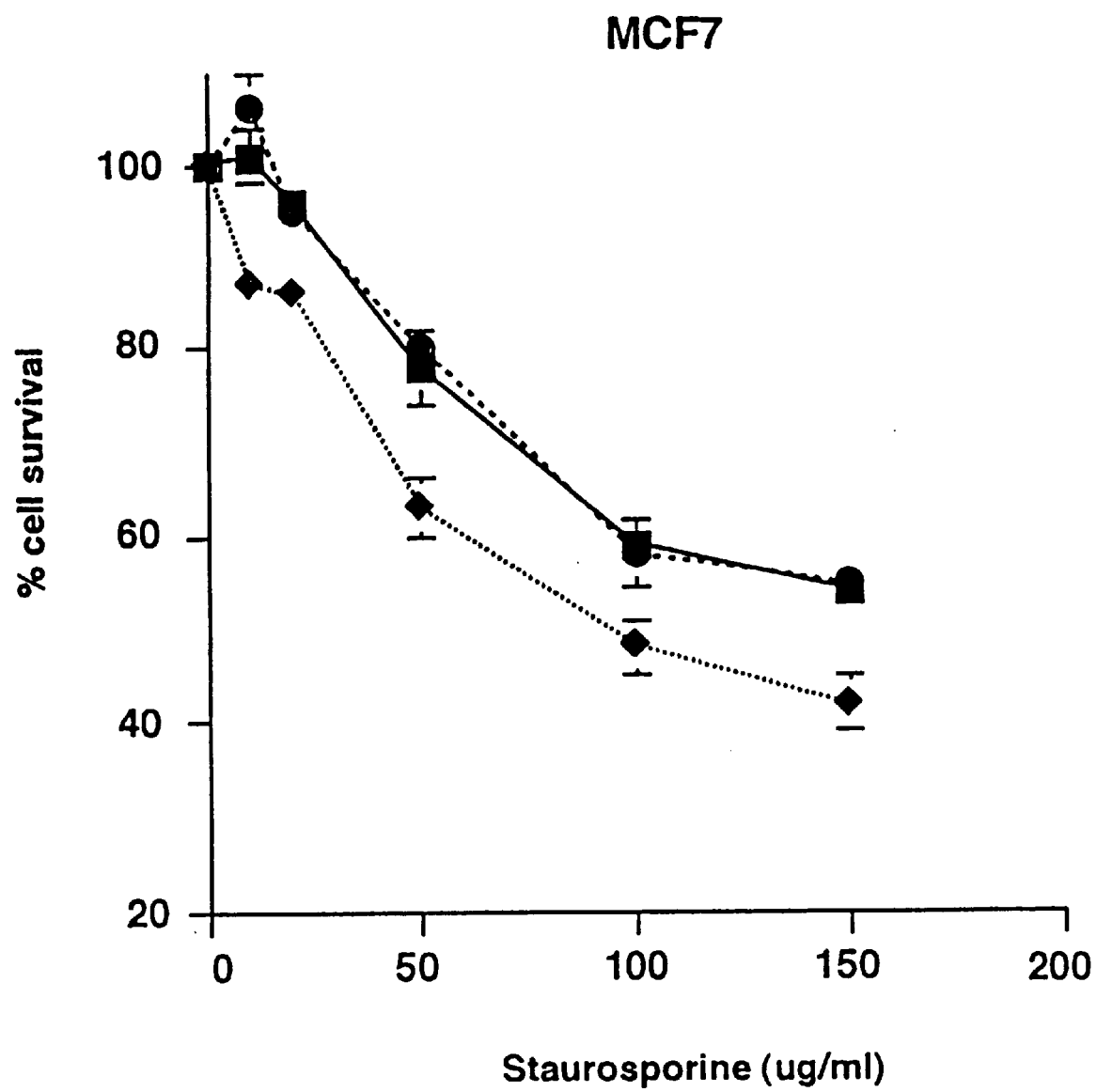
Figure 21B:
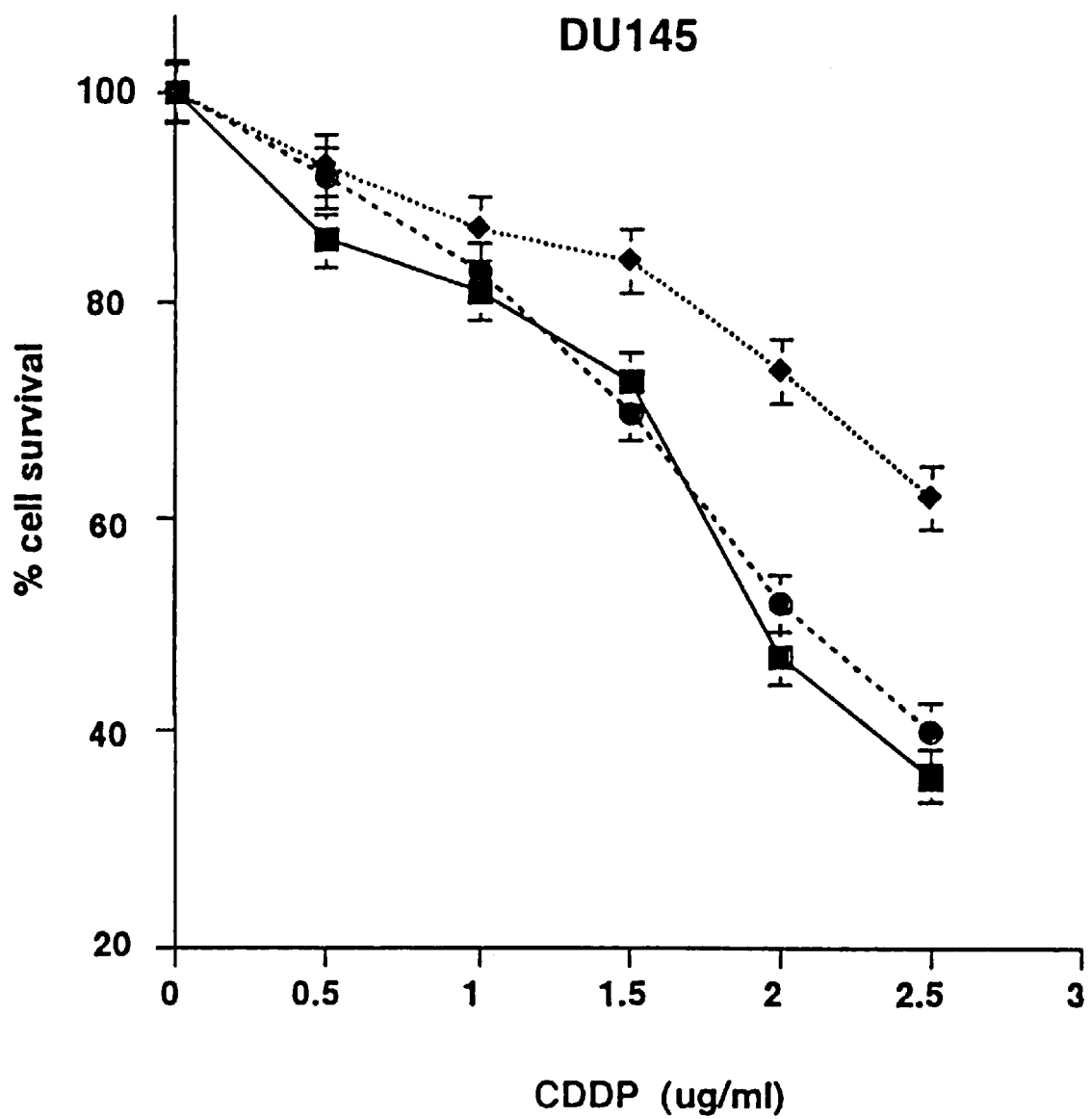

FIG. 21 shows that expression of the anti-Bcl-2 sFv 4 increases cell death in tumor cells overexpressing Bcl-2 in the presence of drugs. (FIG. 21A) DU145 cells were mock-transduced (square), transduced with pRC/CMV/hBcl-2 (diamond), or transfected with pRC/CMV/hBcl-2 plus the anti-Bcl-2 sFv 4 (circle) at a DNA ratio of 1:10 and treated with various concentrations of CDDP. (FIG. 21B) MCF-7 cells were mock-transfected (square), transfected with pSTCF.KDEL (circle) or transfected with the anti-Bcl-2 sFv 4 (diamond) and treated with various concentration of staurosporine. Cell survival was determined by MTT assay at 4 days.

Figures 22A, 22B:
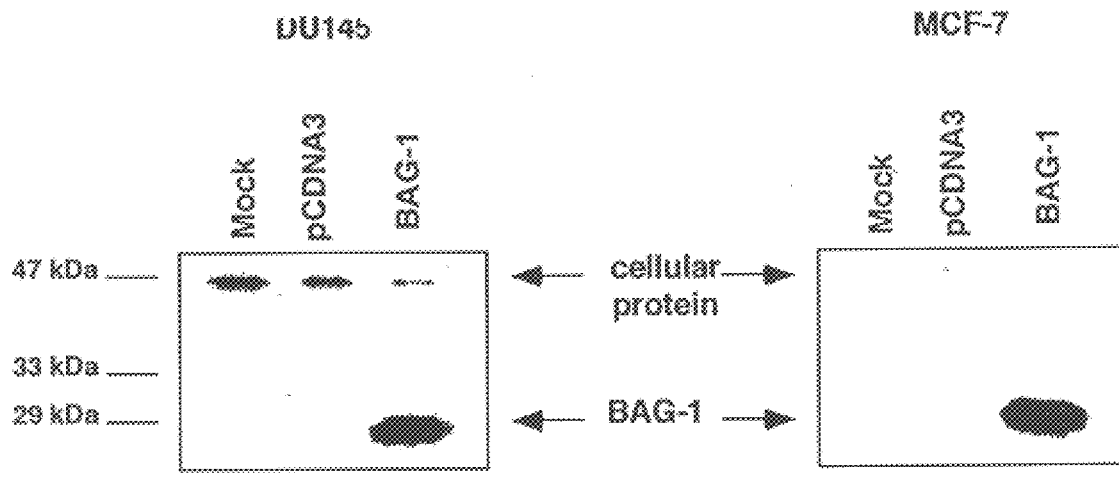
Figures 22C, 22D:
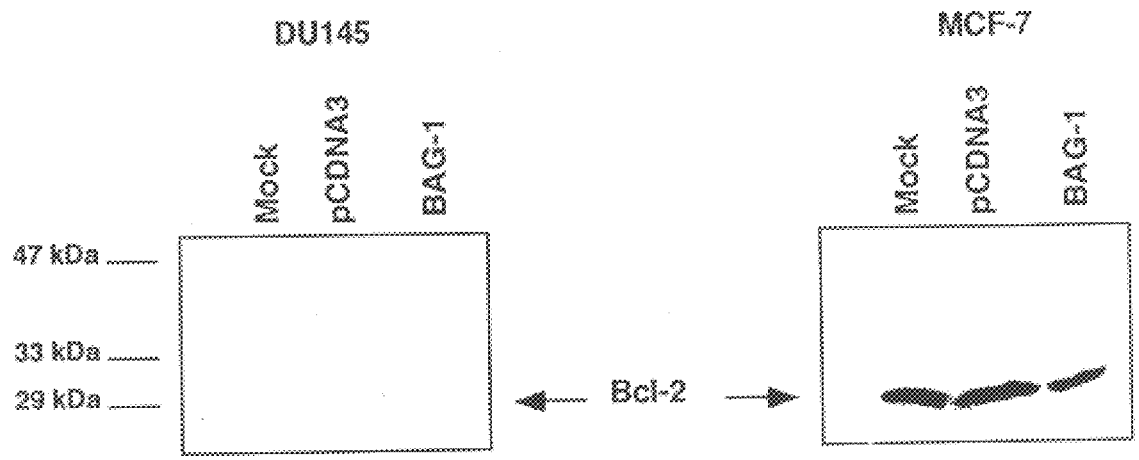

FIG. 22 shows the expression of BAG-1 and Bcl-2 in DU145 and MCF-7 cell lines. Equal amount of protein cell lysates (30 μg) were subjected to SDS-PAGE/immunoblot analysis. (FIG. 22A) Lysates from DU145 cells probed with an anti-BAG-1 antibody. BAG-1 protein migrates as a ~29 kDa protein. The anti-BAG-1 antibody also detects a non-specific cellular band at ~47 kDa. (FIG. 22B) Lysates from MCF-7 cells probed with the anti-BAG-1 antibody. (FIG. 22C) Cell extracts from DU145 probed with an anti-BCl-2 antibody. (FIG. 22D) MCF-7 cell lysates probed with an anti-Bcl-2 antibody. The positions of BAG-1 and Bcl-2 protein are indicated by an arrow.

Figure 23A:
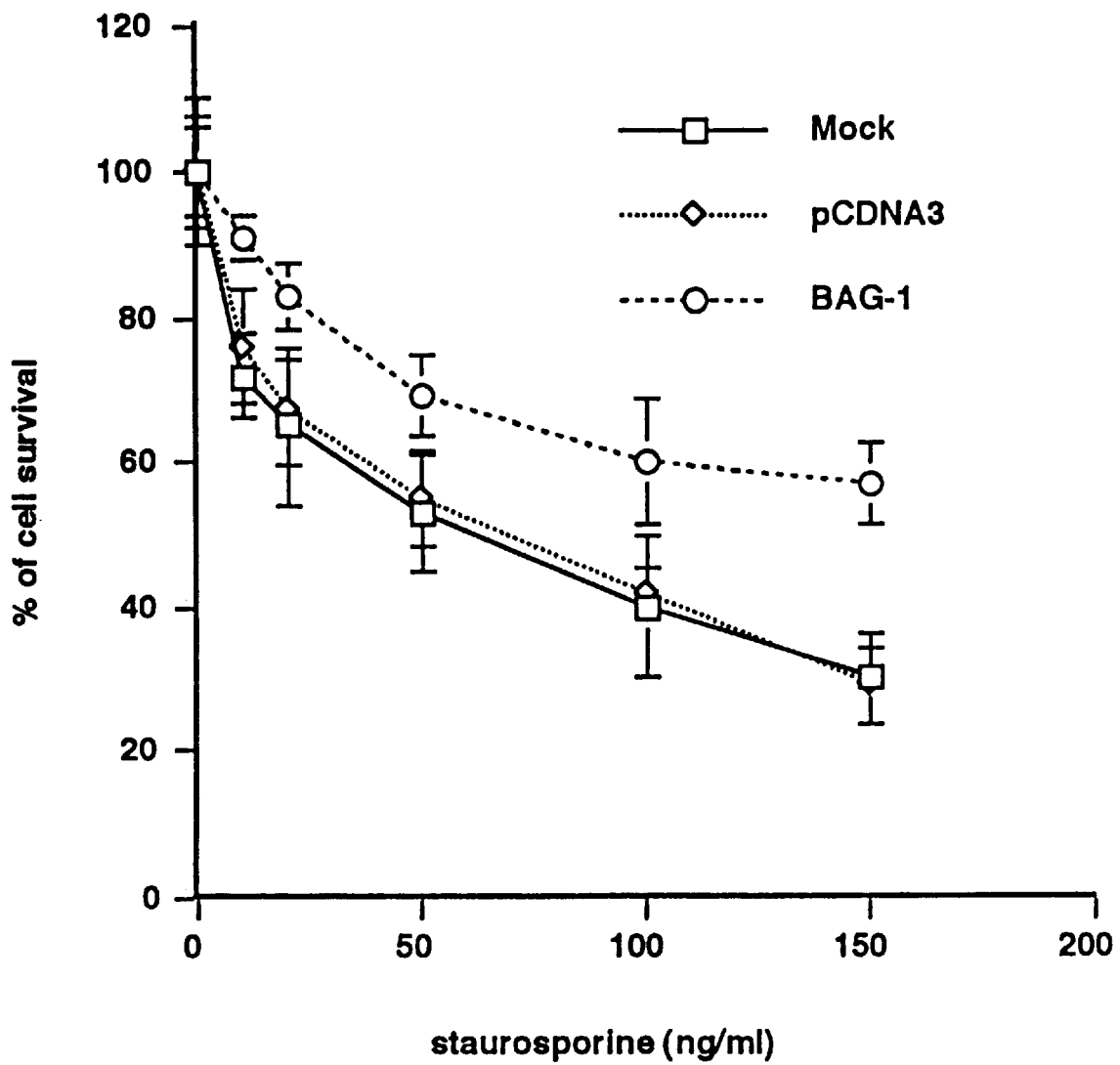
Figure 23B:
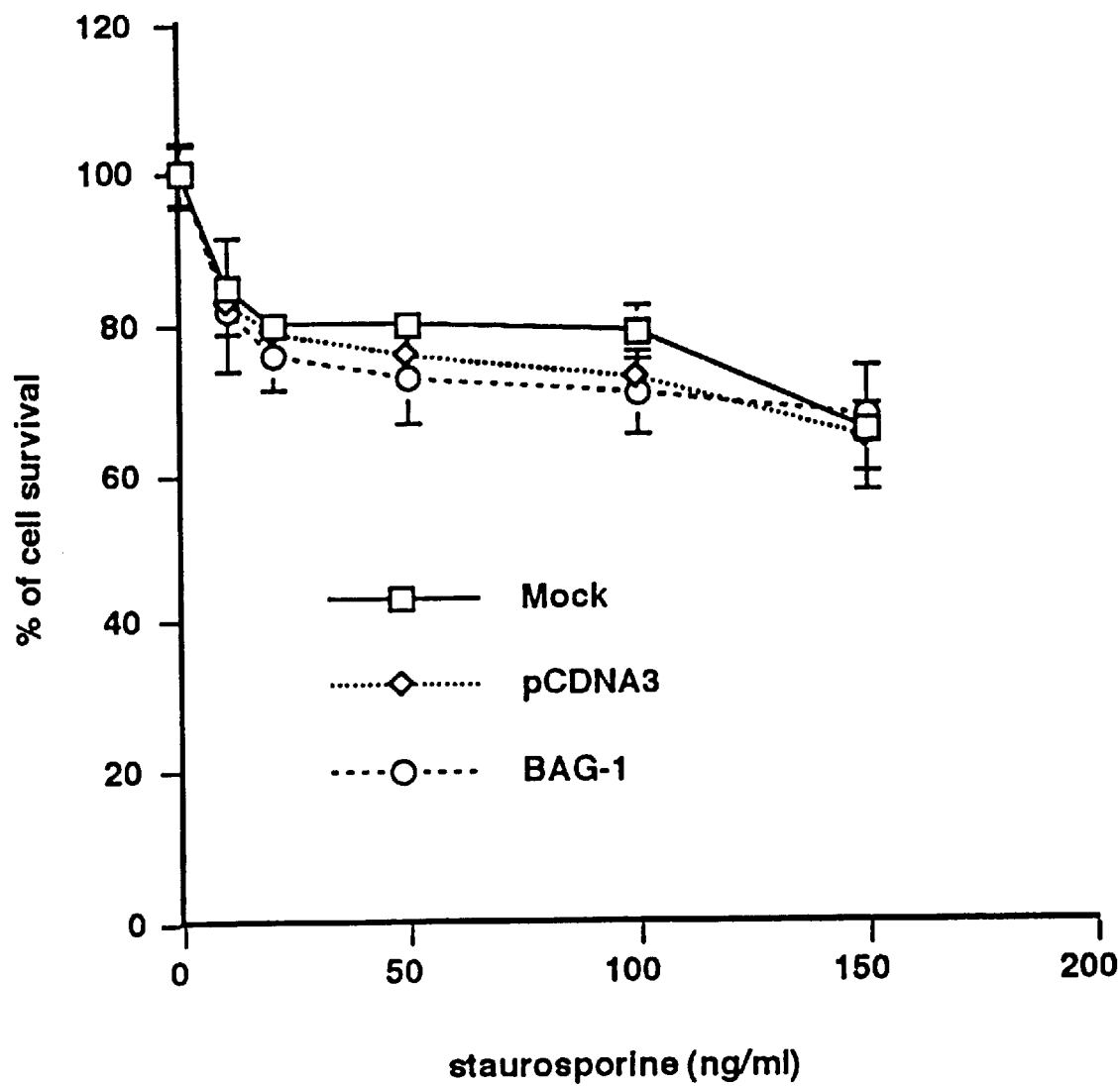

FIG. 23 shows the increased resistance to cell death by gene transfer-mediated expression of BAG-1 in MCF-7 compared to DU145 cells. Transfected cells were cultured in complete medium containing staurosporine at 0, 10, 20, 100 and 150 ng/ml. The percentage of viable cells was then determined at 4 days by MTS assays. The percentage of surviving cells was determined by comparing staurosporine untreated cells with staurosporine treated cells. All data represent mean±standard deviation (n=4). (FIG. 23A) MCF-7 cells survival. (FIG. 23B) DU145 cells survival.

Figure 24A:
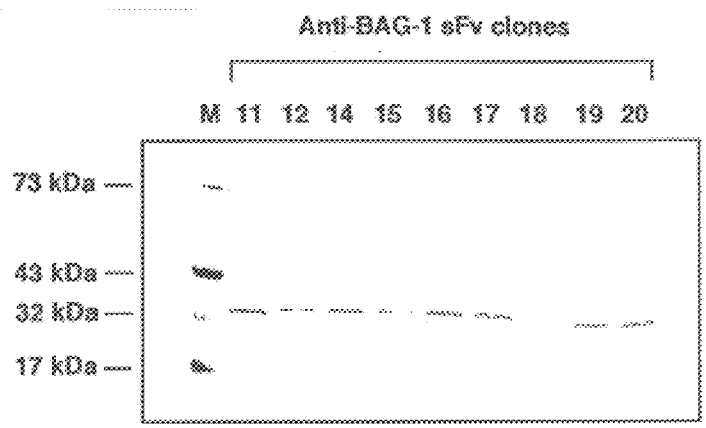
Figure 24B:
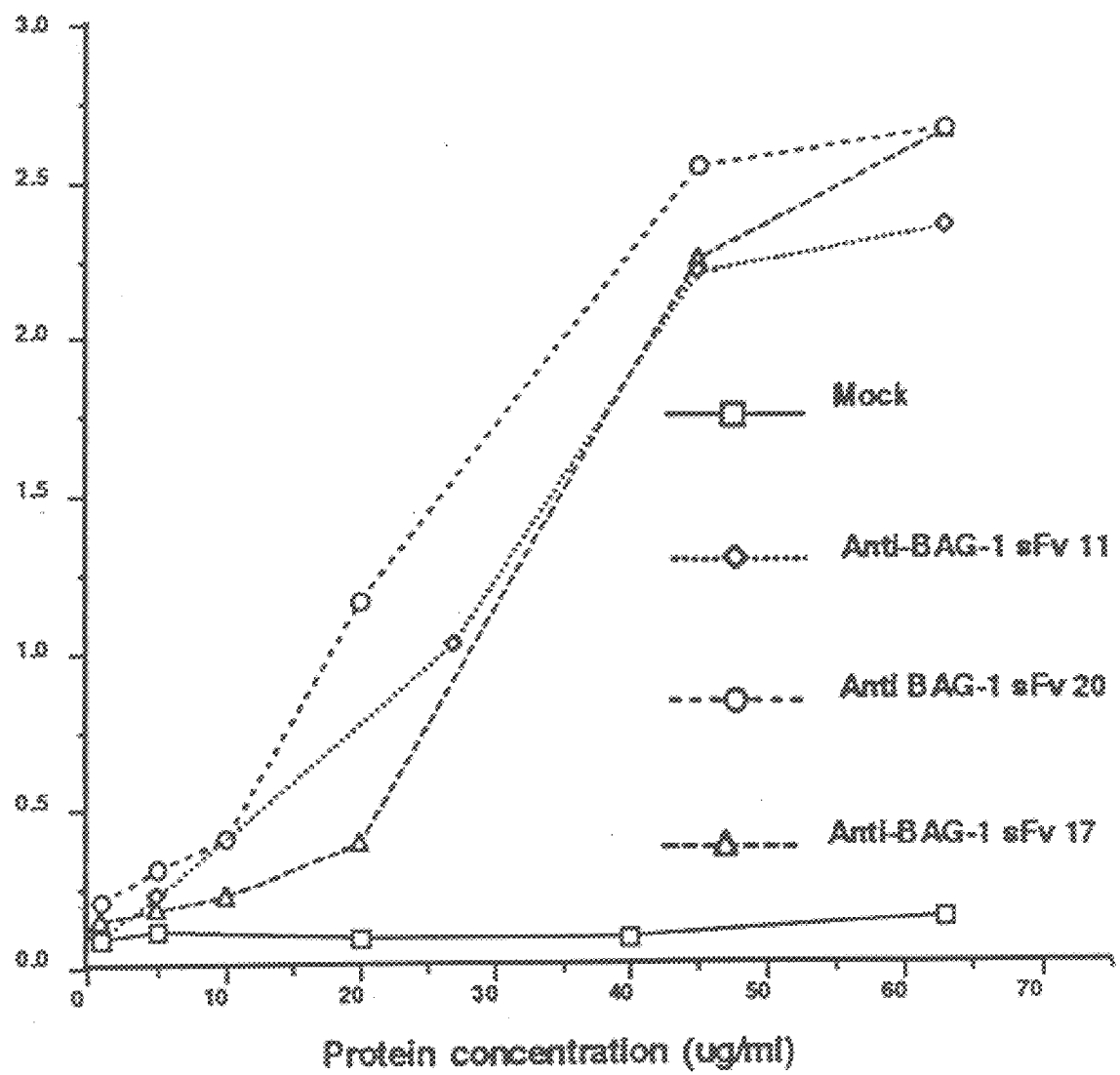

FIG. 24 shows the expression and binding affinity of anti-BAG-1 sFvs produced by differents E. coli HB2151 clones after induction with IPTG 1 mM. (FIG. 24A) Representative Western blot analysis of 9 different clones (out of 20) selected after colony lift assay screening. The periplasmic extracts prepared form IPTG-induced clones were run on SDS-PAGE gel (12%). After transfer, the membrane was probed with an horseradish peroxidase labeled anti-E-tag antibody. The anti-BAG-1 sFv migrates as a ~34–36 kDa protein. (FIG. 24B) Binding affinity of the anti-BAG-1 sFvs to BAG-1 protein as measured by ELISA. Various concentrations of periplasmic extracts from anti-BAG-1 sFv clones 11, 15 and 20 were added onto a 96 well plate coated with recombinant BAG-1 protein. A periplasmic extract containing no sFv protein was used as a negative control. After addtion of an HRP-conjugated mouse anti-E-tag antibody and the peroxidase substrate, the plate was read at 405 nm. Samples were done in duplicate and O.D. values are expressed as a mean.

Figure 25A:
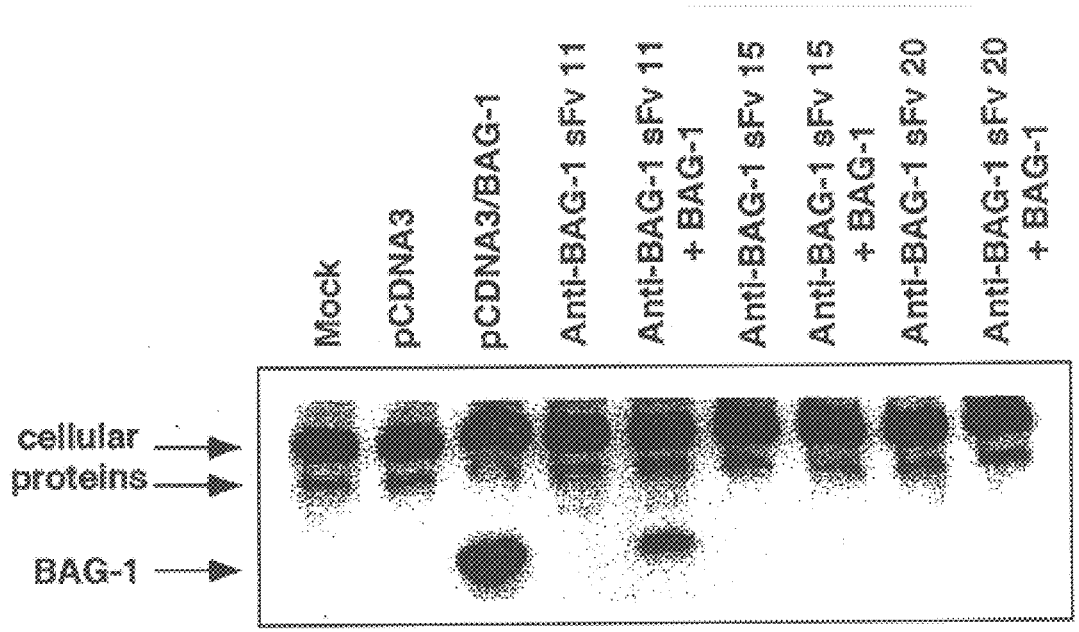
Figure 25B:
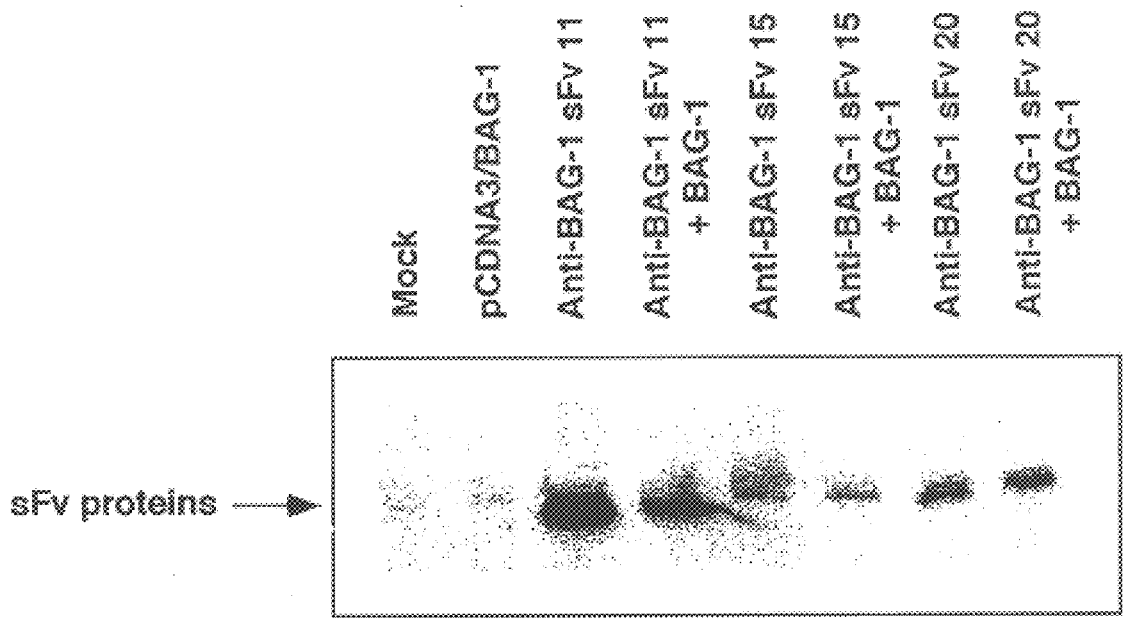
Figure 27A:
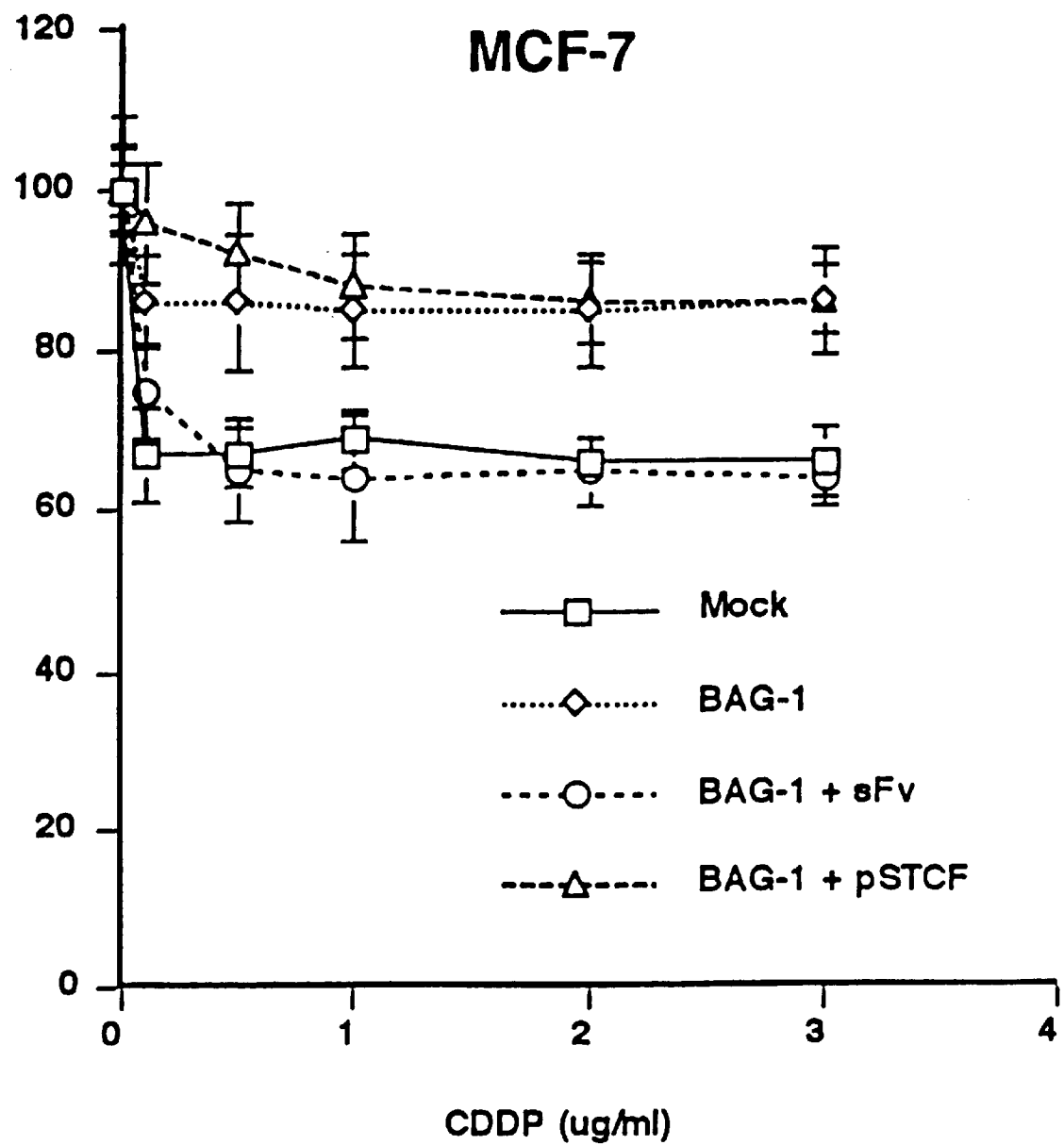
Figure 27B:
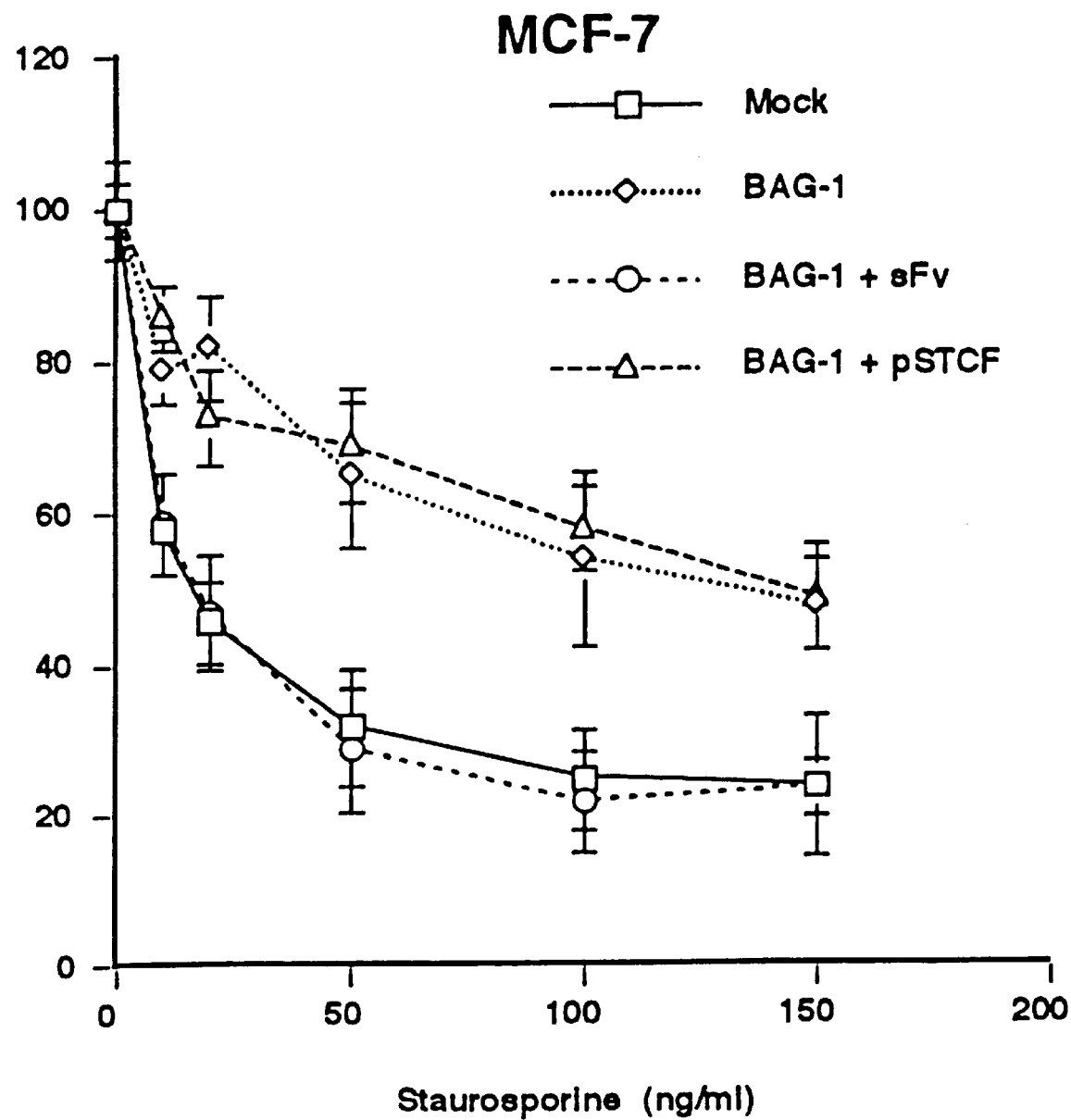
Figure 27C:
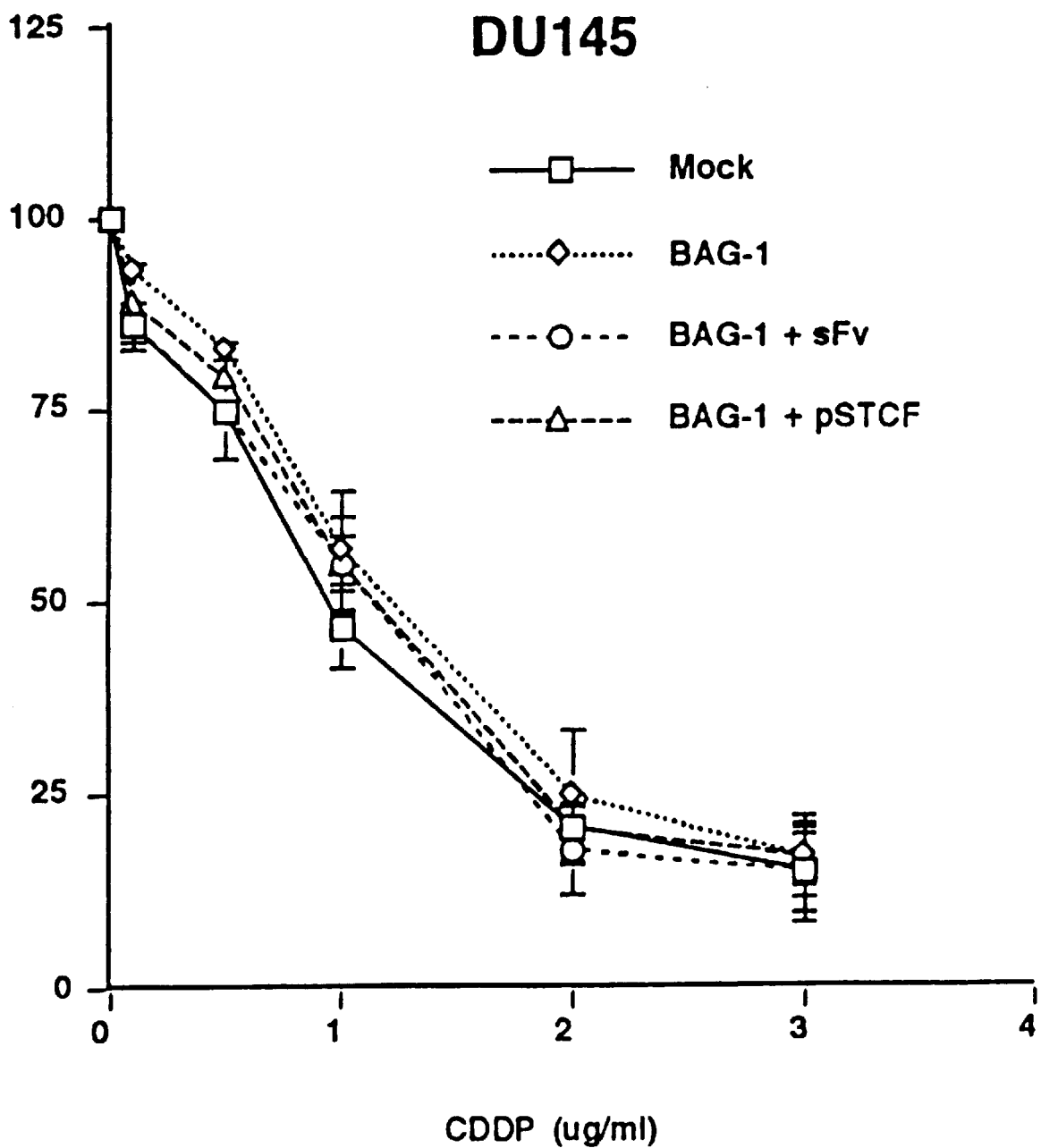
Figure 27D:
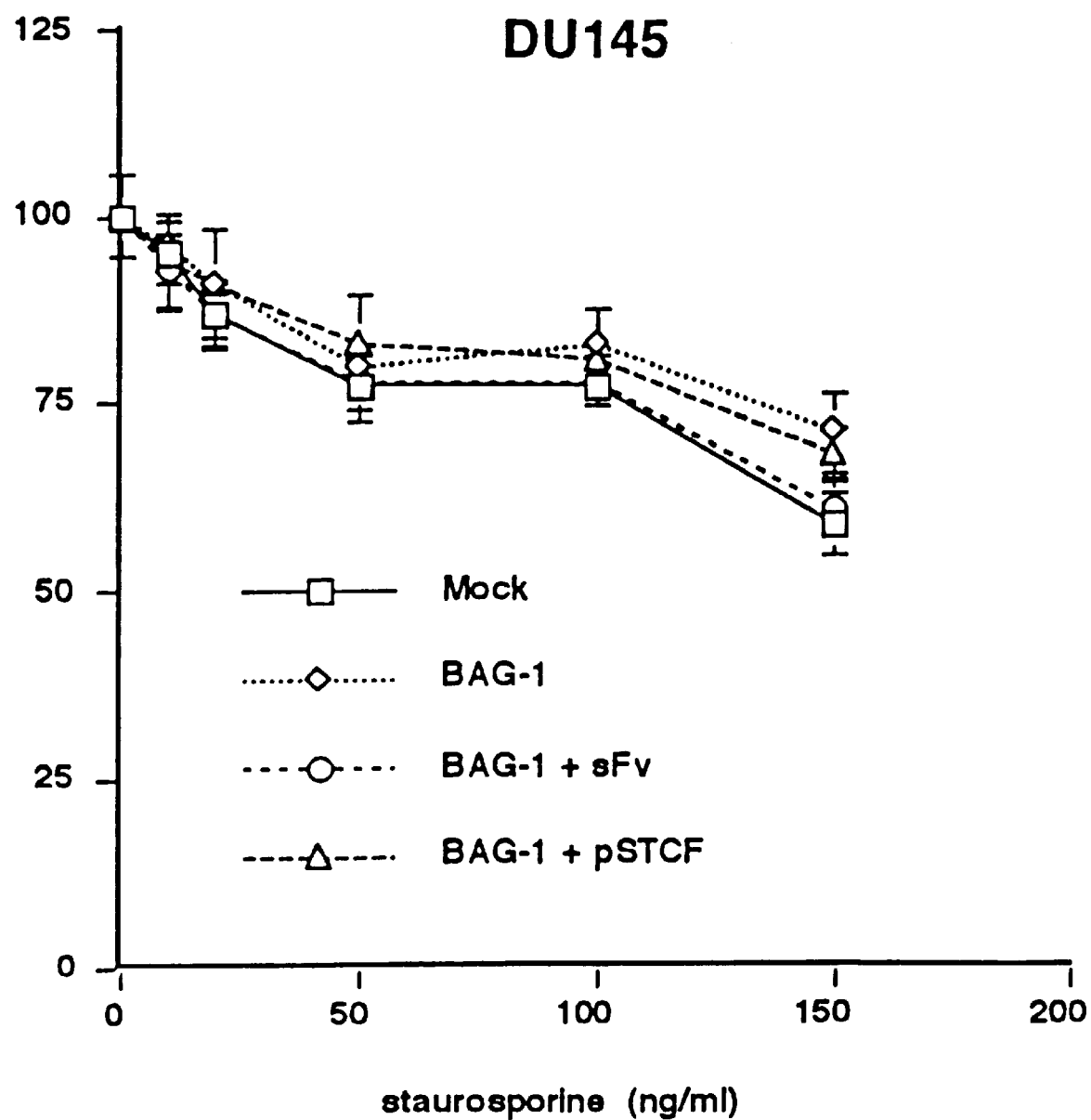

FIG. 25 shows (FIG. 25A) the modulation of BAG-1 expression in HeLa cells as determined by Western blot. Equal amount of protein cell lysates (30 μg) were loaded in each lane. Mock indicates that cells were treated with AdpL only; pCDNA3, the empty vector only; pCDNA3/BAG-1, the BAG-1 eucaryotic vector; anti-BAG-1 sFv, sFv expression vector; anti-BAG-1 sFv +BAG-1, sFv expression vector+BAG-1 eucaryotic vector (pCDNA3/BAG-1). The membrane was probed with an anti-BAG-1 antibody; and (FIG. 25B) the expression of the anti-BAG-1 sFvs in HeLa cells. Equal amount of cell lysates (30 μg) in each lane and protein expression was analysed by immunoblot assay using an anti-c-myc monoclonal antibody.

FIG. 26 shows that the anti-BAG-1 sFv down-regulates the expression of BAG-1 in DU145 and MCF-7 cells. DU145 (FIGS. 26A, 26C) and MCF-7 (FIGS. 26B, 26D) were transfected with BAG-1, BAG-1 and pSTCF.KDEL or BAG-1 and the anti-BAG-1 sFv 20. Thirty μg of total protein lysates were loaded per lane and Western blots were developed with anti-BAG-1 antibody. FIG. 26C DU145 cellls were transduced the vector (pSTCF.KDEL), the anti-BAG-1 sFv 20 or BAG-1 and anti-BAG-1 sFv 20 and expression of the sFv was analysed by Western blot. As above, 30 μg of proteins were loaded and the membrane was probed with an anti-c-myc antibody.

FIG. 27 shows that the anti-BAG-1 sFv abolishes BAG-1-mediated resistance to cell killing in MCF-7 but not in DU145. MCF-7 (FIGS. 27A–B) or DU145 (FIGS. 27C–D) cells were transfected with BAG-1, BAG-1 and anti-BAG-1 sFv 20 (BAG-1+sFv) or BAG-1 and pSTCF.KDEL (BAG-1+pSTCF) and then treated with either staurosporine or CDDP. The percentage of surviving cells was determined by MTS assay 4 days later. Samples were done in quadruplicate. Data are presented as mean±standard deviation.

Figure 28A:
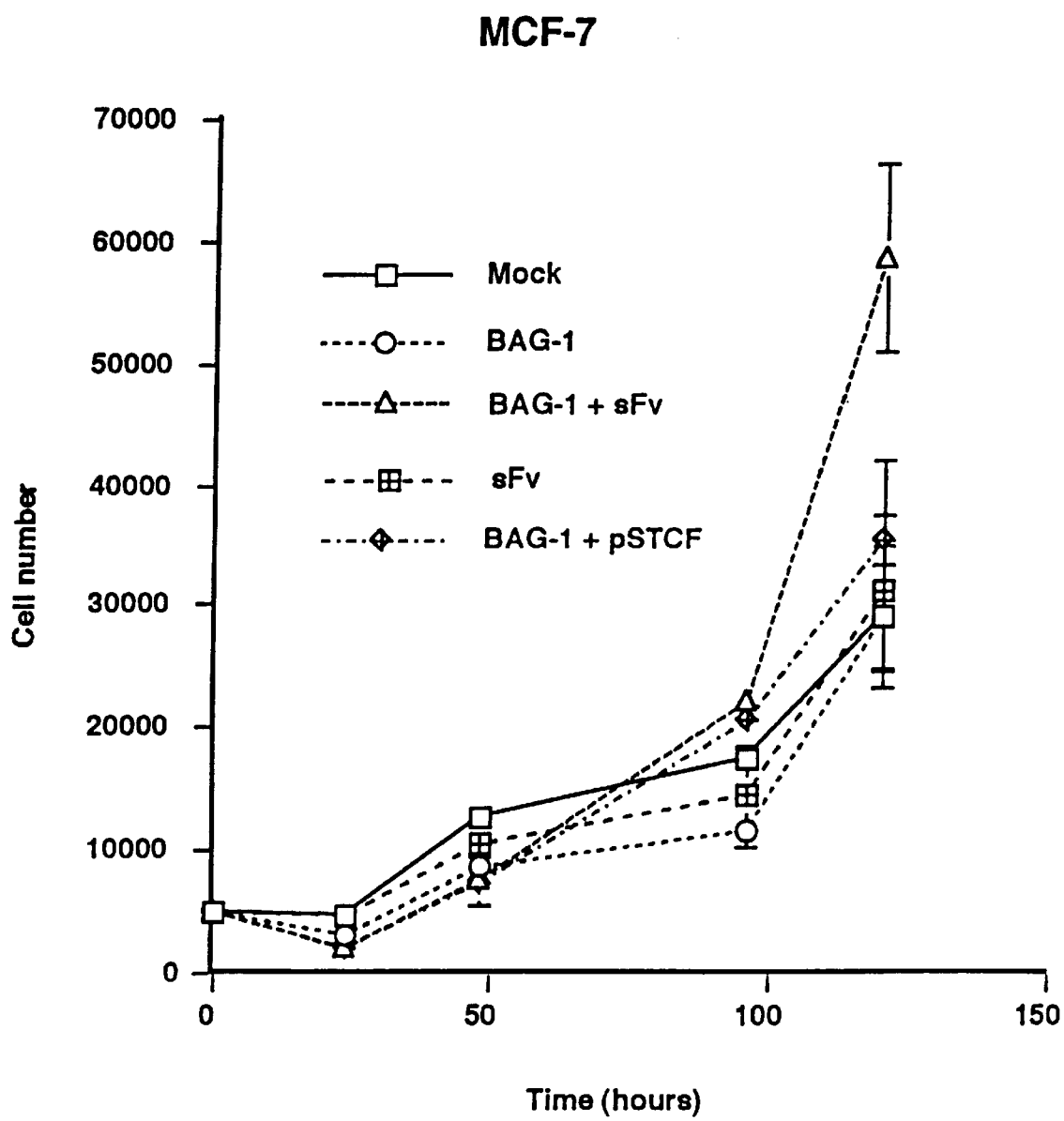
Figure 28B:
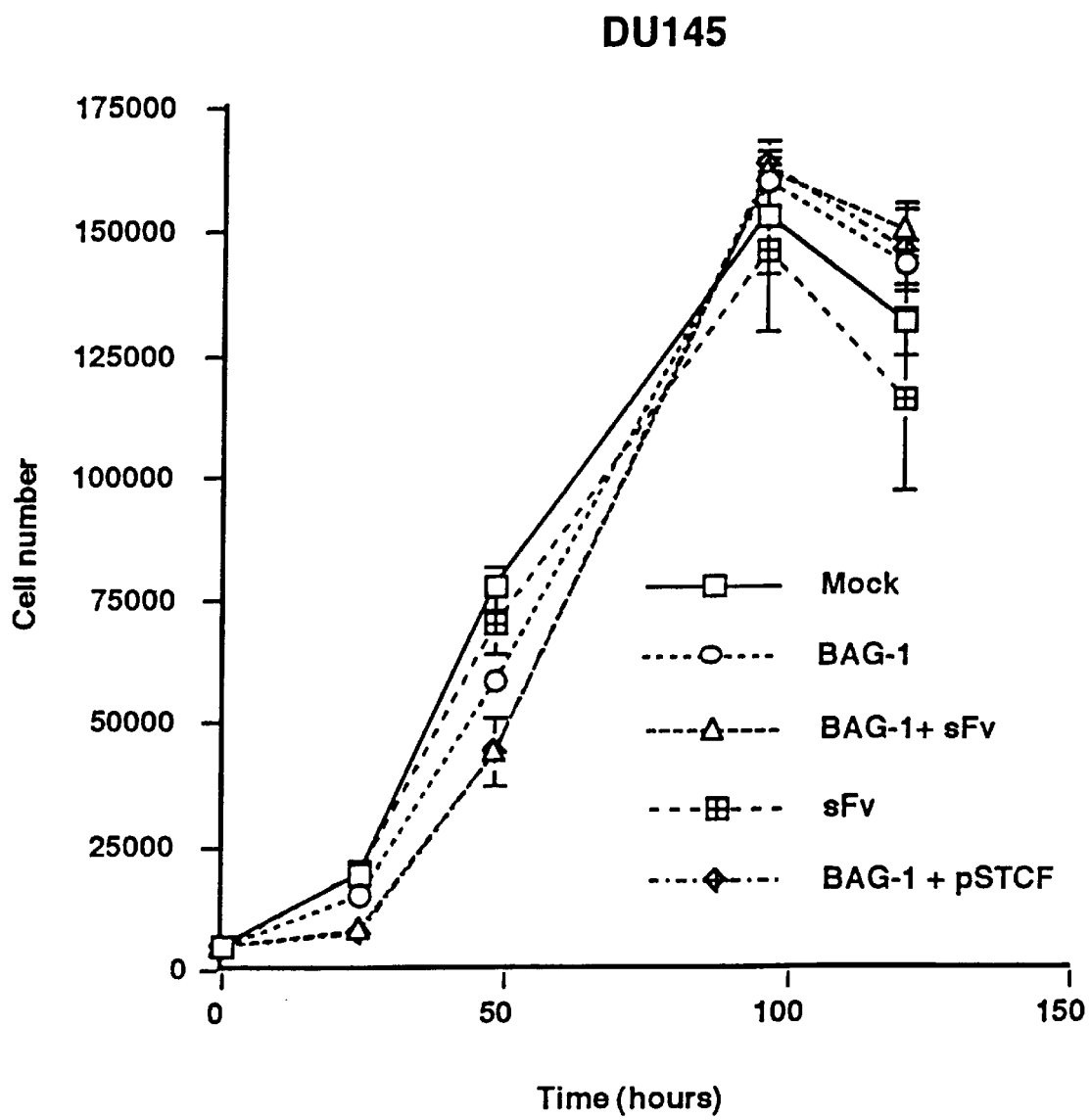

FIG. 28 shows that BAG-1 expression does not affect the growth rate of DU145 and MCF-7 under normal growth conditions. FIG. 28A shows the proliferation of MCF-7 cells transfected with the indicated plasmids was determined at various times by MTS assays. Data are presented as mean±standard deviation (n=4). In FIG. 28B, similar experiments done in DU145 cells.

Figure 29A:
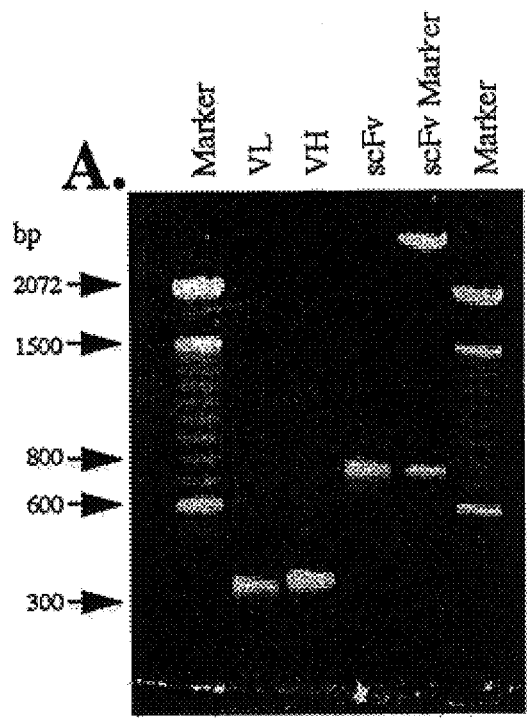
Figure 29B:
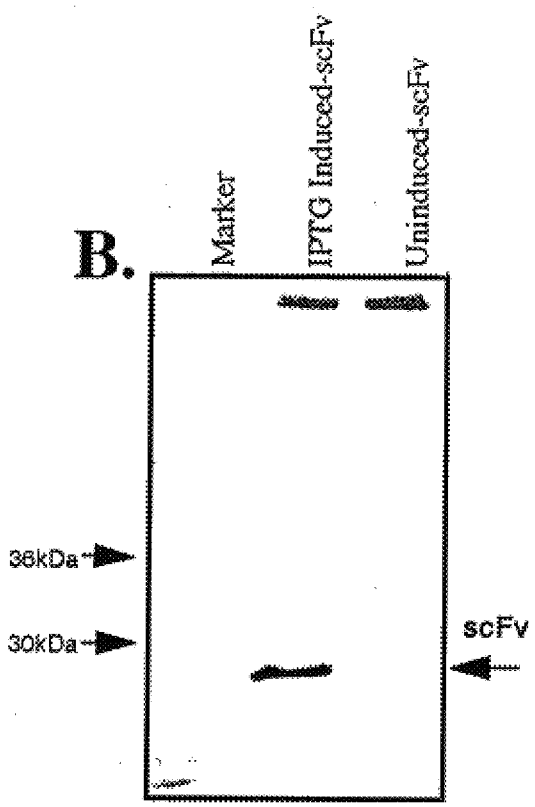
Figure 29C:
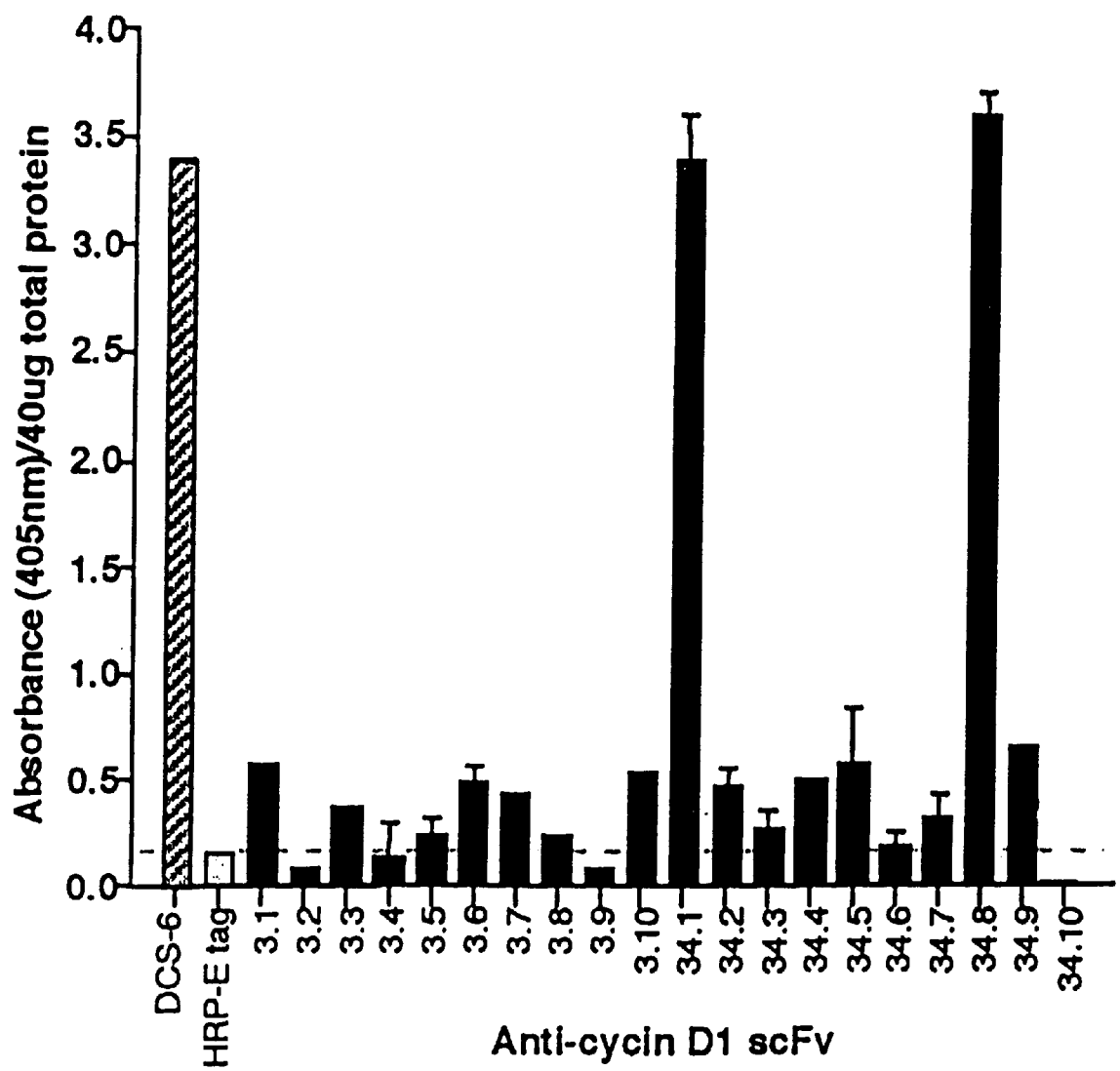

FIG. 29A: Molecular cloning of anti-cyclin-D1 sFv from RNA derived from the DCS-6 hybridoma cell line. The $V_L$ and $V_H$ domains of the RNA were amplified separately by RT-PCR, ligated together and reamplified with outstream primers. These products were visualized on an agarose gel (1%). FIG. 29B: Expression of anti-cyclin-D1 sFv in E. coli. SDS-PAGE (12%) of IPTG-induced and uninduced periplasmic protein. FIG. 29C: Enzyme-linked ELISA was used to measure the binding activity of the periplasmic expressed anti-cyclin-D1 sFv clones 3 and 34. Cyclin-D1 protein was coated on 96-well plates at the final concentration of 80 ng/well. After blocking with 3% milk, the periplasmic preparations were added to the plates. HRP-labeled mouse anti-E tag was used. Bound antibodies were detected by the addition of HRP substrate and determining the O.D. at 405 nm.

Figure 30A:
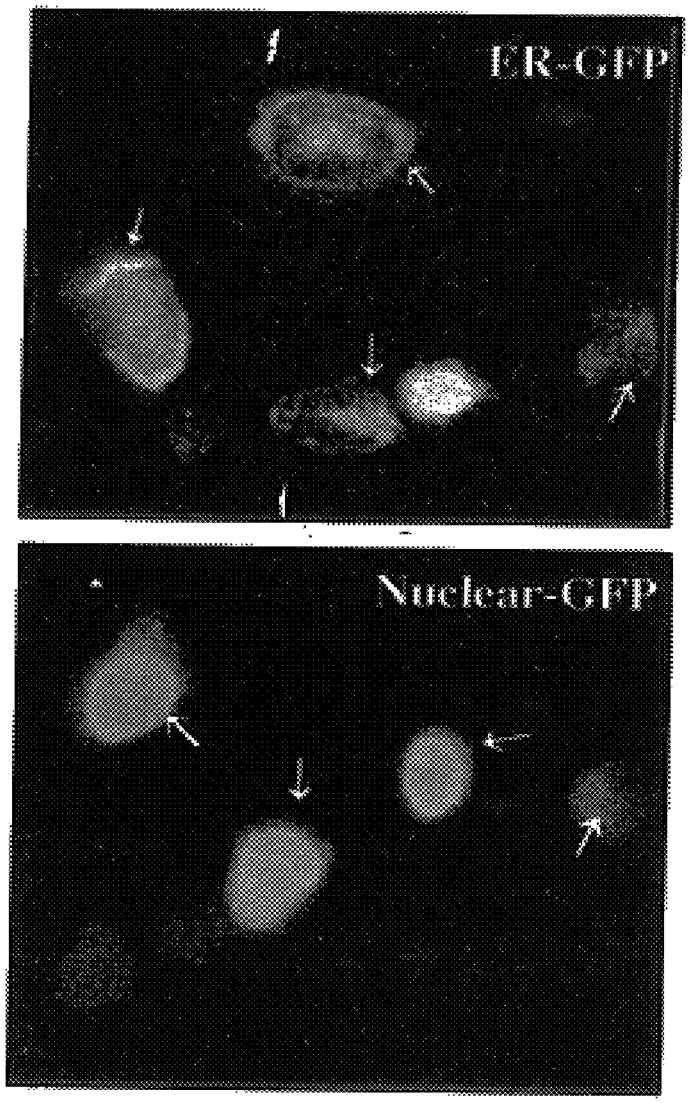
Figure 30B:
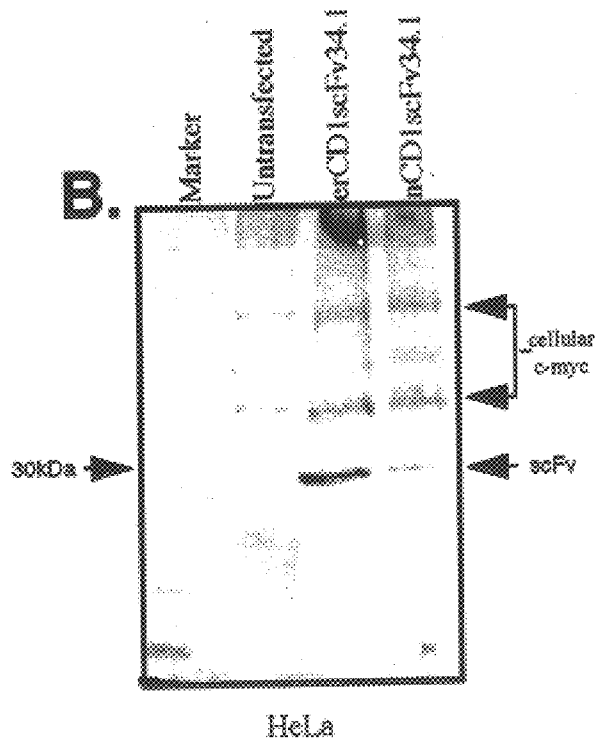
Figure 30C:
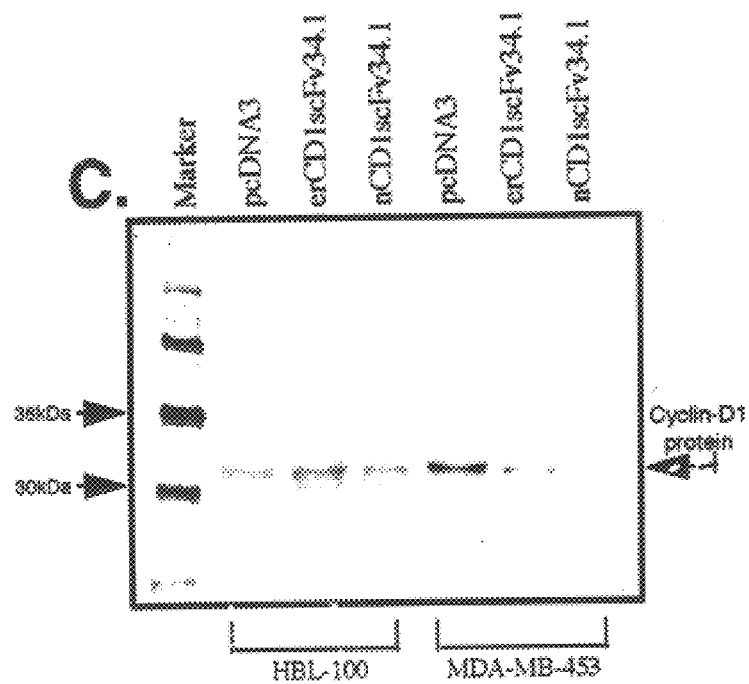

FIG. 30A: intracellular localization of GFP fusion protein in HeLa cells 48 hr after transfection with the ER and nuclear localizing vectors. FIG. 30B: Expression of intracellular anti-cyclin-D1 sFv in HeLa cells. FIG. 30C: Expression of cyclin-D1 protein five days post-transfection of anti-cyclin-D1 sFv. Fifty mg of total cellular protein from each of the indicated cell lines were subjected to 12% SDS-PAGE, transferred to nitrocellulose and immunoblotted.

Figure 31:
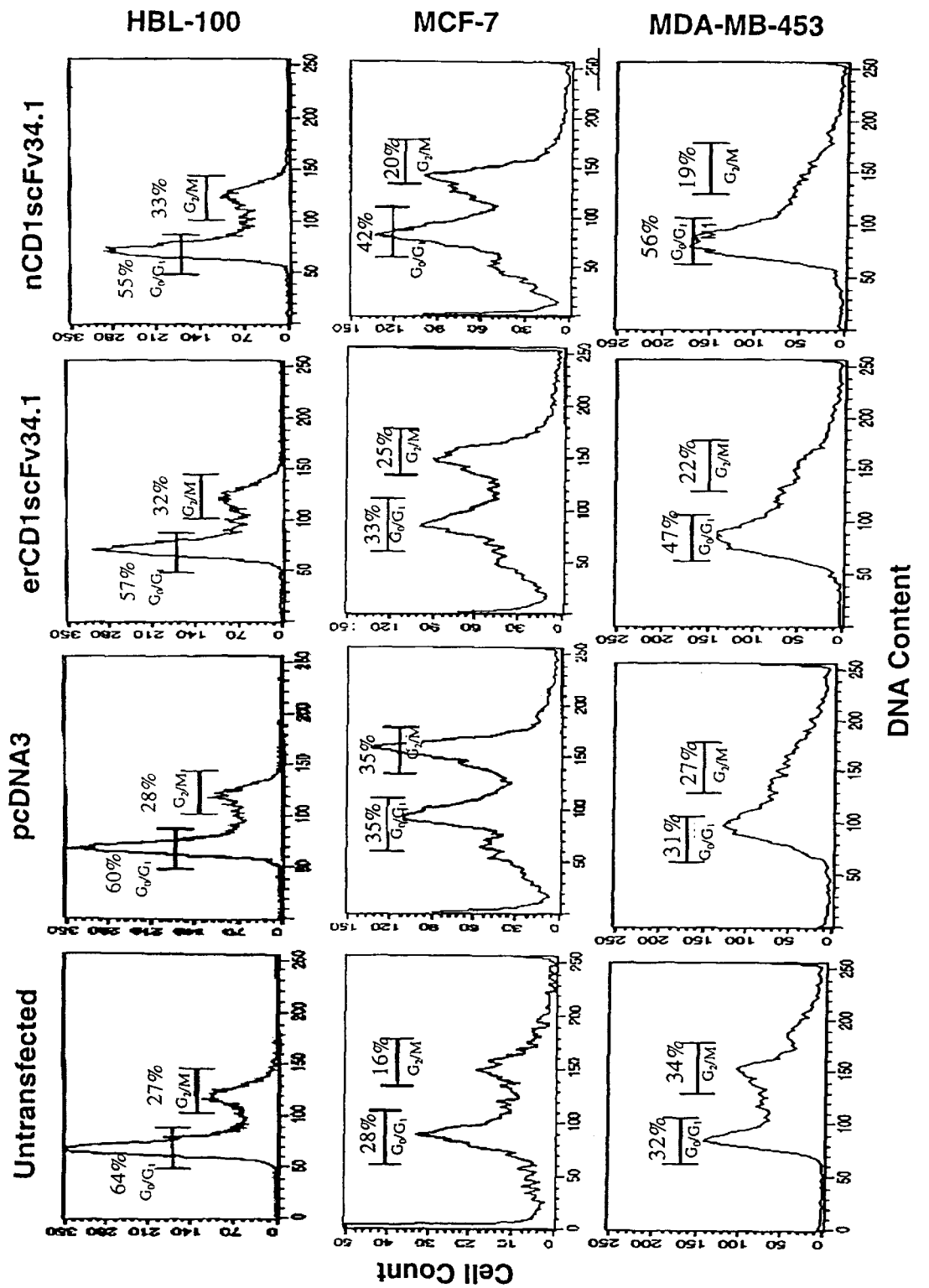

FIG. 31 shows the cell cycle analysis by FACS following staining with PI. 48 hr after transfection with the anti-cyclin-D1 sFv using AdpL nonsynchronized, log phase cells ($10^4$) were harvested and analyzed by FACS for cellular DNA content. Regions were set over the cell cycle phases and the percentage of cells within each region were determined using the CellQuest program.

Figures 32A, 32B, 32C:
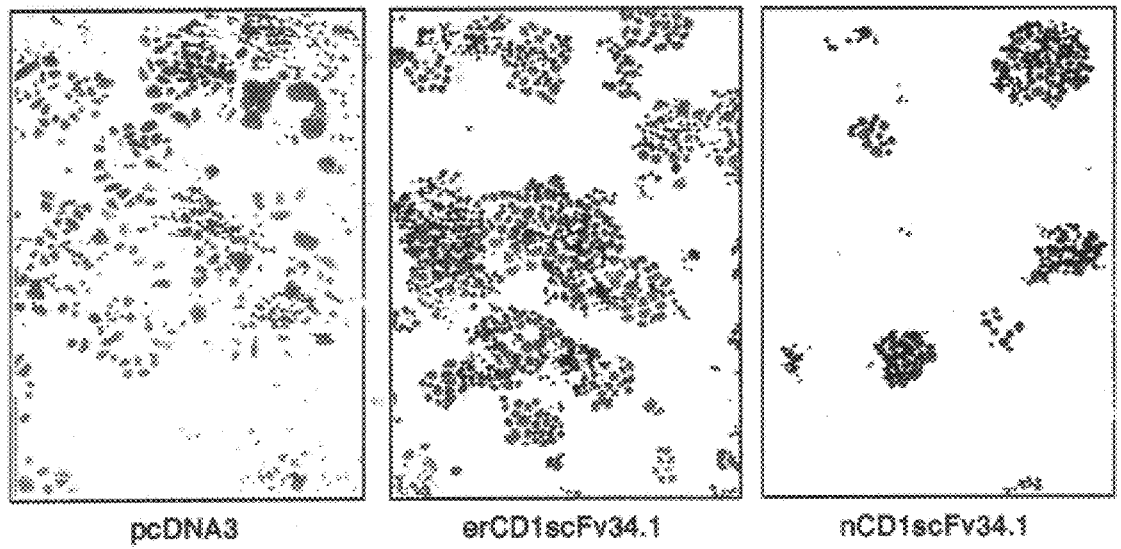

FIG. 32 shows the morphological appearance of MDA-MD-453 cells 5 days after transfection. FIG. 32A: Control vector pcDNA3, FIG. 32B: erCD1scFv34.1 and FIG. 32C: nCD1scFv34.1

Figures 33A, 33B, 33C:
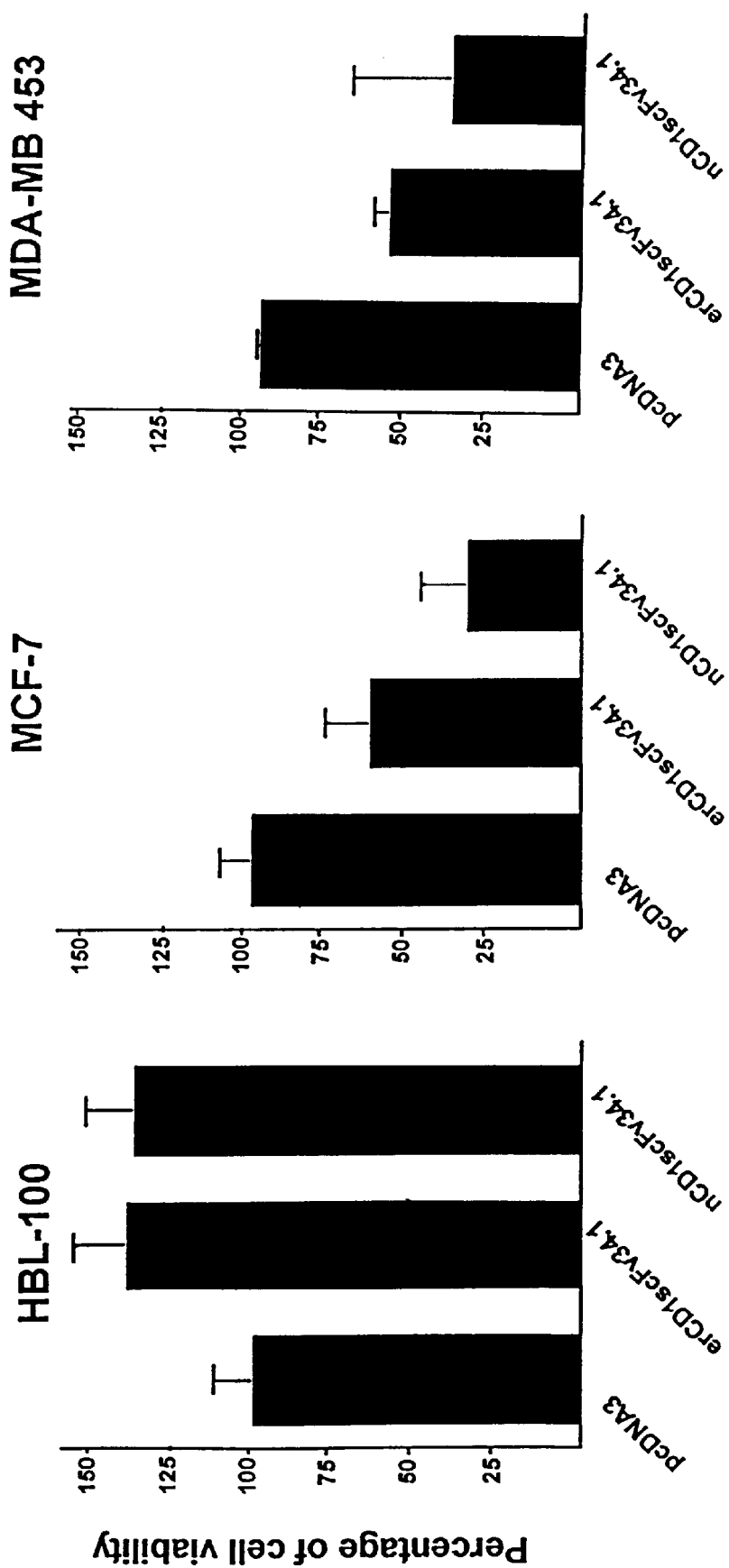

FIGS. 33A–33C show the percentage of cell viability after anti-cyclin-D1 scFv treatment. Plasmid DNAs pcDNA3, erCD1scFv34.1 and nCD1scFv34.1 were transfected into HBL-100, MCF-7 and MDA-MB-453. At day 5 post-transfection, the number of viable cells were counted in the Coulter Counter Model ZF.

DETAILED DESCRIPTION OF THE INVENTION

The present invention is directed to a method of enhancing the chemosensitivity and radiosensitivity of a neoplastic cell expressing an oncoprotein that stimulates proliferation of the cell, comprising introducing into the cell a nucleic acid molecule encoding an antibody homologue, wherein the antibody homologue is expressed intracellularly and binds to the oncoprotein intracellularly in the endoplasmic reticulum (ER) of the cell. Preferably, the oncoprotein is erbB2 although others can be targeted by those having ordinary skill in this art. Most preferably, the antibody homologue is selected from the group consisting of a single chain Fv fragment and a Fab fragment. The nucleic acid molecule is, for example, a recombinant expression vector selected from the group consisting of a viral vector and a plasmid vector. Generally, the neoplastic cell is from a tissue or organ selected from the group consisting of breast, gastrointestinal tract, lung, ovarian and salivary gland.

The present invention is also directed to a method of enhancing the chemosensitivity and radiosensitivity of a neoplastic cell, comprising the step of: introducing into the cell an antibody homologue, wherein the antibody homologue is expressed intracellularly and binds to a target protein intracellularly. In one embodiment, the antibody homologue binds in the endoplasmic reticulum of the cell. Alternatively, the antibody homologue binds to a target protein in the nucleus. In one embodiment, the neoplastic cell expresses an oncoprotein that stimulates proliferation of the cell. Most preferably, this method further comprises the step of contacting the cell with an anti-neoplastic agent, radiation or a combination thereof. Representative examples of an anti-neoplastic agent is selected from the group consisting of cisplatin, a halogenated pyrimidine, fluoropyrimidines, taxol, BCNU, 5-fluorouracil, bleomycin, mitomycin, hydroxyurea, fludarabine, nucleoside analogues, topoisomerase I inhibitors, hypoxic cell sensitizers and etoposide.

The methods of the present invention can be employed to treat a wide variety of cancers depending upon the target protein selected. Representative examples of neoplastic cell include ovarian cancer, bladder cancer, lung cancer, cervical cancer, breast cancer, prostate cancer, gliomas, fibrosarcomas, retinoblastomas, melanomas, soft tissue sarcomas, ostersarcomas, leukemias, colon cancer, carcinoma of the kidney, gastrointestinal cancer, salivary gland cancer and pancreatic cancer.

Generally, the target protein bound by the antibody homologue is a growth factor receptor protein, cell cycle control protein and anti-apoptotic protein. Representative examples of growth factor receptor proteins are erbB2 and epidermal growth factor receptor. Representative examples of anti-apoptotic proteins are Bcl-2 and BAG-1. Representative examples of cell cycle control proteins are cyclin D1 and cyclin B.

Preferably, the antibody homologue is selected from the group consisting of a single chain Fv fragment and a Fab fragment. In one embodiment, the antibody homologue is introduced to the cell via a nucleic acid molecule encoding said antibody homologue. The method nucleic acid molecule is preferably a recombinant expression vector such as a viral vector and a plasmid vector.

The present invention is also directed to a method of enhancing the chemosensitivity and radiosensitivity of a neoplastic cell, comprising the step of: introducing into the cell an antibody homologue, wherein the antibody homologue is expressed intracellularly and binds to a target protein intracellularly; and contacting said cell with an anti-neoplastic agent, radiation or a combination thereof.

The present invention is also directed to a method of inhibiting proliferation of erbB2-overexpressing tumor cells in a mammal, comprising the steps of: introducing into the cell an antibody homologue, wherein the antibody homologue is expressed intracellularly and binds to erbB2 intracellularly in the endoplasmic reticulum of the tumor cells; and contacting said cell with an anti-neoplastic agent, radiation or a combination thereof.

The following examples are given for the purpose of illustrating various embodiments of the invention and are not meant to limit the present invention in any fashion.

EXAMPLE 1

Anti-erbB-2 single-chain intracellular antibody (sFv) is specifically cytotoxic in erbB-2 overexpressing tumor cells As a method to effect targeted ablation of the erbB-2 oncoprotein, a strategy was developed involving construction of a gene encoding a single-chain immunoglobulin (sFv) directed against erbB-2. If an anti-erbB-2 sFv were localized to the endoplasmic reticulum of SKOV3 cells (an ovarian carcinoma cell line which overexpresses erbB-2), the nascent erbB-2 protein would be entrapped within the ER of the cells, and unable to achieve its normal cell surface localization. This intracellular entrapment would prevent erbB-2, a transmembrane tyrosine kinase receptor, from interacting with its ligand, thus abrogating the autocrine growth factor loop thought to be driving malignant transformation in erbB-2-overexpressing cell lines. To prevent maturational processing of the nascent erbB-2 protein during synthesis, a gene construct was thus designed which encoded an ER directed form of the anti-erbB-2 sFv (pGT21). As a control, a similar anti-erbB-2 sFv was designed which lacked a signal sequence dictating its localization to the ER (pGT20).

Figure 1A:
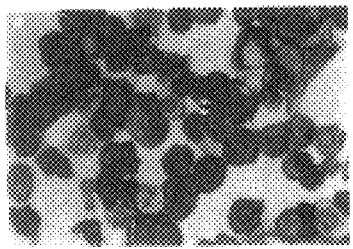
FIG. 1A: shows the transfection with control plasmid pcDNA3.
Figure 1B:
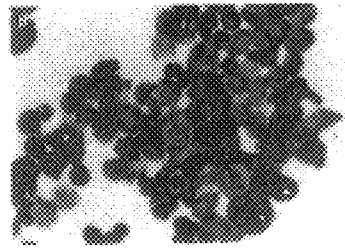
FIG. 1B: shows the transfection with non-ER form of anti-erbB-2 sFv plasmid, pGT20.
Figure 1C:
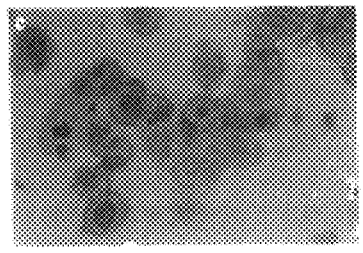
FIG. 1C: shows the transfection with ER form of anti-erbB-2 sFv plasmid, pGT21.

These sFv constructs were cloned into the eucaryotic expression vector pcDNA3 (Invitrogen), which directs high level gene expression from the cytomegalovirus (CMV) early intermediate promoter/enhancer. For this analysis, the plasmid DNAs pcDNA3, pGT20, and pGT21 were transfected into the erbB-2 overexpressing ovarian carcinoma cell line SKOV3 using the adenovirus-polylysine (AdpL) method. The adenovirus-polylysine-DNA complexes containing a $\beta$-galactosidase reporter gene (pCMVB) produced detectable levels of reporter gene expression in >99% of targeted cells. At various times after transfection, the cells were evaluated for cell surface expression of erbB-2 using an anti-human erbB-2 polyclonal antibody. Cells transfected with the control plasmid DNA, pcDNA3, exhibited high levels of cell surface erbB-2, as would be expected (FIG. 1). Additionally, SKOV3 cells transfected with the non-ER (cytosolic) form of the anti-erbB-2 sFv (pGT20) exhibited levels of cell surface erbB-2 similar to the control. In marked contrast, SKOV3 cells transfected with pGT21, which encodes an ER form of the anti-erbB-2 sFv, demonstrated marked down-regulation of cell surface erbB-2 expression. This down-regulation appeared to be time-dependent with cell surface erbB-2 levels progressively declining from 48 to 96 hours post-transfection. At 96 hours post-transfection, fewer than 10% of the pGT21 transfected cells exhibited detectable levels of cell surface erbB-2 protein.

To determine whether modulation of cell surface expression of erbB-2 levels affected cellular proliferation in the SKOV3 cells, the various gene constructs were transfected using the AdpL vector as before. For this analysis, immunohistochemistry for the proliferation-associated antigen Ki-67 was employed. Transfection of cells with the control plasmid pcDNA3 resulted in the immunohistochemical detection of active cellular proliferation as indicated by intense nuclear staining. In addition, transfection with the non-ER form of the anti-erbB-2 sFv did not result in any net change in cell proliferation. In marked contrast, transfection of the erbB-2 overexpressing cell line SKOV3 with the ER form of the anti-erbB2 sFv resulted in a dramatic inhibition of cellular proliferation.

Because the ER anti-erbB-2 sFv exhibited a prominent anti-proliferative effect, it was hypothesized that it might also exhibit an anti-tumor effect in cells stably modified to express this gene construct. As the plasmids pcDNA3, pGT20 and pGT21 contained neomycin selectable markers, they were used to derive stable clones. In an initial experiment, the various plasmid constructs were used to derive G418 resistant clones in HeLa cells, a human cervical carcinoma cell line not characterized by overexpression of erbB-2. After selection, the number of clones derived from transfection with pGT20 and pGT21 was not significantly different (Table 1). Further, the number of clones did not differ after transfection with the control plasmid pcDNA3. A similar analysis was then carried out with the erbB-2 overexpressing tumor line SKOV3 as the target. The number of clones derived with pGT20 did not differ from the number derived with the control plasmid pcDNA3 (Table 1).

However, transfection with pGT21 resulted in a dramatic reduction in the number of stable clones derived ($p<0.001$). Thus, the expression of the ER form of the anti-erbB-2 sFv was incompatible with long term viability of transfected SKOV3 cells. Further, this effect was specific for erbB-2 overexpressing cells as this differential clone survival was not noted in the HeLa cells. Thus, non-erbB-2 expressing tumor cells were not affected by this specific anti-erbB-2 intervention. Although the stable expression of the anti-erbB-2 sFv appeared to inhibit clonal development selectively in the erbB-2 overexpressing SKOV3 cell line, it did not completely abrogate clonal outgrowth; stable clones expressing the selectable marker and erbB-2 sFv were derived. These findings suggested that a subset of tumor cells could achieve clonal outgrowth despite the co-existence of over-expressed erbB-2 and the intracellular anti-erbB-2 sFv.

EXAMPLE 2

Oncoprotein ablation mediated by the anti-erbB-2 sFv induces apoptotic cell death in erbB-2 overexpressing human tumor cells As the expression of the anti-erbB-2 sFv appeared to inhibit the derivation of stable clones from SKOV3, whether the effect of expression of the single-chain antibody was directly cytocidal was determined. Plasmid DNAs which encoded either the cytosolic form or the ER form of the anti-erbB-2 sFv, as well as the control plasmid pcDNA3, were delivered to SKOV3 cells.

Figure 2A:
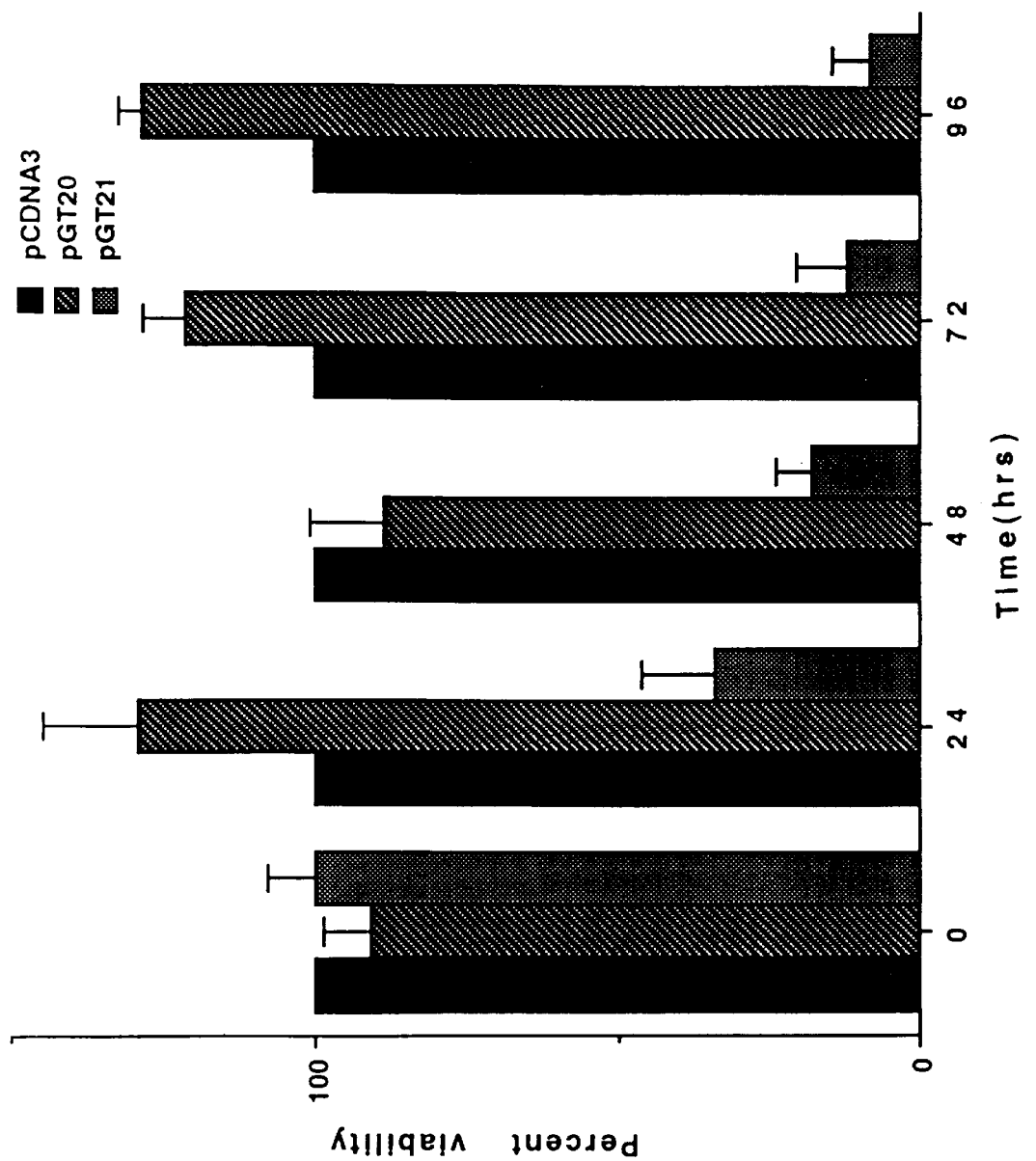
FIG. 2 shows the effect of expression of intracellular anti-erbB-2 sFv genes on tumor cell viability in the erbB-2 overexpressing human ovarian carcinoma cell line SKOV3 (FIG. 2A) and the non-erbB-2 expressing cervical carcinoma cell line HeLa (FIG. 2B). Tumor cell targets were transfected with the plasmids pcDNA3, pGT20 and pGT21. At indicated times post-transfection, cell viability was determined employing the XTT assay. Assays were performed ×12 at each time point.
Figure 2B:
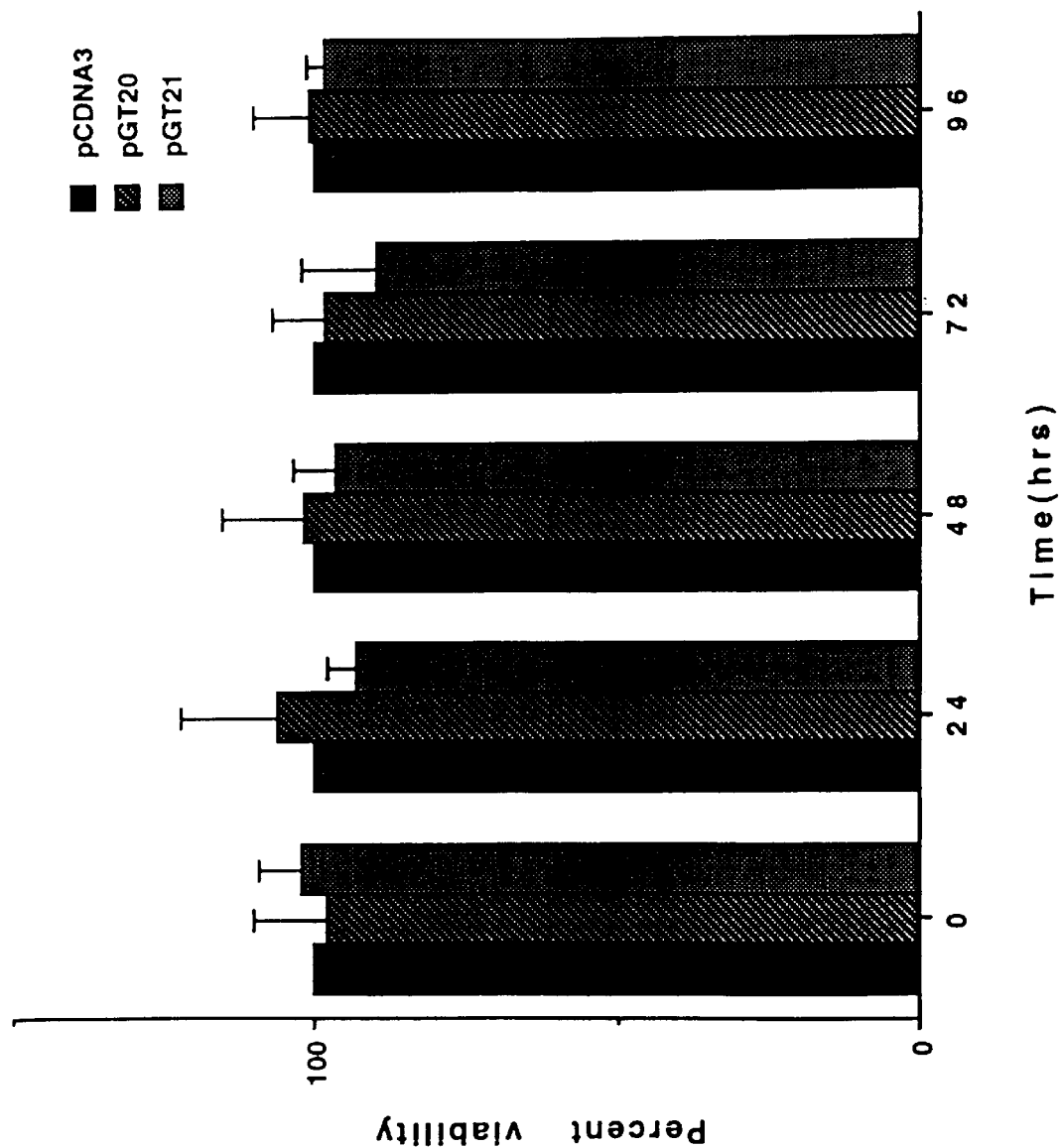

Transfection with pGT21 resulted in a time-dependent decrease in cell viability, with a >95% decrement in the number of viable cells by 72 hours post-transfection (FIG. 2). Transfection with the control plasmids pcDNA3 and pGT20, however, did not exert any significant effect on cell viability. As an additional control, the ER form of the anti-erbB-2 sFv again had no observable effect on the non-erbB-2 expressing human cervical carcinoma line HeLa. Non-erbB-2 expressing human cell lines from a variety of different tissues (bladder, liver, mesothelium, kidney) were also transduced and not significant cytotoxicity was noted. A subset of the cells was not eradicated by this intervention. Despite that >99% of the cells were transfected to transiently express the anti-erbB-2 sFv, in a subset of these transfected cells the anti-erbB-2 sFv did not appear to effectively induce cytotoxicity. This agrees with the derivation of anti-erbB-2 sFv-expressing SKOV3.ip1 stable clones noted in Table 1.

Figure 3A:
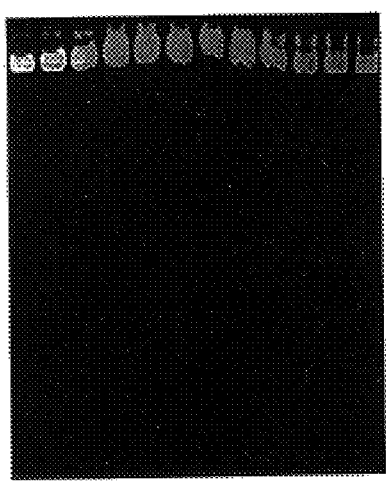
FIG. 3A: shows transfection of the non-erbB-2 expressing human cervical cell line HeLa.
Figure 3B:
FIG. 3B: shows transfection of the erbB-2 overexpressing human ovarian carcinoma cell line SKOV3.

The foregoing studies are consistent with the concept that the ER form of the anti-erbB-2 sFv induces specific cytotoxicity in erbB-2 overexpressing tumor cells. However, this effect may not simply be based on erbB-2 down-regulation, as antisense inhibition of erbB-2 gene expression elicited proliferative arrest of erbB-2 overexpressing cells, but not their death. Studies were carried out to determine if programmed cell death, i.e. apoptosis, was occurring. As before, the plasmid DNA constructs pcDNA3, pGT20 and pGT21 were delivered to the erbB-2 overexpressing SKOV3 cells and the non-erbB-2 expressing tumor cell line HeLa. At specific time points post-transfection, cells were harvested and evaluated for evidence of nuclear DNA fragmentation, a hallmark of programmed cell death. In the HeLa cells, transfection with the various constructs did not demonstrate any evidence of apoptotic cellular events as determined by morphologic appearance or alterations in DNA as measured by gel electrophoresis (FIG. 3A). Transfection of the SKOV3 cells with the control plasmid pcDNA3 or the cytosolic anti-erbB-2 sFv pGT20 similarly did not elicit any evidence of cellular apoptosis. When the SKOV3 cells were transfected with the ER form of the anti-erbB-2 sFv, however, marked changes in chromosomal DNA were noted. These changes were first detected at 48 hours post-transfection and were revealed on a 2% agarose gel as a characteristic 200 bp apoptotic ladder (FIG. 3B).

As independent confirmation, the presence of apoptotic nuclei was evaluated employing differential nuclear uptake of DNA-binding dyes. SKOV3 cells transfected with the plasmid DNA pGT21 showed intense nuclear staining characteristic of cellular apoptosis.

These alterations were not seen in cells transfected with the control plasmids pcDNA3 and pGT20.

Quantitative analysis demonstrated that >90% of the transfected SKOV3 cells exhibited apoptotic nuclear changes, whereas cells transfected with pcDNA3 and pGT20 did not exhibit levels of apoptosis different from untransfected controls. Thus, the basis of the cytocidal effect of the ER anti-erbB-2 sFv in the erbB-2 overexpressing cells was the induction of apoptosis. In the context of dominant oncogene induced tumorigenesis, down-regulation of over-expressed immortalizing growth factor receptors may induce cellular apoptosis. Thus, the abrogation of the immortalizing stimulus allows cells to re-engage the over-ridden apoptotic program. Alternatively, ablation of dominant oncogene function may result in proliferative arrest, without induction of programmed cell death.

Figure 4:
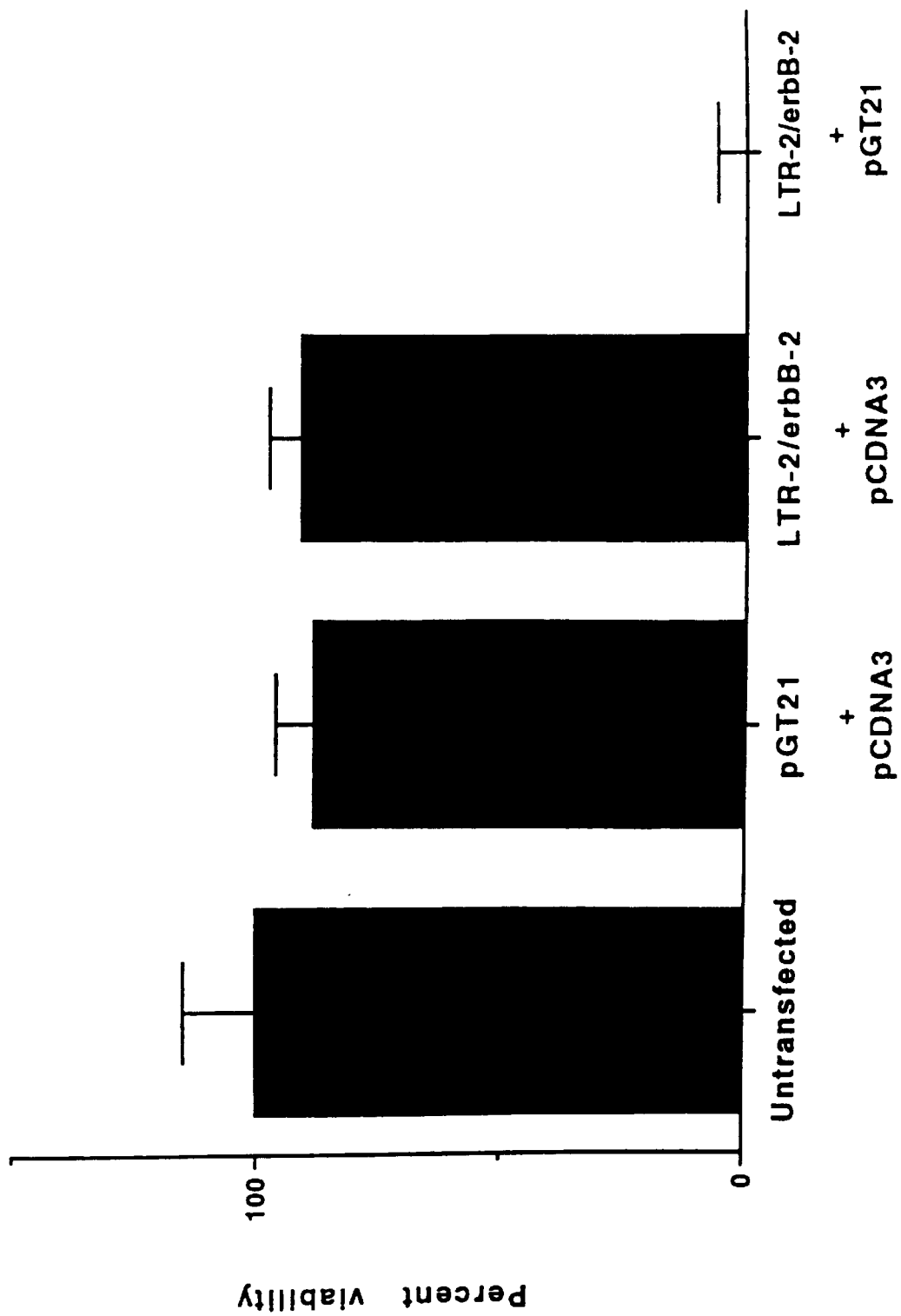
FIG. 4 shows the effect of coexpression of erbB-2 and the anti-erbB-2 sFv on HeLa cell viability. The non-erbB-2 expressing human tumor cell line HeLa was transfected with plasmids encoding the ER form of the anti-erbB-2 sFv (pGT21) and/or the human erbB-2 expression vector LTR-2/erbB-2. At 96 hours post-transfection the viability of the cells was determined employing the XTT assay. The mean of 8 assays is shown.
Figure 5:
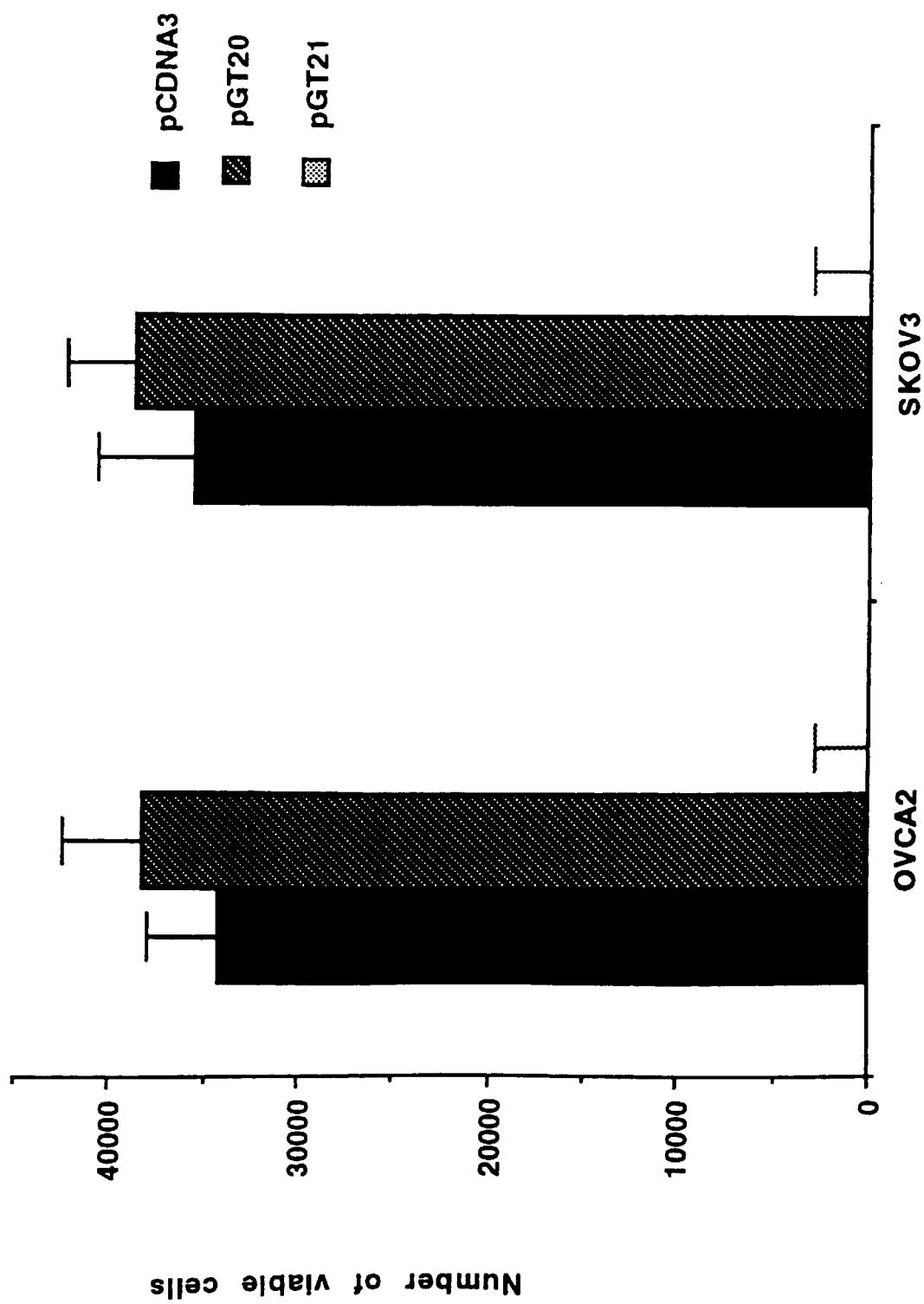
FIG. 5 shows the effect of expression of the anti-erbB-2 sFv gene on human ovarian tumor cell viability. ErbB-2 expressing human primary ovarian carcinoma cells isolated from malignant ascites were transfected with pcDNA3, pGT20 or pGT21. ErbB-2 overexpressing ovarian carcinoma cells (SKOV3) were used as additional controls. Cells were assayed for viability by the XTT assay at 96 hours post-transfection. This experiment was replicated 10×. Data represents mean±SEM.
Figure 6B:
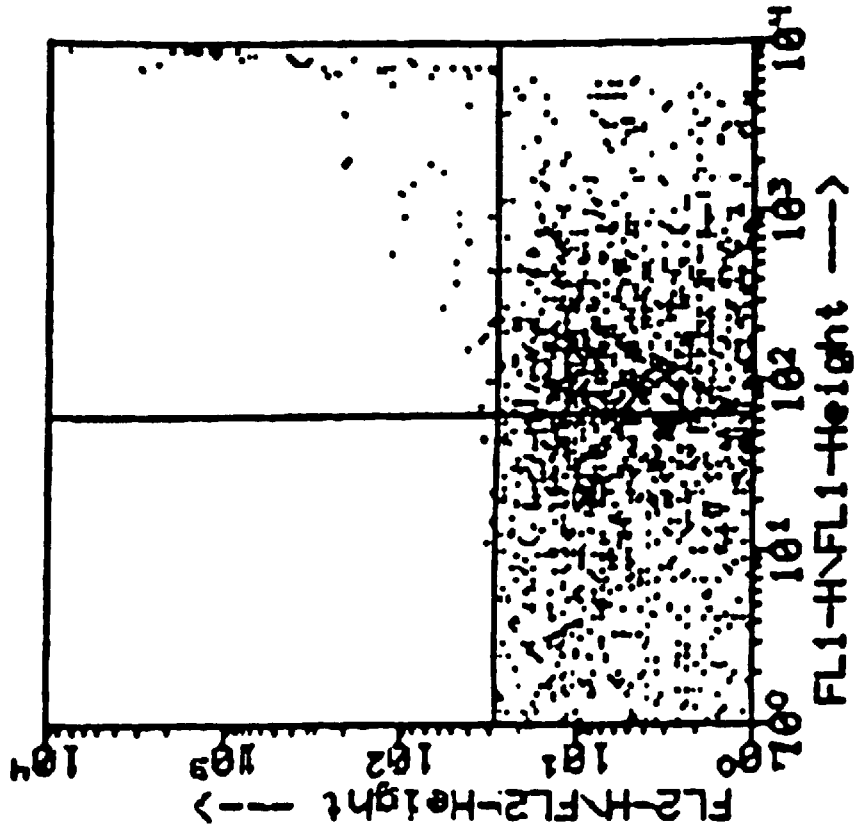
FIGS. 6A–6D show the the efficacy of various vectors in accomplishing in vivo gene delivery. Intraperitoneally transplanted SKOV3.ip1 cells were challenged with different vector systems delivering the lacZ reporter gene. Peritoneal lavage contents were subjected to FACS analysis for lacZ expression in erbB-2 overexpressing tumor cells.
Figure 6A:
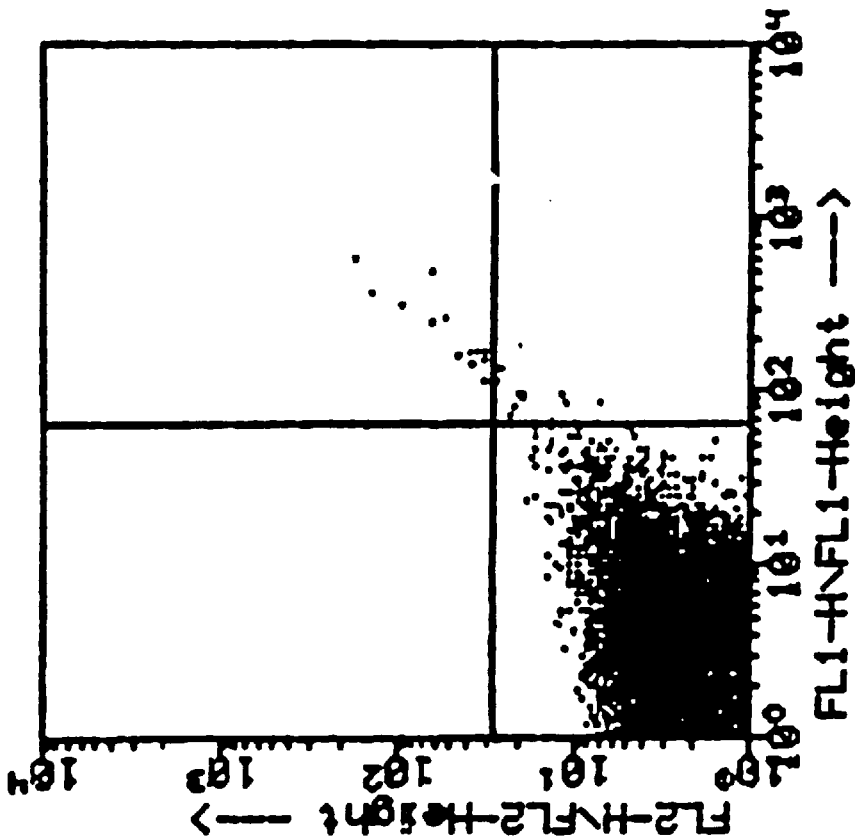
Figure 6D:
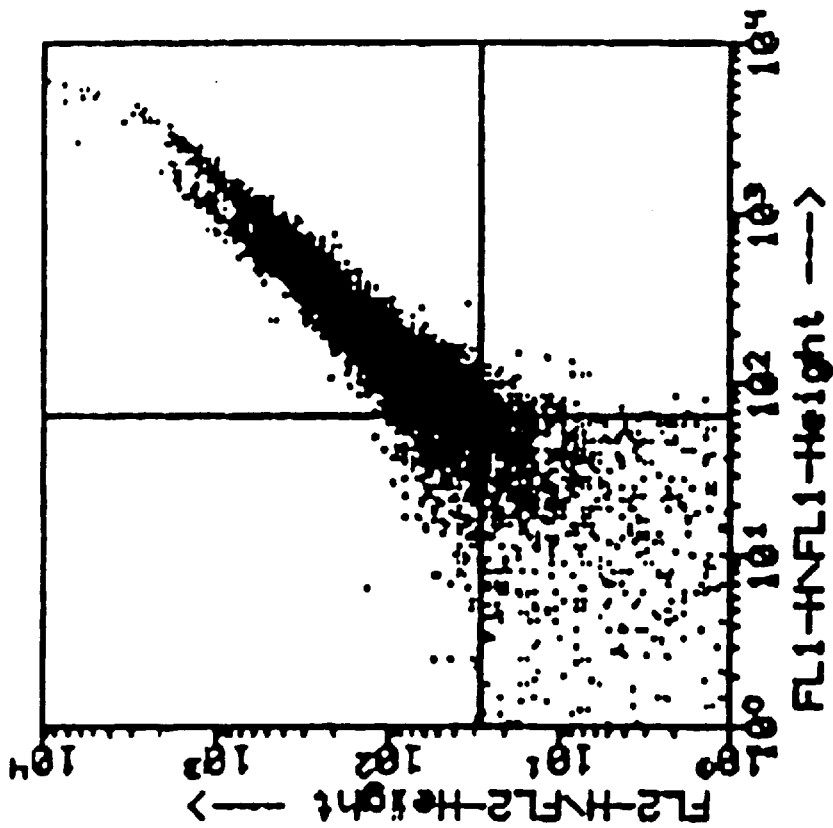
Figure 6C:
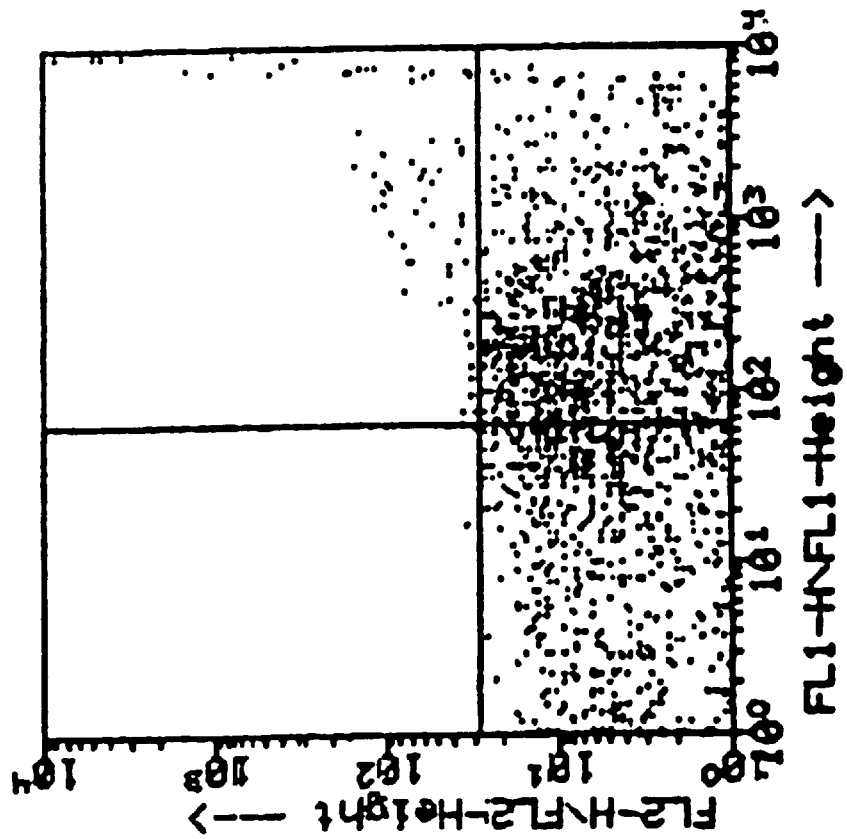

ErbB-2 down-regulation mediated by antisense oligo-nucleotides induces proliferative arrest, but not apoptosis in erbB-2 overexpressing tumor targets. In contrast, apoptosis was induced by virtue of an alternate mechanism of erbB-2 down-regulation. This suggests that erbB-2 down-regulation, per se, was not inductive of apoptosis. To determine the basis whereby the anti-erbB-2 sFv induced apoptosis, this phenomenon in a different system was reproduced. Ectopic localization of erbB-2, in non-erbB-2 transformed tumor cells, was accomplished by cotransfection of HeLa cells with wild-type human erbB-2 cDNA and the cDNA for the ER form of the anti-erbB-2 sFv. Transfection of the non-erbB-2 expressing HeLa cell line with the erbB-2 cDNA did not result in any change in cell viability, identical to that observed employing the control plasmid DNA pcDNA3. In contrast, cotransfection of the erbB-2 cDNA with the anti-erbB-2 sFv construct caused a marked cytocidal effect (FIG. 4). This cytotoxicity was also shown to be the result of induction of apoptosis as was observed in SKOV3 cells transfected with the anti-erbB-2 sFv. Thus, where erbB-2 does not contribute to the transformed phenotype, coexpression of the anti-erbB-2 sFv and heterologous erbB-2 still induced apoptosis.

The effects of the anti-erbB-2 sFv in human tumor material isolated from a patient with primary ovarian carcinoma was shown. Methods were developed to isolate primary ovarian tumor cells which maintain their viability and proliferative capacity in vitro for approximately 7–10 days. In addition, the amount of cell surface erbB-2 in these tumor explants was estimated employing an immunohistochemistry assay. To establish the biologic effects of intracellular single-chain antibody knockout of erbB-2 in primary ovarian carcinoma cells, the various anti-erbB-2 sFv constructs were delivered to cells employing the AdpL vector followed by the XTT assay for determination of cell viability. Control experiments employing a LacZ reporter gene demonstrated that >99% of the isolated human primary ovarian carcinoma cells could be transduced. The human ovarian carcinoma cell line SKOV3 was employed as a control. The ER form of the anti-erbB-2 sFv exhibited a specific cytotoxic effect in the human primary tumor cells at 96 hours post transfection.

Interestingly, the magnitude of the sFv-mediated cell killing observed in the primary tumor material was as great as that observed in the erbB-2 overexpressing cell line SKOV3. These findings strongly suggest that ovarian cancer cell lines represent appropriate models of the operative mechanisms utilized in tumor cells derived from actual patients. Thus, the sFv-mediated cytotoxicity does not represent only an in vitro phenomenon.

EXAMPLE 3

Oncoprotein ablation mediated by the anti-erbB-2 sFv accomplishes a therapeutic effect in a murine model of human ovarian carcinoma Whether human ovarian cancer cells could be selectively killed in a murine model of malignant ascites was determined. Athymic nude mice with the erbB-2 overexpressing human ovarian carcinoma line SKOV3.ip1 were engrafted. This model allows for the development of malignant ascites and peritoneal implants of neoplastic cells in a manner which parallels the human disease. For gene therapy to be of practical utility in human ovarian carcinoma, vector strategies must be capable of accomplishing direct, in situ delivery of heterologous genes to tumor in vivo.

A vector system that accomplishes efficient in situ transduction of the tumor cells found in ovarian carcinoma malignant ascites fluid was determined. For this analysis, candidate vector systems capable of achieving therapeutic levels of in vivo gene transfer were evaluated. Athymic nude mice (Balb/c) were transplanted intraperitoneally with $1 \times 10^7$ SKOV3.ip1 cells. After 48 hours, vectors were administered intraperitoneally to deliver an *E. coli* β-galactosidase reporter gene construct (lacZ) to the mobile neoplastic cells. Evaluated vector systems included adenovirus-polylysine-DNA-complexes (AdpL), liposomes (DOTAP), and a recombinant adenovirus encoding lacZ (AdCMVLacZ). Forty-eight hours after vector administration, mobile tumor cells were harvested by peritoneal lavage and analyzed for expression of the lacZ reporter gene. This was accomplished by a fluorescent activated cell sorting (FACS) double-sorting procedure (FIG. 6). The highest level of gene transfer was accomplished with the recombinant adenovirus, the transduction frequency achieved with this vector was >80%.

Figure 7:
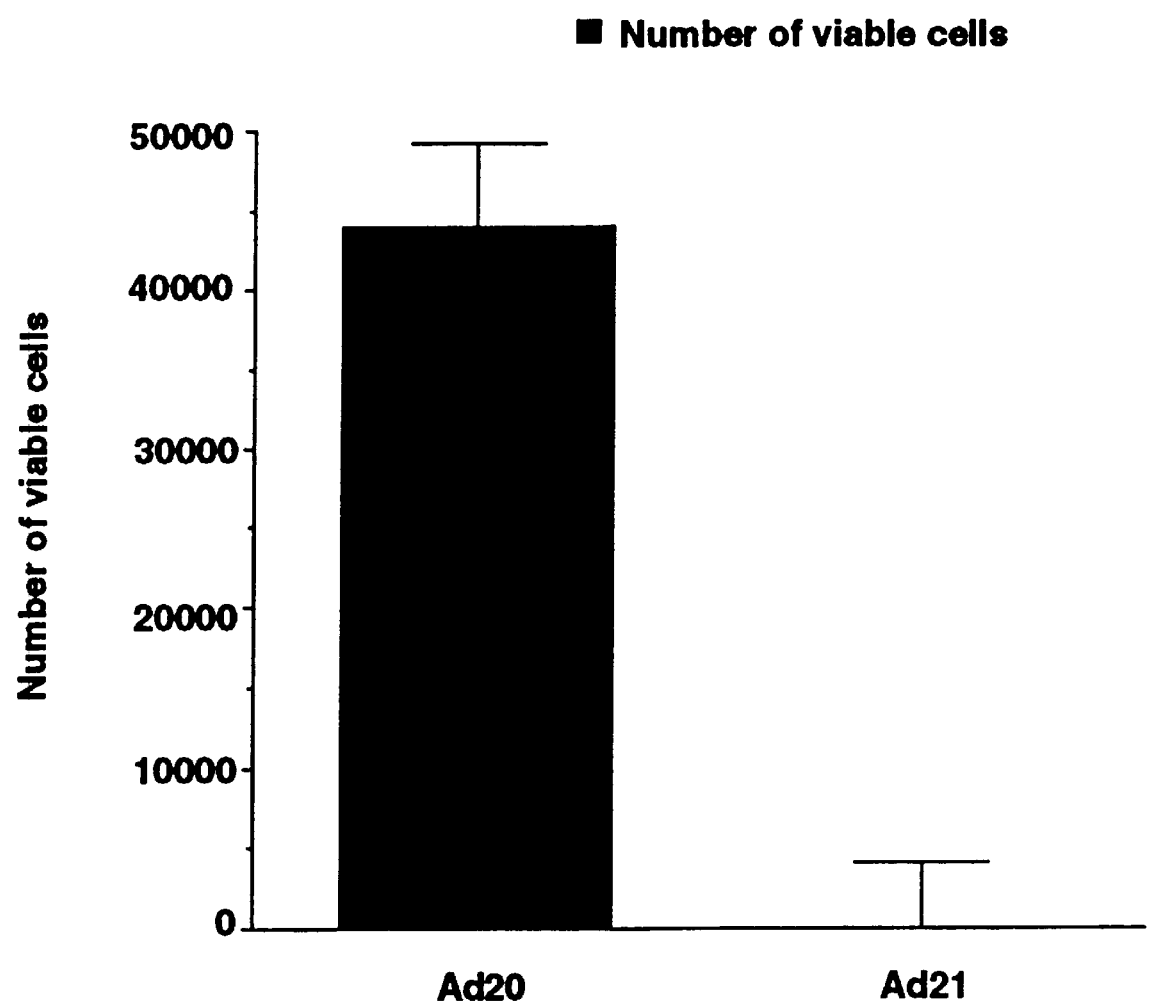
FIG. 7 shows the effect of expression of a recombinant adenovirus encoding anti-erbB-2 sFv gene on viability of erbB-2 overexpressing human ovarian tumor cells. SKOV3.ip1 cells were infected with recombinant adenovirus encoding the cytosolic or ER directed anti-erbB-2 sFvs. The XTT assay was employed to determine cell viability 96 hours post infection. This experiment was replicated 10×. Data represents mean±SEM.

As the recombinant adenovirus proved useful for in situ transduction of mobile neoplastic cells in vivo, whether the anti-erbB-2 sFv-mediated selective toxicity in this setting was determined. A recombinant adenovirus was, therefore, constructed encoding the ER form of the anti-erbB-2 sFv (Ad21) using methods of homologous recombination. The resultant virus is E1A/B deleted and, thus, replication-incompetent. Studies confirmed the structural integrity of the recombinant adenovirus genome. To establish that the anti-erbB-2 sFv gene functioned in this vector configuration, in vitro analysis was carried out employing the SKOV3.ip1 cells as the target. Cells were analyzed for viability employing the XTT assay. The anti-erb-2 sFv encoding adenovirus accomplished the same selective cytotoxicity in the erbB-2 overexpressing targets as observed with AdpL-mediated delivery (FIG. 7). Notably, the adenovirus encoding a control gene (lacZ) had no effects on cell viability, even when delivered at an identical multiplicity of infection. Thus, a replication-defective adenovirus encoding the anti-erbB-2 sFv has been constructed which retains the capacity to express an ER-anti-erbB-2 sFv. This vector can achieve selective cytotoxicity based on the encoded sFv in human ovarian carcinoma cell lines.

To demonstrate the feasibility of employing the adenoviral vector for in situ tumor cell killing via anti-erbB-2 sFv gene delivery, treatment experiments employing an orthotopic murine model were performed. As before, SKOV3.ip1 cells were xenotransplanted into athymic nude mice. Forty-eight hours after engraftment with SKOV3.ip1 cells, the SCID mice were challenged intraperitoneally with the E1A/B-deleted recombinant adenovirus encoding the anti-erbB-2 sFv (Ad21) or an E1A/B-deleted recombinant adenovirus encoding the reporter gene lacZ (AdCMVLacZ). Ninety-six hours after treatment, the animals underwent peritoneal lavage for analysis of harvested mobile tumor cells. Cells were analyzed for cell viability employing the XTT assay. The number of viable cells was dramatically decreased in the Ad21 group compared to the AdCMVLacZ group. This cytotoxicity appeared to be specifically associated with the anti-erbB-2 sFv encoding adenovirus. Analysis of the mechanism of cell death demonstrated that the Ad21 virus induced cellular apoptosis. Thus, the recombinant adenovirus encoding the anti-erbB-2 sFv was specifically cytotoxic in mobile neoplastic cells in an orthotopic murine model of human ovarian cancer.

The efficacy of the anti-erbB-2 sFv approach was established employing a murine model of human ovarian carcinoma. For this analysis, SCID mice were xenografted i.p. with $2 \times 10^7$ SKOV3.ip1 cells. After 5 days, animals were challenged by the same route with either the control adenovirus, AdCMVLacZ, or the anti-erbB-2 encoding adenovirus, Ad21, and animals monitored for survival. The anti-erbB-2 sFv encoding adenovirus, Ad21, accomplished a statistically significant survival prolongation (FIG. 8). Thus, direct in situ tumor transduction to accomplish selective tumor cell cytotoxicity via the anti-erbB-2 sFv has therapeutic utility.

The basis whereby complete disease eradication was not achieved was considered. A possible mechanism is the outgrowth of "resistant" tumor cells which no longer manifest sensitivity to anti-erbB-2 sFv-mediated cytotoxicity. Tumor cells were harvested by lavage from Ad21-treated animals at late treatment times. These cells exhibited the same magnitude of sensitivity to sFv-induced cytotoxicity as virgin cell line counterparts. Therefore, resistance to erbB-2 sFv-mediated cytotoxicity, per se, is not an operational factor in this context. Two additional considerations appear relevant. Firstly, the net gene transfer efficacy may be limiting effective cell kill. Thus, strategies to augment the efficiency of in situ gene transfer to tumor cells appears warranted. Additionally, all genetically modified tumor cells may not be effectively eradicated. Data suggestive of this phenomenon was noted in the context of the sFv-expressing stable clone derived in Table 1 and in the experiment in which transient expression of the induced cytotoxicity (FIG. 2). In these studies, a subset of tumor cells survived despite expression of the anti-erbB-2 sFv gene. Maneuvers to increase gene transfer efficiency, per se, would not be predicted to be completely efficacious. Thus, strategies are required to address the tumor cell subset which can survive, despite expression of the anti-erbB-2 sFv.

EXAMPLE 4

Efficacy of cell killing mediated by anti-erbB-2 sFv enhanced chemosensitivity in erbB-2 overexpressing human tumor cells The expression of the erbB-2 oncoprotein is a parameter which may affect tumor cell chemosensitivity. An inverse relationship between erbB-2 levels and chemosensitivity was noted in the studies of Gazdar et al. A strategy to down-regulate the erbB-2 oncoprotein enhances tumor cell chemosensitivity. As the anti-erbB-2 sFv was capable of inducing apoptotic cell death in a tumor cell subset, in those tumor cells in which sFv expression was achieved but cytotoxicity not induced, sensitivity to a second apoptotic stimulus might occur. That the anti-erbB-2 sFv directly affects tumor cell sensitivity to chemotherapeutic agents was demonstrated.

EXAMPLE 5

Plasmid Construction

Plasmids encoding a cytosolic form of the anti-erbB-2 sFv (pGT20) as well as an endoplasmic reticulum directed form of the anti-erbB-2 sFv (pGT21) have been described. The plasmid pcDNA3 (Invitrogen, San Diego, Calif.) served as a control. The phagemid pCANTAB5/sFv contains the anti-Bcl-2 sFv DNA under the control of the inducible lac promoter. This vector also encodes a peptide tag (E-tag) located at the 3' end of the sFv to allow easy immunological detection of sFv protein expression. The Bcl-2 expression plasmid pRc-CMV/hBcl-2 contains wild type human Bcl-2 under the control of the CMV promoter. The pGEX-hBcl-2 encodes the human Bcl-2. The ER-targeted vector is a derivative of the pSecTag C vector (Invitrogen, Carlsbad, Calif.). A DNA sequence encoding the c-myc peptide tag and KDEL signal was inserted between NotI and ApaI sites of pSecTag C to generate pSTCF.KDEL. The anti-Bcl-2 sFv fragments generated by SfiI/NotI digest of pCANTAB5/sFv were ligated into the SfiI/NotI sites in pSTCF.KDEL just upstream from and in-frame with the added c-myc/KDEL sequence.

The prokaryotic BAG-1 expression vector, pGEX 3X-hBAG-1, was obtained from JC Reed (Burnham Institute, La Jolla, Calif.). To construct a BAG-1 eukaryotic vector, pGEX 3X-hBAG-1 was digested with BamHI and EcoRI to release BAG-1 open reading frame (ORF), and this fragment was subcloned into BamHI/EcoRI sites of pcDNA3 (Invitrogen, Carlsbad, Calif.). The BAG-1 expression cassette is under the control of the CMV promoter in this vector. The phagemid pCANTAB5 (Pharmacia Biotech, Piscataway, N.J.) was used to clone the anti-BAG-1 sFv DNA into the SfiI/NotI sites, under the control of the IPTG-inducible lac promoter. This vector also encodes a peptide tag (E-tag) located at the carboxy terminus of the sFv to allow easy immunological detection of sFv protein expressed in bacteria. For expression in eukaryotic cells, the pCANTAB5 plasmid containing the sFv DNA cassette was digested with SfiI/NotI, and the sFv fragment was subcloned into SfiI1NotI sites of pSTCF.KDEL, an eukaryotic expression vector. The construction of pSTCF.KDEL has been described. This vector targets the expression of an sFv to the ER. Expression of the sFv ORF is driven by the CMV promoter.

EXAMPLE 6

Cell Culture and Transfection Methods

The human ovarian carcinoma cell line SKOV3 was obtained from the American Type Culture Collection (Rockville, Md.) and maintained in Dulbecco's modified Eagle's medium (DMEM, Mediatech, Herndon, Va.) supplemented with glutamine (30 mg/ml), penicillin (10 mg/ml), streptomycin (25 mg/ml), and 10% fetal calf serum (PAA Laboratories Inc. Newport Beach, Calif.) at 37° C. in a humidified 5% $CO_2$ atmosphere.

The human breast cancer cell line MCF-7, the human prostate cancer cell line DU145, and the human cervical cancer cell line HeLa were obtained from ATCC (Rockville, Md.). DU145 and MCF- 7 cells were grown in RPMI 1640 (Cellgro Mediatech, Washington, D.C.) supplemented with 10% fetal bovine serum (FBS) (Hyclone Laboratories), L-glutamine (300 $\mu$g/ml), penicillin (100 i.u./ml) and streptomycin (25 $\mu$g/ml). The 6C8 hybridoma cell line (obtained from JC Reed, The Burnham Institute, La Jolla, Calif.) was grown in RPMI 1640 supplemented with 10% FBS, oxalate/pyruvate/insulin mix (Sigma), 30 $\mu$g/ml of carboxyethyl gamma-butryic acid (Sigma), 13.6 $\mu$g/ml of hypoxanthine (Sigma), 300 $\mu$g/ml of L-glutamine and penicllin (100 i.u./ml) and streptomycin (25 $\mu$g/ml). HeLa cells were maintained and propagated in DMEM/F12 (Cellgro Mediatech) supplemented with 10% FBS, L-glutamine and penicillin/streptomycin. All cell lines were incubated at 37° C. in 5% $CO_2$. HeLa, MCF-7 and DU145 cells were transfected in 6 well plates using the adenovirus-polylysine-DNA (AdpL) complex method.

Target SKOV3 cells were transiently transfected with constructs employing the adenovirus-poly-L-lysine (AdpL) utilizing known techniques. A volume of conjugate-DNA complex (100 $\mu$l) containing 0.2 mg plasmid DNA was then delivered to the target cells in 96-well tissue culture dishes (n=6) in DMEM containing 2% FCS. Incubation was carried out for 4 hr at 37° C. after which, 100 ml of complete media was added to control cell lines and incubation continued for 72 hours. Alternatively for cisplatin treated cell lines, 4 mg/ml cis-diamminedichloroplatinum (Bristol-Myers Squibb, Princeton, N.J.) was diluted in 100 ml of complete media and added to 100 ml 2% FCS for a final concentration of CDDP at 2 mg/ml.

EXAMPLE 7

Generation of Cancer Cell Clones Stably Expressing Anti-erbB-2 sFvs

Plasmid DNAs were stably transfected into target SKOV3 cells by the lipofectAMINE (GIBCO BRL, Gaithersberg, Md.) method using conditions described by the manufacturer. To this end, both pGT20 and pGT21 contained a neomycin resistance expression cassette to allow for selection of stable transfectants. Briefly, lipid/DNA complexes consisting of 40 mg plasmid DNA were delivered to cells at ~50% confluency in 6.0 cm tissue culture dishes in a volume of 1.0 ml of OptiMEM medium (GIBCO BRL). After 18 hours, the transfection medium was removed and replaced with complete medium and incubation continued for an additional 48 hours. Cells were split into selective medium containing Geneticin (GIBCO BRL) at 1 mg/ml. Colonies were then isolated and expanded in selective medium.

EXAMPLE 8

Determination of erbB2 Expression in Stable Clones

To determine the levels of erbB-2 protein present in the aforementioned stable clones, total clonal cell extracts were obtained.

Briefly, total cellular protein was isolated from cells in a cell lysis buffer solution containing 1× physiologic buffered saline (pH-7.4), 1.5 mM EDTA, 100 mM PMSF and 1 mg/ml aprotinin. The cell lysate was then plated at 1 mg/ml in a 96 well plate pre-coated with human erbB-2 antibody and assayed according to manufacturer's instructions using a quantitative Her2/neu (erbB-2) ELISA kit (Oncogene Science, Uniondale, N.Y.). Using a peroxidase conjugate system, the presence of erbB-2 protein was determined at an absorbance of 490 nm. A standard curve was derived using the Human Neu Unit (HNU) standards provided by the manufacturer and the test absorbances were compared to the standard curve and values extrapolated using Softmax Program (BioTek Instruments, Winooski, Vt.). The neu assay will detect 10 HNU (0.5 femtomoles) per ml of cell lysate. The signal of 10 HNU standard is approximately twice the background signal. The human neu values obtained from the assay were then converted to fmole/mg protein.

EXAMPLE 9
Presence of Anti-erbB-2 sFvs in Stable SKOV3 Clones

To validate the phenotype of the stable SKOV3 clones, Western Blot analysis was carried out to verify the expression of the anti-erbB-2 sFvs. $1 \times 10^6$ cells were washed twice in PBS and solubilized in 500 ml of RIPA buffer (0.15M Tris-HCl, [pH 7.2]/1% (vol/vol) Triton X-100/0.1% (wt/vol) sodium dodecyl sulfate/1% (wt/vol) sodium deoxycholate). A volume of the cell lysate containing 20 μg total protein was added to equal volume of sample buffer (0.175 M Tris HCl pH 6.8, 20% (v/v) glycerol, 4.1% (w/v) SDS, 10% (v/v) β-mercaptoethanol, 0.002% (w/v) bromophenol blue, 6M Urea). The samples were heated to 95° C. for 5 minutes and electrophoresed by SDS/PAGE in 4–20% gradient Tris-HCl gels. Samples were transferred by electroblotting onto PVDF membranes (0.2 micron) (Bio-Rad Laboratories, Hercules, Calif.) after SDS-PAGE using a blotting buffer containing 25 mM Tris and 192 mM glycine. Non-specific binding was then blocked using 5% nonfat dry milk (NFDM) in TBS-TX (50 mM Tris pH 7.5, 100 mM NaCl, 1.0% Triton X-100) and then probed with polyclonal rabbit anti-sFv antibody diluted 1:1000 in 5% NFDM in TBS-TX. Alkaline phosphatase conjugated goat anti-rabbit IgG antibody (Jackson ImmunoResearch Labs, Inc., West Grove, Pa.) was used as secondary antibody at a 1:1000 dilution and the blot was developed in carbonate buffer pH 9.8 (0.1 M NaHCO3, 1 mM $MgCl_2$) with nitro blue tetrazolium (NBT) and bromochloroindolyl phosphate (BCIP) (Bio-Rad Laboratories).

EXAMPLE 10
Cell Proliferation Assay

For this analysis, SKOV3 cells were seeded at a density of 5000 cells/well in a 96-well plate and incubated for 24 hr. The AdpL method was employed for transient transfection of target cells with the plasmid constructs pGT21 or pcDNA3. Four hours after transfection CDDP was added at a concentration of 2 mg/ml. Alternatively, SKOV3/pGT21 clonal cells or SKOV3/pGT20 clonal cells were seeded at a density of 5000 cells/well in a 96-well plate and incubated for 24 hr. Four hours post-transfection, CDDP was then added at a concentration of 2 mg/ml. At 72 hours post-transfection, direct analysis of cell viability was measured using the Cell Titer 96 AQ Non-Radioactive Cell Proliferation Assay (Promega Corp., Madison, Wis.). This assay is based on the ability of only viable cells to reduce (3-(4,5-dimethylthiazol-2-yl)-5-(3-carboxymethoxy phenyl)-2-(4-sulfophenyl)-2H-tetrazolium (MTS) to formazan that is soluble in tissue culture medium and can be measured spectrophotometrically at an absorbance of 490 nm. MTS solution (2 ml) was mixed with 100 ml of phenazine methosulfate (PMS) immediately before addition to the cells in the culture plate. MTS/PMS solution (20 μl) was then added into each well maintaining a ratio of 20 ml MTS/PMS to 100 ml of medium. After 30 minutes, the reduction product was measured at an absorbance of 490 nm and compared to a standardized curve.

EXAMPLE 11
Determination of the Mechanism of Cell Death

The mechanism of cell death induced by expression of the anti-erbB-2 sFv and co-administration of CDDP was determined by evaluating target cells for evidence of apoptosis. Fluorescent DNA-binding dyes combined with fluorescence microscopy were employed to visualize cells demonstrating aberrant chromatin organization. For this analysis, the cell suspension was prepared at $\sim 1 \times 10^5$ cells/ml complete medium. The suspended cells (25 ml) were combined with 1 ml of dye containing 100 mg/ml acridine orange+100 mg/ml ethidium bromide and examined by fluorescent microscopy for evidence of apoptosis. Statistical analysis of calculated means was performed using the Student t-test with pooled variances. A p-value of <0.01 was considered significant.

The erbB-2-overexpressing tumor cells, SKOV3, were treated with either the anti-erbB-2 sFv (via transient transfection), the chemotherapeutic agent cisplatin (CDDP), or a combination of these agents. FIG. 9 shows that intracellular expression of the anti-erbB-2 sFv or CDDP induced cytotoxicity, but a synergistic effect was noted when the two agents were employed in combination.

Thus, the anti-erbB-2 sFv was capable of enhancing tumor cell sensitivity to a chemotherapeutic agent. An experimental model which would allow more direct analysis of the anti-erbB-2 sFv mediated chemosensitization was developed. The sFv-expressing SKOV3 clones derived in Table 1 were expanded and characterized. Clonal cell populations were thus characterized for confirmation of expression of the anti-erbB-2 sFv. In addition, clonal populations of the parent cell line (SKOV3) were chosen, as well as stable lines expressing either the cytosolic anti-erbB-2 sFv (SKOV3/GT20) or the ER anti-erbB-2 sFv (SKOV3/GT21) which exhibited comparable growth kinetics. The parental clone and the cytosolic sFv clone would likely have comparable levels of cellular erbB-2. In addition, the ER sFv clone would likely reduce cellular erbB-2, based upon a level of sFv-mediated erbB-2 down-regulation. These clones were thus evaluated for cellular erbB-2 by direct ELISA analysis (FIG. 10). It could be seen that the ER anti-erbB-2 sFv clone, SKOV3/GT21, was uniquely characterized by reduced erbB-2 levels.

These clonal cell populations were further evaluated for their sensitivity to the chemotherapeutic agent CDDP. The cytosolic sFv expressing clone, SKOV3/GT20, did not differ in CDDP sensitivity when compared to the parental clone SKOV3. Thus, intracellular expression of the anti-erbB-2 sFv in the cellular cytosol has no effect on either erbB-2 levels (FIG. 10) or sensitivity to CDDP (FIGS. 10 and 11). In marked contrast, the clonal population expressing the ER form of the anti-erbB-2 sFv exhibited significantly greater sensitivity to CDDP treatment than the parental clone. In this instance, the ER-sFv-mediated erbB-2 down-regulation was associated with enhanced chemosensitivity.

The present invention demonstrates that erbB-2 down-regulation is a means to achieve enhanced chemosensitivity in erbB-2-overexpressing tumor cells. In addition, these findings address the issue of intracellular antibody-expressing tumor cells not directly killed by the anti-erbB-2 sFv. These cells are phenotypically altered by the sFv-mediated down-regulation. In this instance, they are thus rendered susceptible to a second apoptosis-inducing insult.

EXAMPLE 12
The parameters that modulate chemosensitivity induced by intracellular expression of an anti-erbB-2 sFv To achieve functional ablation of the erbB-2 oncoprotein, an intracellular antibody knockout strategy was developed. The newly synthesized erbB-2 is entrapped during synthesis by the ER-localized anti-erbB-2 sFv. Since it would not be able to achieve its normal cell surface localization, it would not be capable of interacting with its cognate ligand and thus could not transduce a signal to elicit cellular proliferation. One would expect that this form of intervention would elicit a proliferative arrest selectively in erbB-2 positive cells. Unexpectedly, however, it was found that this genetic intervention was actually cytocidal to erbB-2 overexpressing tumors. Further, the mechanism of cell death could be shown to be on the basis of induced apoptosis. Experiments in heterologous cells demonstrated that this phenomenon was not on the basis of "shut-off" of transforming signals, but rather was linked to the co-expression of erbB-2 and the anti-erbB-2 sFv in target tumor cells. The sFv-mediated erbB-2 down-regulation enhanced chemosensitivity in erbB-2 tumors. From the standpoint of a gene therapy strategy, this was a very desirable result, in that tumor cells were selectively killed on the basis of a targeted tumor marker. Thus, this cytotoxicity could be accomplished in a targeted manner whereby non-erbB-2 positive cells were not induced to undergo apoptosis. In these instances where direct cytotoxicity could not be fully accomplished, the sFv rendered tumor cells more sensitive to a second apoptotic insult.

EXAMPLE 13
Level of anti-erbB-2 sFv expression as a determinant of the efficacy of chemosensitization The coexpression of erbB-2 and the anti-erbB-2 sFv in heterologous cells could induce selective toxicity by cotransduction of cells with erbB-2 and the anti-erbB-2 sFv (FIG. 4). This suggested that it was not abrogation of the transforming event(s), but ER entrapment of erbB-2, per se, which induced apoptosis. This cotransduction system is employed to define the dose-response relationship between expression of erbB-2, the anti-erbB-2 sFv and induced chemosensitivity. AdpL complexes are constituted with various ratios of anti-erbB-2 sFv plasmid and erbB-2 plasmid (sFv:erbB-2 gene copy number: 10:1, 8:1, 4:1, 2:1, 1:1, 1:2, 1:4, 1:8, 1: 10). The complexes are then used to cotransduce the non-erbB-2 expressing cell line HeLa with analysis carried out to determine the magnitude of the induced chemosensitivity in these cells with the various chemotherapeutic agents. A relationship can thus be defined between the input anti-erbB-2 sFv and erbB-2 plasmids and the observed chemosensitivity.

EXAMPLE 14
Other single chain antibodies targeting gene products

The present invention demonstrated that sFv-mediated knockout of the overexpressed erbB-2 growth factor receptor enhanced tumor cell chemosensitivity. A person having ordinary skill in this art would readily recognize that other overexpressed cell surface markers are associated with the progression of human ovarian carcinoma. Overexpression of these markers, such as EGFR, have been associated with enhanced chemoresistance, in a manner analogous to erbB-2.

First, erbB-2 positive ovarian tumors represent a minority of the overall ovarian carcinoma population. The development of sFvs targeting other ovarian carcinoma related targets is within the skill of those having ordinary skill in this art given the teachings of the present invention. In addition to this therapeutic consideration, in many of the aforementioned contexts whereby cell surface receptor overexpression can be correlated with ovarian carcinoma, its precise association with the chemoresistant phenotype has not been clearly established. Thus, the achievement of functional knockout of these targets would establish a phenotypic link.

EXAMPLE 15
Down-regulation of analogous transforming transmembrane growth factors via intracellular sFvs and induction of chemosensitivity EGFR is overexpressed in a variety of epithelial tumors, including those originating in lung and breast. Its overexpression has been shown to be a key event in neoplastic transformation and progression. In addition, overexpression of this analogous tyrosine kinase receptor has been linked to tumor cell chemoresistance. sFv mediated down-regulation of the EGFR can be accomplished to elicit cellular chemosensitivity. An anti-EGFR sFv is modified to achieve ER localization after expression in an eucaryotic vector. Cotransduction of heterologous non-EGFR expressing cells with the human EGFR cDNA and the anti-EGFR sFv is then performed. Cells are evaluated for chemosensitization employing the XTT assay. In addition, stable clones expressing the anti-EGFR sFvs (cytosolic and ER) are derived. Clonal populations of ovarian carcinoma cell lines are then evaluated for expression of the sFv, growth kinetics and down-regulation of the EGFR oncoprotein. These clones were evaluated for sensitivity to chemo therapeutic agents as described in FIGS. 10 and 11.

EXAMPLE 16
Vector reagents for the sFv/chemosensitization strategy

In these studies, the recombinant adenoviral vector exhibited the highest in situ gene transfer capacity of the tested vectors. These results parallel the findings of others whereby recombinant adenovirus has been employed to accomplish in situ transduction of tumor within the peritoneum. RAC-approved clinical human gene therapy protocols have proposed the employment of recombinant adenovirus for the delivery of tumor suppressor genes for lung cancer and squamous carcinoma of the head and neck, as well as in molecular chemotherapy strategies to deliver the HSVTK gene for CNS tumors and mesothelioma.

Adenoviral vectors can be used for in situ gene transfer to cancer cells. A number of replication-defective recombinant adenoviral vectors have been approved for human use in the context of RAC-approved protocols relating to human ovarian carcinoma. For the present context, the various sFvs directed against ovarian cancer markers can be configured into adenoviral vectors employed. Liposome vectors can be used to accomplish in situ gene transfer to ovarian cancer cells. Liposome gene transfer vectors offer a number of potential advantages required for the sFv-knockout gene therapy strategy, including low immunogenicity and repetitive in vivo gene delivery. These vectors can achieve direct in vivo gene delivery in target organs and tissues such as the lung, liver and vasculature.

EXAMPLE 17
Enhancement of tumor response to radiation therapy using gene therapy by intracellular ablation Targeted eradication of the erbB-2 oncoprotein using gene constructs encoding anti-erbB-2 intracellular single chain antibodies kills tumor cells. In addition, this gene therapy strategy was shown to induce enhanced tumor cell chemosensitivity. The present invention further demonstrates improved tumor therapy as a result of the combination of this gene therapy approach and radiation therapy treatment. This combination of gene therapy knockout of an oncoprotein and radiation therapy treatment possesses the advantage of targeted gene therapy mediated radiation sensitization of tumors resulting in improved tumor cures following treatment with radiation therapy.

FIG. 12 shows the effect of single fraction cobalt-60 external beam irradiation on the growth of established human ovarian cancer xenografts. On day −6, a group of 5 athymic nude mice were injected subcutaneously with $1 \times 10^7$ SKOV3.ip1 human ovarian cancer cells, and 10 athymic nude mice were injected subcutaneously with $1 \times 10^7$ SKOV3-KO (SKOV3.ip1 cells transduced with a gene encoding single chain anti-erbB-2 antibody designated SKOV3/pGT21). On day 0, when the tumors measured 4–8 mm in diameter, all of the SKOV3.ip1 tumors and 5 of the tumors in animals injected with SKOV3-KO cells received 10 Gy irradiation. Five of the animals with SKOV3-KO tumors were not irradiated. The change in tumor size (bidimensional product) was then assessed at varying times after injection. Data are expressed as the average of 5 animals/group.

FIG. 12 and Table I shows the differential regrowth delay of the tumors treated with radiation and expressing or not expressing the anti-erbB-2 sFv. As shown in the FIG. 12, those animals with the anti-erbB-2 sFv SKOV3/pGT21 tumors and irradiation had the greatest tumor regression rate and tumor regrowth delay compared to the other groups. The tumors from SKOV3/pGT21 cells that did not receive radiation grew initially then regressed for approximately 40 days before rapid regrowth similar to the parental SKOV3.ip1 cells with 10 Gy irradiation. The SKOV3/pGT21 tumors with irradiation had rapid regrowth after 90–100 days. This data shows that cells with down-regulated erbB-2 mediated by the anti-erbB-2 sFv are more susceptible to the effects of ionizing radiation than cells that maintain their erbB-2 expression.

TABLE I

| Animal No. | Cells/AB Death Day | Tumor Regression | Recurrence | Comments |
| --- | --- | --- | --- | --- |
| 1 | SAC'D D-168 | 20 | | SKOV3-KO + 10 GY |
| 2 | SAC'D D-168 | 36 | | SKOV3-KO + 10 GY |
| 3 | SAC'D D-118 | 36 | 71 | SKOV3-KO + 10 GY |
| 4 | SAC'D D-164 | 20 | 99 | SKOV3-KO + 10 GY |
| 5 | SAC'D D-168 | 36 | 71 | SKOV3-KO + 10 GY |
| 6 | SAC'D D-101 | 10 | 43 | SKOV3-KO + 0 GY |
| 7 | SAC'D D-77 | | | SKOV3-KO + 0 GY |
| 8 | SAC'D D-71 | 8 | 45 | SKOV3-KO + 0 GY |
| 9 | SAC'D D-77 | | | SKOV3-KO + 0 GY |
| 10 | SAC'D D-129 | 22 | 43 | SKOV3-KO + 0 GY |
| 11 | SAC'D D-115 | 43 | 55 | SKOV3-ip1 + 10 GY |
| 12 | SAC'D D-48 | | | SKOV3-ip1 + 10 GY |
| 13 | SAC'D D-125 | | | SKOV3-ip1 + 10 GY |
| 14 | SAC'D D-129 | | | SKOV3-ip1 + 10 GY |
| 15 | SAC'D D-129 | | | SKOV3-ip1 + 10 GY |

Time of animal death or sacrifice due to large tumor size, tumor regression, and tumor recurrence in athymic nude mice injected subcutaneously with SKOV3.ip1 or SKOV3-KO cells. Some of the tumors were irradiated with 10 Gy cobalt-60 irradiation on day 0.

FIG. 13 shows the effect of single fraction cobalt-60 external beam irradiation on the growth of established human ovarian cancer xenografts. On day −8, a group of 10 athymic nude mice were injected subcutaneously with $1.5 \times 10^7$ SKOV3.ip1 or $2.0 \times 10^7$ SKOV3-KO human ovarian cancer cells SKOV3.ip1 cells transduced with a gene encoding single chain anti-erbB-2 antibody designated SKOV3/pGT21. On day 0, when the tumors measured 3–7.5 mm in diameter, 5 animals from each group received 10 Gy cobalt-60 irradiation. The other tumors were not irradiated. The change in tumor size (bidimensional product) was then assessed at varying times after injection. Data are expressed as the average of 5 animals/group.

TABLE II

| Animal No. | Cells/AB Death Day | Tumor Regression | Recurrence | Comments |
| --- | --- | --- | --- | --- |
| 1 | SAC'D D-67 | | | SKOV3-ip1 + Co-60 |
| 2 | SAC'D D-82 | | | SKOV3-ip1 + Co-60 |
| 3 | SAC'D D-67 | | | SKOV3-ip1 + Co-60 |
| 4 | SAC'D D-82 | | | SKOV3-ip1 + Co-60 |
| 5 | SAC'D D-67 | | | SKOV3-ip1 + Co-60 |
| 6 | SAC'D D-62 | | | SKOV3-ip1 |
| 7 | SAC'D D-62 | | | SKOV3-ip1 |
| 8 | SAC'D D-67 | | | SKOV3-ip1 |
| 9 | SAC'D D-67 | | | SKOV3-ip1 |
| 10 | SAC'D D-67 | | | SKOV3-ip1 |
| 11 | SAC'D D-82 | | | SKOV3-KO + Co-60 |
| 12 | SAC'D D-82 | 37 | 55 | SKOV3-KO + Co-60 |
| 13 | SAC'D D-82 | 37 | 55 | SKOV3-KO + Co-60 |
| 14 | SAC'D D-82 | 15 | | SKOV3-KO + Co-60 |
| 15 | SAC'D D-82 | 15 | 55 | SKOV3-KO + Co-60 |
| 16 | SAC'D D-82 | 13 | | SKOV3-KO + |
| 17 | SAC'D D-82 | 13 | | SKOV3-KO + |
| 18 | SAC'D D-67 | 13 | 34 | SKOV3-KO + |
| 19 | SAC'D D-62 | 13 | 34 | SKOV3-KO + |

Time of animal death or sacrifice due to large tumor size, tumor regression, and tumor recurrence in athymic nude mice injected subcutaneously with SKOV3.ip1 or SKOV3-KO cells. Some of the tumors were irradiated with 10 Gy cobalt-60 irradiation on day 0.

To confirm the finding that radiation interacts with the anti-erbB-2 sFv to radiosensitize SKOV3/pGT21 tumors (FIG. 13 and Table I), the above experiment were repeated with additional controls. Previously, tumors established with SKOV3.ip1 parental cells received radiation; there was no group of the parental cells that did not receive radiation. SKOV3.ip1 parental cells without irradiation continued to grow without the delay observed with SKOV3/pGT21 tumors (FIG. 13 and Table II). The results of the repeat experiment were very similar to the first experiment out to 70 days. The same result in two independent experiments supports the conclusion that radiation interacts with the down-regulated erbB-2 expression in SKOV3/pGT21 cells to lead to enhanced cell killing with ionizing radiation.

EXAMPLE 18

Derivation of anti-Bcl-2 and anti-BAG-1 sFvs constructs

The murine hybridoma cell line 4D7, which expresses a monoclonal antibody against the human Bcl-2 protein was described. The murine hybridoma cell line 6C8 expresses a monoclonal antibody against the human BAG-1 protein (from John C Reed, Burnham Institute, La Jolla, Calif.). This hybridoma was used to generate cDNA from purified mRNA. sFv constructs were generated with the recombinant phage antibody system (Pharmacia Biotech, Piscataway, N.J.) according to the manufacturer's instructions. Briefly, the variable heavy ($V_H$) and variable light ($V_L$) chains were amplified from the cDNA by polymerase chain reaction (PCR) using mouse variable region primers (Pharmacia Biotech, Piscataway, N.J.). The $V_H$ and the $V_L$ DNA fragments were linked together by overlap extension PCR using a $(Gly_4Ser)_3$ linker to generate a 750 bp sFv construct with flanking SfiI and NotI restriction sites. The sFv DNA fragments were cloned into SfiI/NotI sites of the prokaryotic expression vector pCANTAB5 (Pharmacia Biotech, Piscataway, N.J.). Screening of recombinant clones expressing an sFv against Bcl-2 or BAG-1 was accomplished by colony lift assay, as described. BAG-1 ORF was cloned into BamHI/EcoRI of the pGEX 3X (Pharmacia Biotech) vector encoding the Glutathion-S-transferase (GST) protein. The GST-BAG-1 fusion protein was purified using the GST purification module kit from Pharmacia Biotech.

EXAMPLE 19
Western blot, ELISA and Cytotoxicity assays

At 48 hours post-transfection, cells were lyzed using Promega lysis buffer (Promega, Madison, Wis.). Protein concentration was measured by the Bradford method using the Bio-Rad protein assay (BioRad, Hercules, Calif.). Equal amounts of protein (30 µg) were loaded in each lane and run on 12% SDS-PAGE gels. The same gel was also stained with Coomasie Blue to verify that similar amounts of protein were loaded in each lane. After transfer onto PVDF membrane (Bio-Rad, Hercules, Calif.), the membranes were probed with either an anti-BAG-1 antibody (purified from the 6C8 hybridoma cell line, 1:1000 dilution), an anti-c-myc tag antibody (1:10000, Invitrogen) or an anti-Bcl-2 antibody (1:1000; Dako, Carpinteria, Calif.). An HRP-conjugated rabbit anti-mouse antibody (Jackson ImmunoResearch, West Grove, Pa.) was used at 1:10000. The immunoblots were developed by chemiluminescence using the Renaissance system according to the instructions of the manufacturer (Dupont, Boston, Mass.).

The periplasmic extracts were prepared as follows: bacterial clones containing pCANTAB5/sFvs were induced with 1 mM IPTG for 4 hours, centrifuged and resuspended in ice-cold phosphate buffered saline (PBS)-1 mM EDTA, followed by incubation on ice for 30 minutes and centrifugation at 1500g for 10 minutes at 40C. The supernatant, which contains the soluble sFvs, was stored at 4° C. until needed. Ninety-six well plates were coated with 10 µg/ml of purified BAG-1 protein (200 µl/well) in PBS pH 7.4 or Bcl-2 protein (10 µg/ml) and incubated overnight at 4° C. The plates were blocked for 1 hour with 3% bovine serum albumin (Boehringer Mannheim Co, Indianapolis, Ind.) at room temperature and then incubated with increasing concentrations of periplasmic extracts in a constant volume of 200 µl for 1 hour. After washing with PBS, the plates were incubated at room temperature for 1 hour with 200 µl of horseradish peroxidase (HRP) conjugated anti-Etag antibody (1:8000 dilution, Pharmacia Biotech). The plates were developed with ABTS chromogen reagent (Pharmacia Biotech) and read on a microplate reader at 410 nm.

Cells were transfected in 6 well plates using the AdpL method and replated the next day into 96 well plates ($10^4$ cells/well). Twenty-four hours later, the medium was changed and fresh medium containing various concentrations of staurosporine (Sigma) or cis-diamminedichloroplatinum (CDDP) was added. The relative percentage of viable cells was determined 4 days later by (3-(4,5-dimethylthiazol-2yl)-5-(3-carboxymethoxyphenyl)-2-(4-sulfophenyl)-2H tetrazolium (MTS) reduction assay using the Celltiter 96 kit (Promega, Madison, Wis.).

EXAMPLE 20
Construction and binding activity of anti-Bcl-2 sFvs to Bcl-2

Figure 15B:
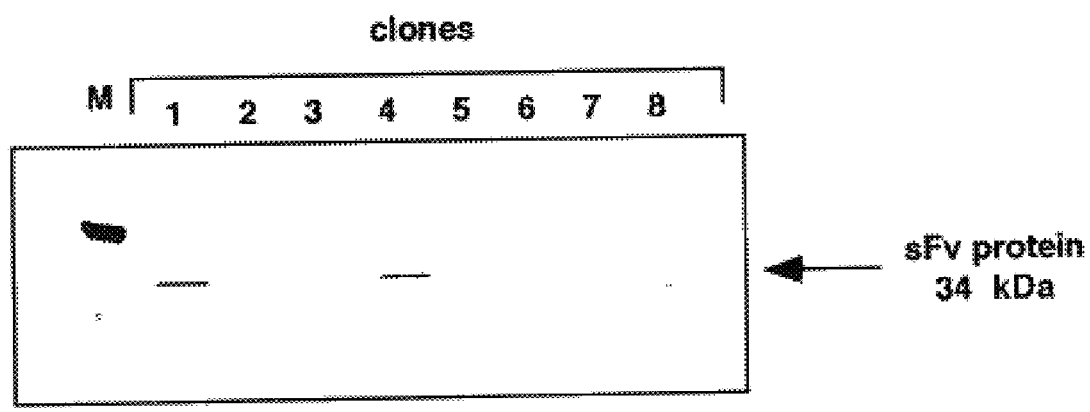

The hybridoma cell line 4D7 (from John C Reed) produces a monoclonal antibody against the human Bcl-2 protein. The cDNA encoding the $V_H$ and the $V_L$ chains of this antibody were linked together as described and the full length sFv construct was cloned into the bacterial expression vector pCANTAB5 (FIG. 14A). Following screening by colony lift assay, positive clones were analyzed by PCR for the presence of an sFv insert (FIG. 15A) and for their ability to generate an ~34 kDa sFv protein by Western blot (FIG. 15B). All the clones tested by PCR displayed the expected 750 bp sFv DNA fragment (with the exception of #7) but only two clones, #1 and #4, had detectable expression of anti-Bcl-2 sFv proteins. These two clones were further studied for their binding affinity to the Bcl-2 protein.

To determine the relative binding affinities of the anti-Bcl-2 sFvs #1 and #4, periplasmic extracts produced from IPTG-induced E. coli were prepared. These extracts, which contain soluble sFv proteins, were then used in an enzyme-linked immunosorbent assay (ELISA) to determine their ability to bind to Bcl-2 protein. The untransduced strain and an irrelevant protein (BAG-1) were used as negative controls to confirm the binding specificity. In this analysis, both anti-Bcl-2 sFv #1 and #4 specifically bound to the Bcl-2 protein (FIG. 16) whereas no binding was observed to an untransduced periplasmic extract or the BAG-1 protein (results not shown). The specific binding affinity of the anti-Bcl-2 sFv #4 was higher, especially at high concentrations. Thus, an anti-Bcl-2 sFv has been derived, that, when expressed in a prokaryotic system, binds specifically to the human Bcl-2 protein.

EXAMPLE 21
Intracellular expression of the anti-Bcl-2 sFv in eukaryotic cells

The intracellular expression of sFvs is a potent way to achieve selective knock-out of cellular proteins. As Bcl-2 is a membrane associated protein, and previous experience has shown that sFvs directed to the ER where antibodies are normally folded, are stable and properly folded, an eukaryotic expression vector was constructed that could target the anti-Bcl-2 sFv to the ER. To this end, the pSecTag C vector (Invitrogen), which includes an Ig kappa leader sequence directing proteins to the secretory pathway, was modified to include the KDEL signal at the carboxy terminal of the sFv in order to localize the anti-Bcl-2 sFv to the ER. The integrity of this vector was verified by DNA sequencing. Its ability to target the green fluorescent protein (GFP) to the correct subcellular compartment was determined in transient transfection assays. In these experiments, HeLa cells were transduced using the (AdpL) method as described, and 48 hours after transfection the cells were examined for immunofluorescence. The immunofluorescence pattern reveals a punctate, mostly perinuclear distribution consistent with localization to targeted organelles.

To determine if the anti-Bcl-2 sFvs could be expressed in eucaryotic cells, HeLa cells were transduced using the AdpL method (>90% transduction efficiency in these cells, and analyzed them 48 hours later for sFv expression by Western blot. For these experiments, the anti-Bcl-2 sFv #1 and #4 were introduced into the pSTCF.KDEL vector. The integrity of these new recombinant plasmids was verified by DNA sequencing. As shown in FIG. 17A, both c-myc epitope-tagged anti-Bcl-2 sFvs were expressed at high level when cloned into the ER-targeted vector construct. Therefore, as expected, high level expression of the ER-targeted anti-Bcl-2 sFvs was achieved in this transient eucaryotic system.

EXAMPLE 22
Inhibition of Bcl-2 expression by an ER-targeted anti-Bcl-2 sFv in HeLa cells following cotransfection with a Bcl-2 expression vector To show the functional activity of the anti-Bcl-2 sFvs, a heterologous system was used in which the Bcl-2 protein could be exogenously introduced into cells that are highly transducible by the AdpL vector system. The anti-Bcl-2 sFvs, or the vector DNA (control), cotransfected with pRC/CMV/hBcl-2 in HeLa cells, were evaluated for their ability to modulate expression of Bcl-2. Forty-eight hours post-transfection, the cells were lysed and Bcl-2 expression was determined by Western blot. A duplicate gel was also stained with coomasie to ensure that the same amount of protein was loaded in each lane. Compared to control, both anti-Bcl-2 sFv #1 and #4 significantly reduced Bcl-2 expression, although clone #4 was more efficient (FIG. 17B). This observation is consistent with the fact that the anti-Bcl-2 sFv #4 demonstrated higher binding affinity to Bcl-2 in the ELISA (FIG. 16). Therefore, the present invention shows that intracellular expression of an anti-Bcl-2 sFv is capable of efficiently down-regulated the Bcl-2 protein in eukaryotic cells.

To further evaluate the specificity of this effect, Bcl-2 expression in HeLa cells was assayed for a dose-dependent modulation. A series of different DNA ratios (1:1, 1:5, 1:10) of pRC/CMV/hBcl-2 and anti-Bcl-2 sFvs plasmids were cotransfected into HeLa cells. Bcl-2 expression was determined 48 hours post-transfection by Western blot. As shown in FIG. 18, a more pronounced down-modulation of Bcl-2 expression was observed with increasing amounts of anti-Bcl-2 sFv DNA, thereby suggesting that, in this system, a relative excess of sFv protein is required for optimal antigen interaction and ablation. The dose-response observed also supports the hypothesis that a specific interaction occurs between the anti-Bcl-2 sFv and Bcl-2 protein. As previously observed, the anti-Bcl-2 #4 was the most efficent to down-regulate Bcl-2.

EXAMPLE 23

Modulation of Bcl-2 in breast and prostate cancer cells expressing Bcl-2

It was next evaluated whether the anti-Bcl-2 sFv #4 could also modulate Bcl-2 expression in the breast cancer cell line MCF-7. These cells are highly transducible by the AdpL method, expresses Bcl-2, and studies have shown that increased cell survival to cytotoxic drugs is dependent on Bcl-2 expression. Therefore, inhibition of Bcl-2 function would be expected to augment the sensititivity of MCF-7 cells to apoptotic stimuli. To verify this, the anti-Bcl-2 sFv #4 was introduced into MCF-7 cells and the level of the Bcl-2 protein was determined. Compared to the control, a markedly decreased Bcl-2 expression level was noted in cells that received the anti-Bcl-2 sFv (FIG. 19A). A similar effect was seen in the prostate cancer cell line DU145, when Bcl-2 was exogenously introduced. In this case, although the level of Bcl-2 protein was higher than in endogenously Bcl-2 expressing MCF-7 cells, the anti-Bcl-2 sFv was nonetheless able to achieve significant down-modulation of the Bcl-2 protein.

To verify that the down-modulation of Bcl-2 correlated with adequate expression of the anti-Bcl-2 sFv in these cells, the cell lysates were submitted to a Western blot probed with an anti-cmyc tag antibody. As shown in FIG. 19B, adequate expression of the anti-Bcl-2 sFv protein was found in both cell lines, although DU145 cells expressed higher levels, despite the fact that equal amounts of total protein were analysed. Similar observations have been noted with other sFvs when transfected into different cell lines. In addition, both cell lines have comparable transduction efficiency with the AdpL vector system (results not shown). Taken together, these results demonstrate that intracellular expression of an ER-targeted form of the anti-Bcl-2 sFv is capable of effective down-modulation of endogenously expressed Bcl-2 or when Bcl-2 is exogenously introduced, confirming the previous data obtained in HeLa cells.

EXAMPLE 24

The intracellular expression of an anti-Bcl-2 sFv results in marked increases in drug-induced cell death in Bcl-2 expressing cells In order to examine the effects of sFv-induced down-regulation of Bcl-2 on the proliferation of human tumor cells, endogenously Bcl-2 expressing MCF-7 cells were transfected with the anti-Bcl-2 sFv plasmid or pSTCF.KDEL, as a control, and cellular proliferation was measured at several time points post-transfection by MTT assay. In addition, Bcl-2 negative DU145 cells were also transfected with the same plasmids to serve as a control. The growth curves of these cells are shown in FIGS. 20A and B. No growth inhibition was observed in cells transduced with the anti-Bcl-2 sFv compared to controls. These results suggest that, in this transient assay system, inhibition of Bcl-2 protein expression does not significantly affect the proliferation of Bcl-2 overexpressing cells under normal growth conditions. This is consistent with recent data whereby modulation of Bcl-2 levels does not affect the proliferation of epithelial tumor cell lines.

As Bcl-2 expression can modulate the sensitivity of cancer cells to drug-induced apoptosis, the relative sensitivity of Bcl-2 expressing and non-expressing cells to CDDP or staurosporine-induced cell killing was explored. Staurosporine is known to inhibit protein kinase activity and can therefore induce apoptosis in Bcl-2 overexpressing cells. As shown in FIG. 21A, MCF-7 cells transduced with the anti-Bcl-2 sFv were more susceptible to cell killing induced by staurosporine. A similar effect was observed when these cells were treated with CDDP. In contrast, Bcl-2 negative DU145 cells transfected with the anti-Bcl-2 sFv did not show any increase in cell death. In addition, when Bcl-2 was introduced by gene transfer in DU145, the cells became more resistant to CDDP-induced apoptosis as expected. However, this relative protection from cell death was abrogated when the anti-Bcl-2 sFv was co-tranfected into these cells (FIG. 21B) providing further evidence that the anti-Bcl-2 sFv can enhance drug-mediated cell death in different cell types expressing Bcl-2. Since staurosporine was relatively inefficient to kill DU145 cells, no additional protection from apoptosis was observed following transfection of pRC/CMV/hBcl-2. Nonetheless, the present invention has demonstrated that the anti-Bcl-2 sFv #4 can clearly potentiate drug-mediated cell killing in different tumor cell lines and that this effect was oberved with at least two different drugs.

EXAMPLE 25

Gene transfer of BAG-1 into tumor cells has anti-apoptotic activity

BAG-1 is a 29 kDa molecule that does not show homology to the Bcl-2 family, but the N-terminal shares homology with ubiquitin. The cDNA encoding BAG-1 was cloned in the mammalian expression vector pcDNA3 in which the expression of BAG-1 is driven by the CMV promoter. The resulting plasmid (pcDNA3/BAG-1) or control DNA (pcDNA3) was transfected into the DU145 cell line, that does not endogenously express Bcl-2, and in the MCF-7 cell line which overexpresses Bcl-2. Forty-eight hours after transfection of the BAG-1 vector, the expression of BAG-1 and Bcl-2 in both cell lines were analysed by Western blot using mouse anti-BAG-1 and anti-Bcl-2 monoclonal antibodies. As expected, expression of Bcl-2 was detected only in MCF-7 (FIGS. 22C–D), whereas high level of BAG-1 expression was found in both cell lines that received the BAG-1 vector (FIGS. 22A–B). DU145 and MCF-7 cells transfected with the control plasmid had no detectable level of BAG-1 expression. In addition, gene transfer-mediated expression of BAG-1 did not influence the level of Bcl-2 expression in MCF-7 cells as the same level of Bcl-2 protein was detected in MCF-7 cells transduced with pcDNA3 or pcDNA3/BAG-1 (FIG. 22D). Thus, the present invention demonstrates that high transient expression of the BAG-1 protein can be induced in these human tumor cell lines.

It was next evaluated if BAG-1 alone, or coexpressed with Bcl-2, could affect the sensitivity of DU145 or MCF-7 cells to drug-induced apoptosis. As shown in FIGS. 23A–B, AdpL-mediated gene transfer of BAG-1 into DU145 cells, a Bcl-2 negative cell line, had no apparent effect on their sensitivity to staurosporine-induced cytotoxocity. Staurosporine is a well know inhibitor of protein kinases. In contrast, transfection of BAG-1 in MCF-7 cells resulted in increased resistance of these cells to cell killing induced by staurosporine. Although the level of staurosporine-mediated cytotoxicity was fairly low (only ~20% killing at 150 ng/ml) in DU145, it is unlikely that the absence of any protection seen in these cells was related to this low percentage of killng. In fact, similar results were obtained when cytotoxicity was induced using CDDP. Gene transfer of BAG-1 in DU145 cells had no protective effect from CDDP-induced cell killing, even if the majority of the cells were killed, whereas MCF-7 transfected with BAG-1 showed significant protection from cytotoxity induced by CDDP compared to control. Taken together, these results suggest that BAG-1 alone has little effect on drug-mediated cell killing (at least in the prostate cancer cell line DU145) whereas in endogenously Bcl-2 overexpressing MCF-7 cells, BAG-1 can potentiate the anti-apoptotic effect of Bcl-2.

EXAMPLE 26

Single-chain antibody (sFv) as a means to abrogate the expression of BAG-1 in human tumor cell lines Intracellular sFvs represent a class of therapeutic agents that can selectively abrogate the expression of an oncogene wihthin a tumor cell. An sFv directed against the antiapoptotic protein, Bcl-2, modulated the expression of Bcl-2 and enhanced drug-induced cell killing in human tumor cells overexpressing Bcl-2. To show that an anti-BAG-1 sFv has similar properties in BAG-1 overexpressing tumor cells, an anti-BAG-1 sFv was constructed and evaluated for its binding affinity to BAG-1 by ELISA. The $V_H$ and $V_L$ chains were amplified by PCR from cDNA derived from the hybridoma cell line 6C8 (obtained from J. Reed, Burham Institute, LaJolla, Calif.), which produces a murine monoclonal against the human BAG-1 protein. The $V_H$ and $V_L$ were then joined together using the small 15 amino-acid linker $(Gly_4Ser)_3$ as described above. This sFv construct was cloned down-stream of the IPTG-inducible lac promoter in the prokaryotic expression vector pCANTAB5, transferred into the E. coli strain HB 2151 and bacterial clones were screened, based upon their ability to produce an anti-BAG-1 sFv that binds to BAG-1. Twenty positive clones were selected and further evaluated in regard to their sFv expression. FIG. 24A shows a Western blot analysis for nine of them. The binding affinity of the 20 clones to the BAG-1 protein was determined by ELISA. In this analysis, anti-BAG-1 sFv clones displayed good binding affinity to BAG-1. In contrast, no binding was observed with the bacterial extract alone or with purified Bcl-2 protein demonstrating the specificity of these sFvs for BAG-1. FIG. 24B shows the binding affinity data for three anti-BAG-1 clones that demonstrated the highest affinity.

BAG-1 is a cytosolic protein, as shown by immunofluorescence studies, and it lacks a transmembrane signal domain. Despite this fact, the anti-BAG-1 sFv was targeted to the ER because 1) most of the previous experiments performed with intracellular sFvs have been carried out in the ER; 2) antibodies are normally assembled and folded in the ER; 3) sFvs expressed in the cytosol are unstable due to an unfavorable redox environment. In addition, ER-targeted sFv have functionally inhibited proteins that were localized into other cellular compartments.

To assess the ability of the anti-BAG-1 sFvs to modulate the expression of BAG-1 in eukaryotic cells, the anti-BAG-1 sFv ORFs from clones 11, 15 and 20 were subcloned into the pSTCF.KDEL eukaryotic vector. These clones were selected based upon their binding affinity on ELISA. The ability of the pSTCF.KDEL plasmid to localize an sFv to the endoplasmic reticulum (ER) has been described. HeLa cells were transfected using the AdpL method with pcDNA3/BAG-1 alone, the anti-BAG-1 sFvs 11, 15, 20 alone or cotransfected with pcDNA3/BAG-1 and the anti-BAG-1 sFvs 11, 15, respectively. The HeLa cell line was chosen because of its high transducibility by AdpL and the fact that this system was previously validated with another sFv. Forty-eight hours post-transfection, the expression of BAG-1 was evaluated by Western blot analysis. As shown in FIG. 25A, lower levels of BAG-1 protein were detected in HeLa cells cotransfected with BAG-1 and the anti-BAG-1 sFv constructs in comparaison to those that were transfected with BAG-1 alone. Although BAG-1 expression was still detectable in HeLa cells cotransfected with the anti-BAG-1 11, sFvs 15 and 20 achieved complete abrogation of BAG-1 expression. To confirm that the down-regulation of BAG-1 correlated with expression of anti-BAG-1 sFvs in these cells, an immunoblot analysis was performed to detect the sFv proteins. As shown in FIG. 25B, expression of the anti-BAG-1 sFvs was detectable where HeLa cells were transduced with the anti-BAG-1 constructs. Even though the same amount of total protein was loaded in each lanes (validated by Coomasie Blue staining), the sFv protein expression varied from one clone to another. Nevertheless, even at low level protein expression, the anti-BAG-1 sFvs were still able to down-regulate BAG-1.

The ability of the anti-BAG-1 sFvs to modulate the expression of BAG-1 was not restricted to HeLa cells. Two other cell lines, MCF-7, a breast cancer cell line and DU 145, a prostate cancer cell line, were transfected with the anti-BAG-1 sFv 20, the BAG-1 vector or both, and BAG-1 expression was compared to cells transfected with pSTCF.KDEL and BAG-1 (controls). As shown in FIG. 26A, the anti-BAG-1 sFv 20 completely abrogated the expression of BAG-1 compared to the plasmid controls in these cells. Ablation of BAG-1 expression was also correlated with expression of the sFv in these cells (FIG. 26B). The results demonstrate that the activity of the anti-BAG-1 sFv is not restricted to a specific cell type.

To determine if the BAG-1 protein or the anti-BAG-1 sFv could influence the proliferation of DU145 and MCF-7 under normal growth conditions, these cells were transfected by the AdpL method with the BAG-1 expression vector, the anti-BAG-1 sFv, both or BAG-1 cDNA and pSTCF.KDEL. As shown in FIG. 27, overexpression of BAG-1 per se did not significantly influence the growth rate of DU145 and MCF-7. Identical results were obtained with the anti-BAG-1 sFv suggesting that by itself this sFv had no negative effect on cell proliferation.

EXAMPLE 27
Abolition of the BAG-1-mediated resistance to cell killing by the anti-BAG-1 sFv To determine whether the anti-BAG-1 sFv-induced modulation of the BAG-1 protein can abolish the relative resistance to cytotoxicity conferred by this protein in MCF-7 cell, the anti-BAG-1 sFv 20, Bag-1 or both plasmids were transfected by the AdpL method and 24 hours later the transfected MCF-7 cells were treated with staurosporine or CDDP. The cell survival was assessed 4 days after the addition of the drugs. Similar experiments were conducted in DU145 as these cells do not express Bcl-2. As expected, the down-regulation of BAG-1 expression in MCF-7 cells completely abrogated the protective effect of BAG-1 (FIGS. 28A–B). In contrast, BAG-1 down-regulation in DU145 cells had no impact on their survival following exposure to drugs (FIGS. 28C–D). Transfection of the anti-BAG-1 sFv alone had no effect on the survival of both cell lines compared to the control (mock-transfected cells). Cotransfection of BAG-1 cDNA and pSTCF.KDEL in MCF-7 resulted in increased cell survival, demonstrating that pSTCF.KDEL by itself does not affect BAG-1-mediated protection from cytotoxicity. Similar results were obtained with the two cytotoxic drugs. Taken together, these results demonstrate the potency of the anti-BAG-1 sFv to overcome the relative resistance to cell killing conferred by the coexpression of BAG-1 and Bcl-2 in breast cancer cells. Furthermore, the absence of any effect in MCF-7 and DU145 cells following gene transfer of the anti-BAG-1 sFv 20 alone suggest that this sFv acts in a specific way.

EXAMPLE 28
Conclusions based on the use of sFvs directed towards Bcl-2 and BAG-1

Using a novel method based on the intracellular expression of a single-chain antibody directed against the Bcl-2 protein, the present invention demonstrates selective down-regulation of Bcl-2 protein expression in different epithelial tumor cell lines. This effect was dependent upon the ratio of anti-Bcl-2 sFv/Bcl-2 protein. A relative excess of anti-Bcl-2 sFv protein was required to achieve efficient down-regulation of the Bcl-2 protein in a situation where both cDNAs were driven by the CMV promoter. However, in tumor cells endogenously overexpressing Bcl-2, the level of Bcl-2 expression was significantly lower than that obtained via heterologous gene transfer. Therefore, an excess of anti-Bcl-2 sFv protein can easily be achieved in these cells with a CMV driven vector. In fact, significant down-regulation of the Bcl-2 protein has been achieved in endogenously Bcl-2 expressing MCF-7 cells.

The present invention demonstrates that BAG-1 has anti-apoptotic activity in a breast cancer cell line that overexpresses Bcl-2. Expression of an intracellular ER-targeted anti-BAG-1 sFv was able to abrogate the expression of BAG-1 and thereby abolish the anti-apoptic activity of BAG-1 in these cells. This is the first report that demonstrates the biological importance on down-modulation of BAG-1. These gene transfer experiments clearly show that sFv-mediated abrogation of BAG-1 can reverse its ability to block cell death.

EXAMPLE 29
Intracellular sFv anti-cyclin-D1 can knockout cyclin D1 protein expression and alter tumor cell growth Cyclins and cyclin-dependent kinases (cdks) are central to the regulation of the eukaryotic cell cycle. The role of cell cycle in modifying radiation sensitivity has been well established. Abrogating genes involved in cell cycle regulation can enhance radiosensitization. To show the effect of down-regulating cyclin-D1 on cell cycle progression, a sFv to cyclin-D1 was developed from the hybridoma cell line DCS-6. The DCS-6 hybridoma produces an antibody specific for the cyclin-D1 oncoprotein. The corresponding $V_L$ and $V_H$ chains of the DCS-6 RNA were amplified using RT-PCR and successfully assembled into an anti-cyclin-D1 sFv (FIG. 29A). The sFv library was subcloned into the prokaryotic expression vector pCANTAB5E in frame with a C-terminal E-tag for subsequent detection. To evaluate the expression of the anti-cyclin-D1 sFv E. coli were used to obtain periplasmic extract. Western blot analysis demonstrated sFv protein expression in the prokaryotic system only under induced conditions (FIG. 29B). Thus, the anti-cyclin-D1 sFv protein of 27 kDa was produced in the eukaryotic system. To determine the binding activity of the engineered anti-cyclin-D1 sFv, periplasmic fractions were obtained and an ELISA was used to determine specific binding to 40 mg of purified cyclin-D1 protein. Two rounds of colony lift assay were performed to isolate purified clones with the best binding affinity. As shown in FIG. 29C panels of 10 different subclones from clones 3 and 34 were assayed. The binding affinity of clone 34.1 and 34.8 was comparable to the parental mAb, DCS-6. Thus, an anti-cyclin-D1 sFv was produced with binding affinity similar to the parental antibody.

To evaluate the trafficking of heterologous proteins employing the targeted eukaryotic expression plasmids the localization of the green fluorescent protein (GFP) reporter to the different intracellular compartments was evaluated. For this analysis the ER (KDEL retention signal) and nuclear GFP-fusion protein vectors were transfected in HeLa cells using the AdpL method. Transduced cells were evaluated under a fluorescent microscope (FIG. 30A). The GFP reporter was localized to the targeted subcellular compartment by the appropriate plasmid vector. The expression of anti-cyclin-D1 sFv was assayed for the nuclear and ER forms of the sFv in transfected HeLa cells. Western blot analysis were performed as shown in FIG. 30B. A band at 27 kDa corresponding to the expected molecular weight of the anti-cyclin-D1 sFv protein was detected for both expression vectors. Thus, the anti-cyclin-D1 sFv can be expressed in both the nuclear and ER of eukaryotic cells.

To characterize the ability of the anti-cyclin-D1 sFv to down regulate cyclin-D1 protein expression, experiments using AdpL transfection were done in a normal breast cell line (HBL-100) which does not overexpress cyclin-D1 and in a cyclin-D1 overexpressing breast cancer cell line MDA-MB-453). Plasmid DNAs encoding the ER form (erCD1scFv34.1) or a nuclear form (nCD1scFv34.1) of anti-cyclin-D1 sFv were used. The pcDNA3 plasmid was used as a control. Transfected cells were evaluated by Western blot analysis (FIG. 30C). No difference in the expression of cyclin-D1 protein in the HBL-100 cells was detected. The MDA-MB-453 cells demonstrated a significant reduction in cyclin-D1 protein levels by fives days post transfection with the nuclear form of the anti-cyclin-D1 sFv. Thus, an anti-cyclin-D1 sFv localized to the nucleus of the cell could achieve down modulation of the targeted protein in MDA-MB-453 cells.

To determine the biological effect of anti-cyclin-D1 sFv expression, analysis of cell cycle progression was done. Cyclin-D1 is essential for progression through the G1 phase of the cell cycle. Cell cycle analysis was done using FACS analysis following propidium iodide (PI) staining. No changes were observed in cell cycle kinetics in the HBL-100 cell line treated with the different forms of the anti-cyclin- D1 sFv (FIG. 31). However, in the MDA-MB-453 cells a specific delay of S phase entry was seen in the cells treated with the ER and nuclear forms of the anti-cyclin-D1 sFv (FIG. 31). Specifically, cellular DNA FACS analysis of nonsynchronized MDA-MB-453 cells when treated with the nuclear form of the anti-cyclin-D1 sFv showed a 22% increase in the proportion of cells in G1 and a concomitant reduction of actively dividing cells compared to only 8% with the ER form of the sFv. Another cell line that overexpresses cyclin-D1 (MCF-7) was used to confirm the previous results. MCF-7 cells showed a delayed S phase entry with a 37% increase in cells in G1 transfected with the nuclear form of the anti-cyclin-D1 sFv. Thus the anti-cyclin-D1 sFv was able to achieve selective blockage of cell cycle progression by accumulating cells in the G1 phase of the cell cycle.

The cell cycle arrest was additionally manifested as a reduction of viable cells at various time points. Five days post transfection MDA-MB-453 cells expressing the nuclear-localized anti-cyclin-D1 sFv showed extensive cell death as assessed by trypan blue exclusion. This cell death was not apparent in MDA-MB-453 cells transfected with the control plasmid pcDNA3 (FIG. 32). Thus, the expression of the nuclear form and ER form of the anti-cyclin-D1 sFv alters the cell cycle kinetics of cyclin-D1 overexpressing breast cancer cells but not in cells expressing normal levels of cyclin-D1 protein. Therefore, the expression of an sFv that alters the cell cycle kinetics of cells overexpressing cyclin-D1 may have an important role in sensitizing tumor cells to ionizing radiation.

FIG. 33 shows that in a direct analysis of viable cells, the nuclear form of the anti-cyclin-D1 scFv induced 60% reduction in the number of viable cells in MCF-7 and MDA-MB-453. In contrast, the ER form of the scFv only achieved close to 40% reduction in cell viability in those same cells. Thus, the expression of the nuclear and ER form of this scFv alters the cells cycle kinetics and exhibits a selective antiproliferative effect in overexpressing cyclin D1 breast cancer cells.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of enhancing the radiosensitivity of a neoplastic cell, comprising the steps of:
   (a) introducing into the cell an antibody homologue, wherein the antibody homologue is expressed intracellularly and binds to a target protein intracellularly, wherein said target protein is known to stimulate either cell proliferation or neoplastic transformation; and,
   (b) administering radiation to said cell, wherein radiosensitivity of said cell is enhanced by the intracellular presence of said antibody homologue.

2. The method of claim 1, wherein said antibody homologue binds in the endoplasmic reticulum of the cell.

3. The method of claim 1, wherein said neoplastic cell expresses a target protein that stimulates proliferation of the cell.

4. The method of claim 1, wherein said neoplastic cell is selected from the group consisting of ovarian cancer, bladder cancer, lung cancer, cervical cancer, breast cancer, prostate cancer, gliomas, fibrosarcomas, retinoblastomas, melanomas, soft tissue sarcomas, ostersarcomas, leukemias, colon cancer, carcinoma of the kidney, gastrointestinal cancer, salivary gland cancer and pancreatic cancer.

5. The method of claim 1, wherein said target protein is selected from the group consisting of growth factor receptor proteins, cell cycle control proteins and anti-apoptotic proteins.

6. The method of claim 5, wherein said growth factor receptor protein is selected from the group consisting of erbB2 and epidermal growth factor receptor.

7. The method of claim 5, wherein said anti-apoptotic protein is selected from the group consisting of Bcl-2 and BAG-1.

8. The method of claim 5, wherein said cell cycle control protein is selected from the group consisting of cyclin D1 and cyclin B.

9. The method of claim 1, wherein said antibody homologue is selected from the group consisting of a single chain Fv fragment and a Fab fragment.

10. The method of claim 1, wherein said antibody homologue is introduced to the cell via a nucleic acid molecule encoding said antibody homologue.

11. The method of claim 10, wherein said nucleic acid molecule is a recombinant expression vector selected from the group consisting of a viral vector and a plasmid vector.

12. The method of claim 1, further comprising the step of contacting said cell with an anti-neoplastic agent, radiation or a combination thereof.

13. The method of claim 12, wherein said anti-neoplastic agent is selected from the group consisting of cisplatin, a halogenated pyrimidine, fluoropyrimidines, taxol, BCNU, 5-fluorouracil, bleomycin, mitomycin, hydroxyurea, fludarabine, nucleoside analogues, topoisomerase I inhibitors, hypoxic cell sensitizers and etoposide.

14. A method of enhancing the radiosensitivity of a neoplastic cell, comprising the step of:
   introducing into the cell an antibody homologue, wherein the antibody homologue is expressed intracellularly and binds to a target protein intracellularly, wherein said target protein is known to stimulate either cell proliferation or neoplastic transformation; and
   contacting said cell with radiation or radiation in combination with an anti-neoplastic chemotherapeutic agent.

15. The method of claim 14, wherein said target protein is erbB2.

16. The method of claim 14, wherein said target protein is epidermal growth factor receptor.

17. The method of claim 14, wherein said target protein is Bcl-2.

18. The method of claim 14, wherein said target protein is cyclin D1.

19. The method of claim 14, wherein said target protein is BAG-1.

* * * * *